United States Patent
Prystupa et al.

(10) Patent No.: US 12,370,276 B2
(45) Date of Patent: Jul. 29, 2025

(54) APPARATUS FOR REFLECTING AN INCIDENT RAY OF ELECTROMAGNETIC RADIATION

(71) Applicant: 12180235 Canada Ltd., Winnipeg (CA)

(72) Inventors: David Allan Prystupa, Pinawa (CA); John Stephen Pacak, Winnipeg (CA)

(73) Assignee: 12180235 Canada Ltd., Winnipeg (CA)

( * ) Notice: Subject to any disclaimer, the term of this patent is extended or adjusted under 35 U.S.C. 154(b) by 1048 days.

(21) Appl. No.: 17/378,171

(22) Filed: Jul. 16, 2021

(65) Prior Publication Data

US 2022/0016306 A1   Jan. 20, 2022

Related U.S. Application Data

(60) Provisional application No. 63/084,860, filed on Sep. 29, 2020, provisional application No. 63/065,091, (Continued)

(51) Int. Cl.
*A61L 9/20* (2006.01)
*A61L 2/00* (2006.01)
(Continued)

(52) U.S. Cl.
CPC .............. *A61L 2/0047* (2013.01); *A61L 2/10* (2013.01); *A61L 2/26* (2013.01); *A61L 9/20* (2013.01); *A61L 9/205* (2013.01); *A62B 7/12* (2013.01); *A62B 9/00* (2013.01); *A62B 18/02* (2013.01); *A62B 18/08* (2013.01); *G02B 5/0891* (2013.01); *G21K 1/062* (2013.01); *A61L 2202/11* (2013.01);
(Continued)

(58) Field of Classification Search
CPC . A61L 2/0047; A61L 2/10; A61L 2/26; A61L 9/20; A61L 9/205; A61L 2202/11; A61L 2202/14; A61L 2209/111; A61L 2202/122; A62B 7/12; A62B 9/00; A62B 18/02; A62B 18/08; A62B 9/02; A62B 18/006; G02B 5/0891; G02B 19/0066; G02B 5/10; G02B 5/208; G02B 5/223; G02B 5/23; G02B 5/0825; G21K 1/062; F24F 8/22; F24F 2221/38
See application file for complete search history.

(56) References Cited

U.S. PATENT DOCUMENTS 6,041,610 A    3/2000  Edwards et al.
9,318,649 B2   4/2016  Eliason
(Continued)

FOREIGN PATENT DOCUMENTS

JP   2010100682   5/2010

*Primary Examiner* — Regina M Yoo
(74) *Attorney, Agent, or Firm* — Adrian D. Battison; Ade & Company Inc.; Ryan W. Dupuis

(57) ABSTRACT

A flow through photochemistry apparatus and methods of use are disclosed in the present application. One or more reactant materials are passed through a reaction chamber and are exposed to electromagnetic radiation. The reaction chamber has reflective walls arranged to reflect electromagnetic radiation across the volume of the chamber a plurality of times, thereby increasing the probability of the electromagnetic radiation interacting with the reactive materials.

(Continued)

The reaction chamber may be used for sterilization and photochemistry applications.

23 Claims, 24 Drawing Sheets

Related U.S. Application Data filed on Aug. 13, 2020, provisional application No. 63/053,237, filed on Jul. 17, 2020.

(51) Int. Cl.
| | |
|---|---|
| *A61L 2/10* | (2006.01) |
| *A61L 2/26* | (2006.01) |
| *A62B 7/12* | (2006.01) |
| *A62B 9/00* | (2006.01) |
| *A62B 18/02* | (2006.01) |
| *A62B 18/08* | (2006.01) |
| *G02B 5/08* | (2006.01) |
| *G21K 1/06* | (2006.01) |
| *A62B 9/02* | (2006.01) |
| *A62B 18/00* | (2006.01) |
| *F24F 8/22* | (2021.01) |

(52) U.S. Cl.
CPC ...... *A61L 2202/14* (2013.01); *A61L 2209/111* (2013.01); *A62B 9/02* (2013.01); *A62B 18/006* (2013.01); *F24F 8/22* (2021.01)

(56) References Cited

U.S. PATENT DOCUMENTS

| | | |
|---|---|---|
| 9,511,344 B2 | 12/2016 | Cooper et al. |
| 10,472,260 B2 | 11/2019 | Mochizuki et al. |
| 2003/0086848 A1* | 5/2003 | Saccomanno ........... C02F 1/325 422/305 |
| 2004/0166018 A1* | 8/2004 | Clark ...................... A61L 9/205 422/4 |
| 2005/0163648 A1* | 7/2005 | Liang ........................ A61L 9/20 422/186 |
| 2008/0152548 A1* | 6/2008 | Clark ...................... A61L 9/205 422/121 |
| 2009/0098014 A1* | 4/2009 | Longstaff ................. F24F 3/16 422/4 |
| 2015/0314024 A1* | 11/2015 | Khan ........................ A61L 2/10 250/435 |
| 2017/0373045 A1 | 12/2017 | Welch |
| 2019/0009912 A1* | 1/2019 | Matsui .................. B64D 13/02 |
| 2019/0134249 A1* | 5/2019 | Taboada .................... A61L 9/20 |
| 2019/0184045 A1* | 6/2019 | Mochizuki ................ A61L 2/10 |
| 2020/0108528 A1 | 4/2020 | Oliver |
| 2020/0164099 A1 | 5/2020 | Durrstein |
| 2022/0102583 A1 | 3/2022 | Baumheinrich |
| 2022/0177330 A1* | 6/2022 | Fisher .................... G01N 21/59 |
| 2022/0362419 A1* | 11/2022 | Tanaka ...................... A61L 2/10 |
| 2022/0370676 A1* | 11/2022 | Yamine ................. B01D 47/02 |

\* cited by examiner

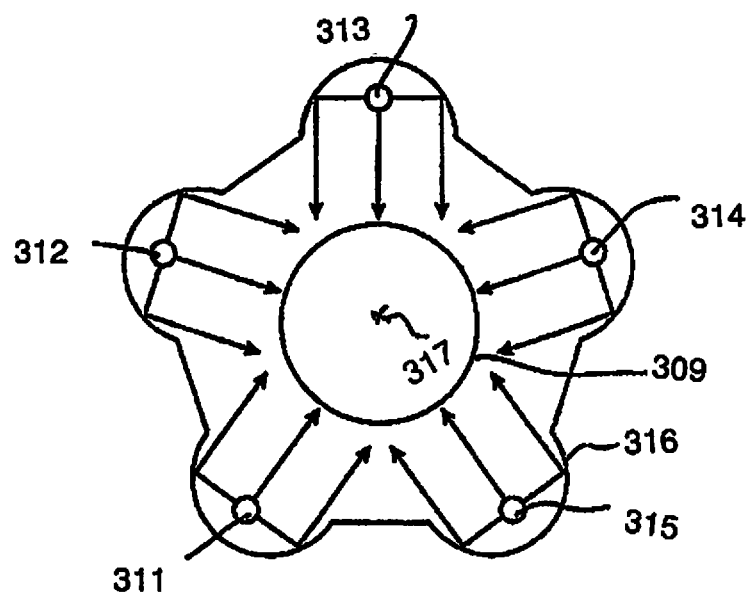
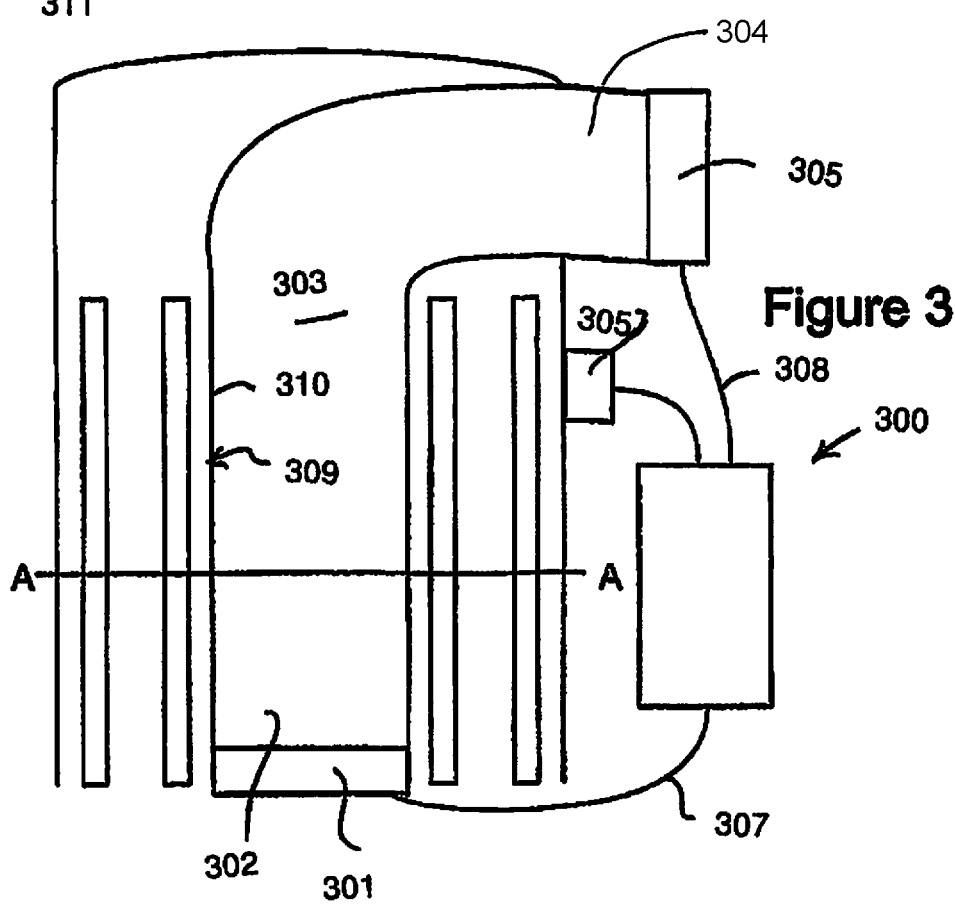
Figure 3A
Figure 3B

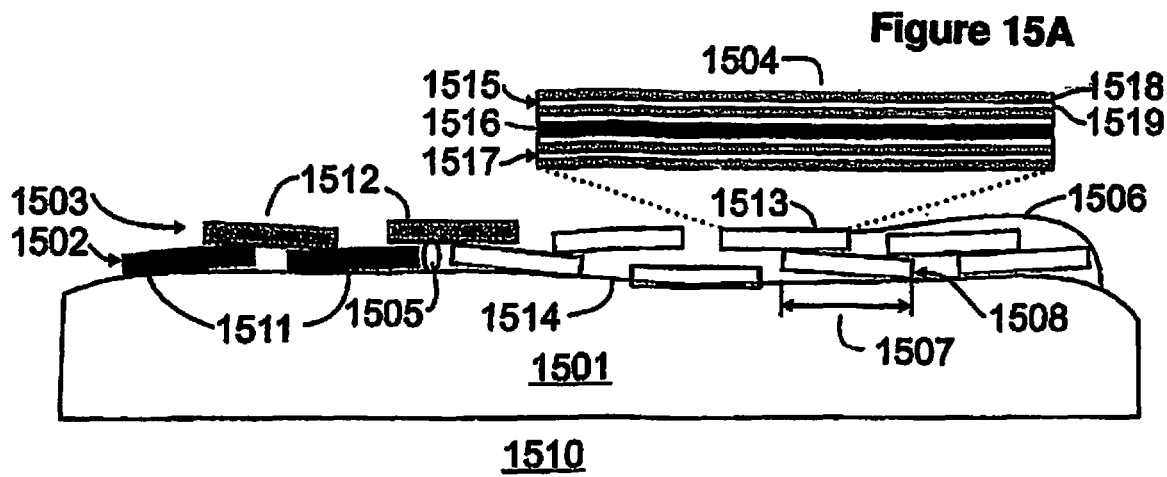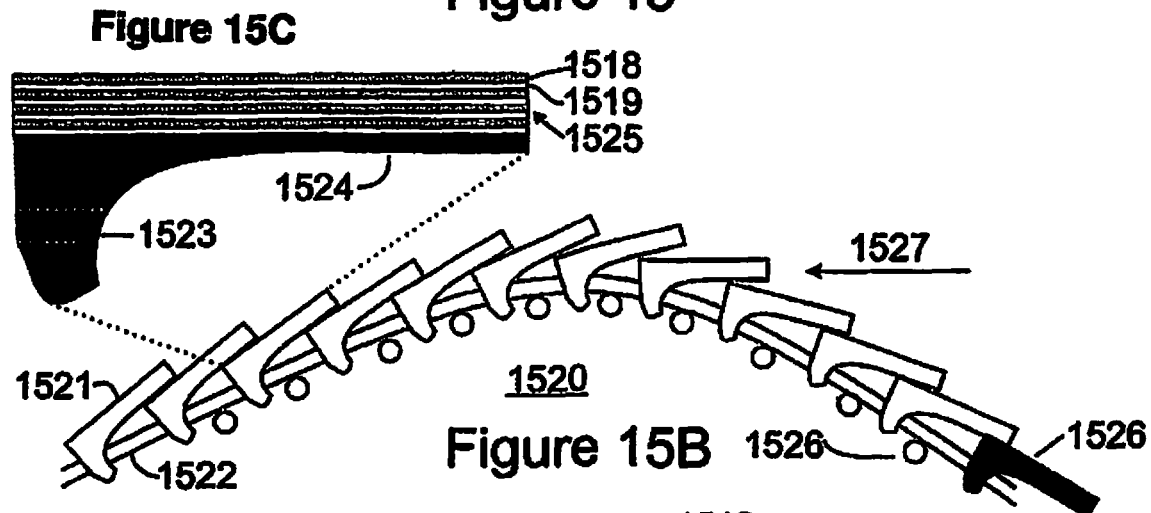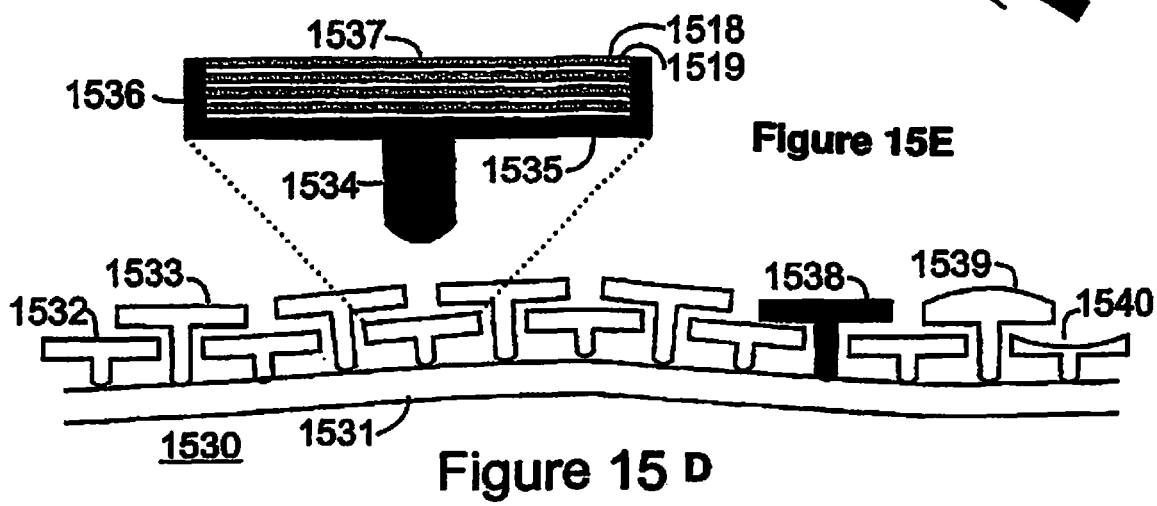
Figure 15

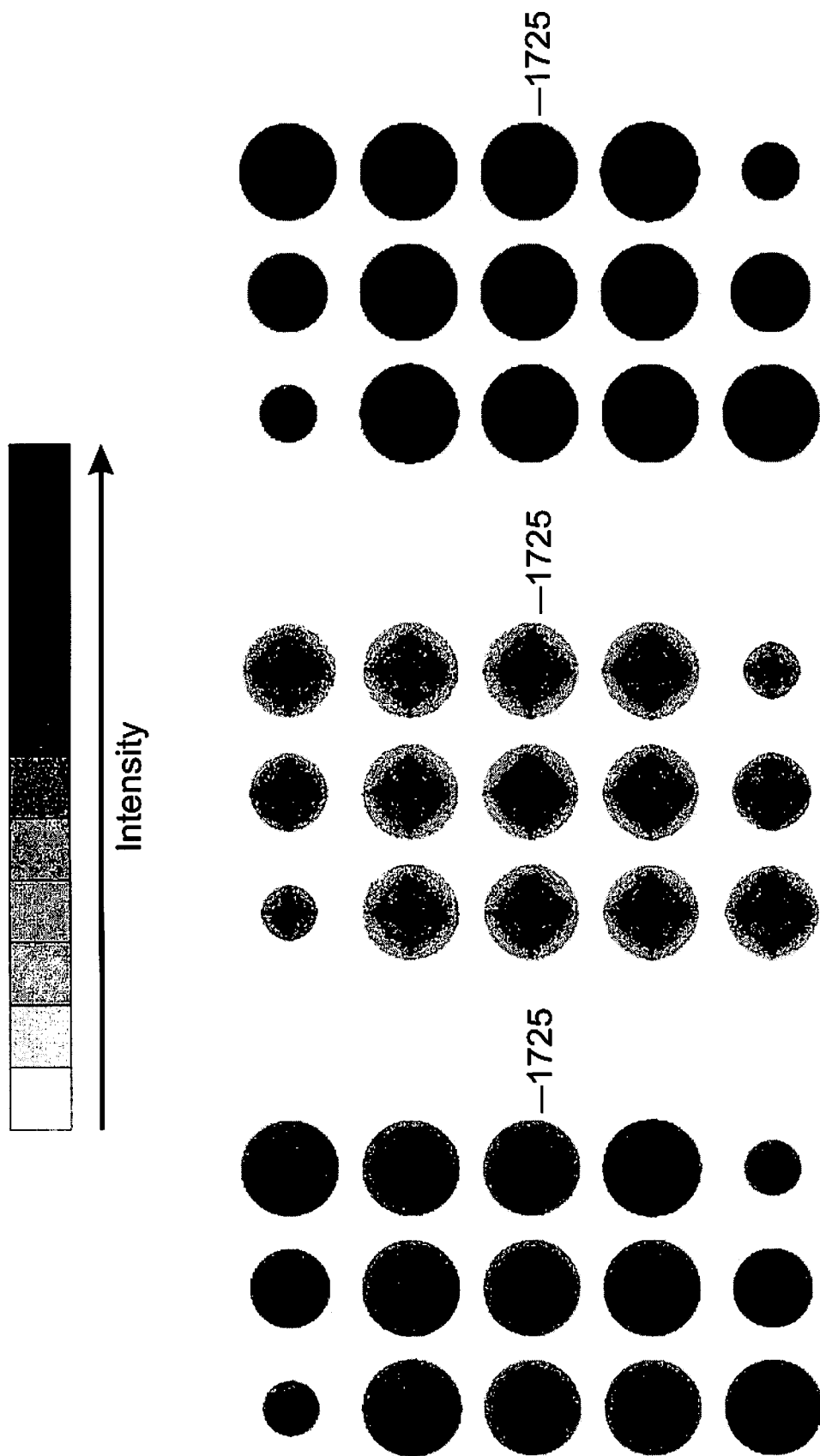

APPARATUS FOR REFLECTING AN INCIDENT RAY OF ELECTROMAGNETIC RADIATION

This application relates in general to an apparatus or method for reflecting an incident ray of electromagnetic radiation which can be used in many different embodiments as disclosed in detail hereinafter.

For example, a flow through photochemistry apparatus and methods of use are disclosed in the present application. One or more reactant materials are passed through a reaction chamber and are exposed to electromagnetic radiation.

The reaction chamber may have reflective walls or mirrors arranged to reflect electromagnetic radiation across the volume of the chamber a plurality of times, thereby increasing the probability of the electromagnetic radiation interacting with the reactive materials. The reaction chamber may be used for sterilization and photochemistry applications.

The reflecting system can however be used in many other locations where high efficiency reflection is required.

BACKGROUND OF THE INVENTION

The pandemic spread of the SARS-CoV-2 virus has created an urgent need for means to limit the airborne transmission of infectious particles. Ultraviolet (UV) radiation is known to deactivate virus particles, but widespread use of UV technologies is limited by the high cost of UV sources and the relatively long exposure times required. Long exposure times are required because prior art devices make inefficient use of UV photons. In the simplest arrangement, a UV source is positioned proximate to a sample material to be irradiated, a portion of the photon flux impinges on the sample, and a fraction of the impinging flux interacts with the sample. The remainder of the photon flux is absorbed by the apparatus. That is each UV photon generated has only a small probability of interacting with the sample material. Prior art systems fall into three classes. In the first class metallic walls are provided that reflect photon flux specularly causing a portion of the photon flux to pass through the sample material a plurality of times. Aluminum is known to be an excellent metallic reflector in the UV region, but the reflectivity depends on angle of incidence and polarization averaging about 90%. The sum of intensity for an infinite number of reflections is given by $1/(R-1)$ setting a theoretical limit to 10-fold amplification for this class. In the second class, a diffuse reflector such as sintered PTFE is used. The reflectivity is about 97% giving a theoretical limit of 33-fold amplification. The effective amplification is less however because with a Lambertian distribution of reflected angles, the mean free photon path length between successive diffuse reflectance sites is short. The third class is based on total internal reflection within a liquid wherein there is no absorption loss for angles of incidence above a critical angle. The performance of this class is limited to the extent that light is scattered into angles less than the critical angle.

Photochemical reactions have applications ranging from the synthesis of specialty products to neutralizing pollutants. The range of commercially viable applications is limited by energy cost.

SUMMARY OF THE INVENTION

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

wherein the reaction chamber includes two opposing reflective surfaces of the chamber arranged to cause reflections of the electromagnetic radiation back and forth within a volume between the reflective surfaces;

wherein at least one of the reflective surfaces is a concave mirror.

According to one optional feature of the invention which can be used with any of the other features defined herein at least one reflective surface of the reaction chamber comprises a dielectric mirror with reflectivity at the selected wavelengths greater than 99%.

According to one optional feature of the invention which can be used with any of the other features defined herein a majority of radiation paths include at least ten and preferably more than one hundred reflections.

According to one optional feature of the invention which can be used with any of the other features defined herein there is provided a further reflective surface between the two reflective surfaces or the path may be a straight line path with no reflections or deviations. The further reflective surface may for example be a reaction chamber side wall oriented substantially perpendicular to the optical axis between the two reflective surfaces.

According to one optional feature of the invention which can be used with any of the other features defined herein the further reflective mirror surface is metallic.

According to one optional feature of the invention which can be used with any of the other features defined herein the reflective surfaces define at least one center optical axis extending therebetween along which the reflections pass and the source is preferably located at a position offset from the center axis between the reflective surfaces so that a locus of the reflections moves toward the center axis.

The source can be any one of many known arrangements for generating and emitting the required electromagnetic radiation or photons. The term "source" can relate to the actual component generating the radiation. Or the generating component can be located at a different or remote location and the radiation carried to the required emission location by a transmission device such as a light pipe. In this case the source can be considered as the exit point of the transmission device. Such light pipes can be rigid and typically straight or can be flexible such as a fiber optic to carry the radiation along a convoluted path. The radiation can also form a beam which is redirected by any redirecting component such as a prism or a mirror so as to be directed along the required path. The redirecting components can be located at the surface of the chamber so as in effect to form an orifice, or may be internal to the chamber.

According to one optional feature of the invention which can be used with any of the other features defined herein the source is located at one side of said at least one concave mirror.

According to one optional feature of the invention which can be used with any of the other features defined herein the source is located at a position on said at least one concave mirror. The source may have a dimension which is less than 0.03 times the focal length of the mirror.

According to one optional feature of the invention which can be used with any of the other features defined herein the offset between each beam and a next beam after a reflection is less than a width of the beam so that the beams form a complete curtain.

According to one optional feature of the invention which can be used with any of the other features defined herein there is provided an inlet port for admitting reactive materials and an outlet port for discharging product materials and there is provided absorbing surfaces formed and shaped to stop transmission of electromagnetic radiation from the interior of the chamber to an exterior location. Preferably the inlet and outlet ports are not on an axis of symmetry of the reaction chamber.

According to one optional feature of the invention which can be used with any of the other features defined herein at least part of a chamber wall reflects electromagnetic radiation diffusely.

According to one optional feature of the invention which can be used with any of the other features defined herein the method includes using a further electromagnetic radiation to obtain information relating to the reactant materials where the further electromagnetic radiation has a further wavelength different from said wavelength at which the dielectric mirror reflects the electromagnetic radiation at the wavelength at a second lower percentage.

According to one optional feature of the invention which can be used with any of the other features defined herein a volume accessible to reactive material flowing through the reaction chamber is constrained by a transparent material to less than the volume accessible to electromagnetic radiation within the reaction chamber.

According to one optional feature of the invention which can be used with any of the other features defined herein the reactive material is entrained in a fluid flow wherein the fluid is a liquid or a gas.

According to one aspect of the invention which can be used independently or with any of the other features defined herein there is provided an electric field is generated in the reaction chamber and said electric field enhances absorption of electromagnetic radiation by said reactant materials. Preferably the electric field is operable to orient molecules within reactive materials relative to the polarization of the EM radiation field at a location in the reaction chamber.

According to one optional feature of the invention which can be used with any of the other features defined herein the electromagnetic radiation is UVC radiation and the reactive material is a microorganism selected from the list of bacteria, virus, protozoan, helminth, yeast, mould or fungus and said UVC radiation inactivates said microorganism.

According to one optional feature of the invention which can be used with any of the other features defined herein the electromagnetic radiation is at least partially collimated to travel primarily back and forth between the reflective surfaces.

According to one optional feature of the invention which can be used with any of the other features defined herein the surfaces can be of different shapes and diameters to match the profile of a contained into which they are inserted. Thus for example in a water container or bottle a larger end may have a larger surface and an opposed end be smaller According to one optional feature of the invention which can be used with any of the other features defined herein, when used with liquid, for example for sterilizing water, the chamber can be arranged so that it is fully filled by gravity by the entering liquid so as to avoid liquid surfaces within the chamber which can interfere with the radiation paths and cause unsuitable or less efficient reflections.

According to one optional feature of the invention which can be used with any of the other features defined herein, the source can be a radiant cylindrical tube located within the chamber preferably at an orientation parallel to the optical axis but optionally at other orientations such as right angle to the axis. If parallel to the axis, the tube can be located on the axis or spaced outwardly from the axis. The preferred or optimum position locates the tube at a spacing from the axis of one half of the radius of the concave surface.

According to one optional feature of the invention which can be used with any of the other features defined herein, the concave mirror can be formed with a central section at the axis which is a dielectric mirror and on outer ring of a material of reduced reflectivity such as polished aluminum.

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

wherein a source of at least some of the electromagnetic radiation is external to the reaction chamber and the electromagnetic radiation from a radiation emitting area of said source is introduced into the reaction chamber from said source through an orifice.

In this arrangement, preferably the radiation from said emitting area is directed such that substantially all passes through the orifice.

In this arrangement, preferably the orifice is of a smaller area than a body of the source.

In this arrangement, the orifice can comprise an aperture or alternatively the orifice comprises a light pipe. The term light pipe is intended to include any light transmission system where light is carried from a source to a required located. Such light pipes can be rigid or flexible.

In this arrangement, preferably the orifice is sized and positioned to reduce an amount of electromagnetic radiation incident thereon and exiting the reaction chamber through the orifice and being re-absorbed by the source. Thus the orifice can emit the radiation into a first solid angle entering the chamber, but restrict the exit of the light in view of the small transverse dimension and hence small second solid angle the orifice presents to radiation reflected from points within the chamber. Thus the orifice, or the source itself where there is no orifice, is preferably offset from the optical axis as defined herein so that the probability of light returning to the orifice is reduced to again reduce the proportion of injected radiation from exiting at the source or the orifice.

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

wherein the electromagnetic radiation is at least partially collimated.

According to one optional feature of the invention which can be used with any of the other features defined herein the chamber is shaped to define at least one optical axis and the at least partially collimated electromagnetic radiation is directed so as to preferentially propagate along the optical axis.

According to one optional feature of the invention which can be used with any of the other features defined herein said at least one optical axis includes at least one change in direction or the path can be a straight line.

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

wherein the electromagnetic radiation is UV light at a selected wavelength;

wherein at least one reflective surface of the reaction chamber comprises a dielectric mirror with reflectivity at the selected wavelengths greater than 99%.

According to one optional feature of the invention which can be used with any of the other features defined herein at least one reflective surface of the reaction chamber comprises a dielectric mirror with reflectivity at the selected wavelengths greater than 99% and another reflective surface comprises a reflective material of reduced reflectivity.

According to one optional feature of the invention which can be used with any of the other features defined herein the dielectric mirror comprises a stack of layers which has a first area arranged with selected thicknesses of the layers such that the incident ray of light is reflected by the stack if the angle of incidence of the ray falls within a first predetermined range of angles and is transmitted through the stack if the angle of incidence of the ray falls in a different predetermined range of angles and the stack has a second area arranged with selected thicknesses of the layers such that the incident ray of light is reflected by the stack if the angle of incidence of the ray falls within a second predetermined range of angles different from the first predetermined range of angles and is transmitted through the stack if the angle of incidence of the ray falls in a different predetermined range of angles. In this arrangement, preferably the second range does not overlap the first range.

According to one aspect of the invention which can be used independently or with any of the other features defined herein there is provided a method for reflecting an incident ray of electromagnetic radiation comprising:

providing a dielectric mirror formed by plurality of layers of dielectric materials arranged in a stack;

wherein the stack has a first area arranged with selected thicknesses of the layers such that the incident ray of light is reflected by the stack if the angle of incidence of the ray falls within a first predetermined range of angles and is transmitted through the stack if the angle of incidence of the ray falls in a different predetermined range of angles and wherein the stack has a second area arranged with selected thicknesses of the layers such that the incident ray of light is reflected by the stack if the angle of incidence of the ray falls within a second predetermined range of angles different from the first predetermined range of angles and is transmitted through the stack if the angle of incidence of the ray falls in a different predetermined range of angles.

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

wherein the chamber includes at least a portion formed by a dielectric mirror defined by layers carried on a substrate;

wherein the electromagnetic radiation has a wavelength selected so that the dielectric mirror reflects the electromagnetic radiation at the wavelength at a first percentage;

In this arrangement, preferably the dielectric mirror is substantially transparent at the second wavelength.

In this arrangement, preferably Raman scattered radiation is collected from the reaction chamber and analyzed to provide information about at least one reactive material.

In this arrangement, preferably infrared radiation transverses the chamber multiple times and the infrared absorption is analyzed to provide information about at least one reactive material, which can be used to control the parameters of the treatment.

According to one aspect of the invention which can be used independently or with any of the other features defined herein there is provided an apparatus for reflecting an incident ray of electromagnetic radiation comprising:

a dielectric mirror formed by plurality of layers of dielectric materials arranged in a stack;

wherein the dielectric mirror comprises a plurality of separate dielectric mirror components each formed by plurality of layers of dielectric materials arranged in a stack;

the mirror components being mounted on a flexible supporting substrate with each mirror component movable relative to the next to follow a flexing movement of the substrate.

In this arrangement, preferably each mirror component is rigid.

In this arrangement, preferably the mirror components are arranged in an array edge to edge.

In this arrangement, preferably the mirrors are arranged in an array where some of the mirror components overlap others of the mirror components so that electromagnetic radiation passing between two of the mirror components is reflected by an underlying third of the mirror components.

In this arrangement, preferably each mirror component is separately connected to the substrate.

In this arrangement, each mirror component can be attached to the substrate by adhesive.

In this arrangement, each mirror component can be attached to the substrate by electrostatic forces.

In this arrangement, each mirror component can be attached to the substrate as part of an ink layer.

In this arrangement, each mirror component can include a mounting arm which is attached to the substrate. In this arrangement, preferably the mounting arm includes an opening through which a fiber or wire or the like of the substrate passes. In this arrangement, preferably the mounting arm of some mirror components is longer than for other mirror components to hold the mirror components in an overlapping array. In this arrangement, preferably each mirror component has an aspect ratio of 10:1 or more. In this arrangement, preferably each mirror component has a linear dimension in the range of 10 microns to 2000 microns.

According to one aspect of the invention which can be used independently or with any of the other features defined herein there is provided a method for sterilizing airflow comprising:

providing a mask of a respirator having an airflow duct for air entering or exiting the mask;

the air flow duct including a treatment chamber though which the air passes in a stream;

introducing electromagnetic radiation into the chamber operable to sterilize the air;

and increasing the probability of interaction of the electromagnetic radiation with the reactant materials by using multiple reflections to increase the optical path length of the electromagnetic radiation through the reaction chamber;

According to one optional feature of the invention which can be used with any of the other features defined herein the chamber is mounted on headwear.

According to one optional feature of the invention which can be used with any of the other features defined herein the headwear includes a face shield and the duct includes an aperture proximate to the top of the face shield.

According to one optional feature of the invention which can be used with any of the other features defined herein there is provided an air movement device which generates positive air pressure between the face of the wearer and the mask. In this arrangement, preferably the chamber is deformable or collapsible. In this arrangement, preferably there is provided an expandable bladder for receiving excess air in the event of a sneeze or cough and wherein the bladder vents air at a controlled rate into the treatment chamber In this arrangement, preferably there is provided a sensor which detects an increase in air pressure associated with a cough or sneeze and wherein an amplitude of the radiation is increased.

According to one aspect of the invention which can be used independently or with any of the other features defined herein there is provided a method for sterilizing particles comprising:

singulating the particles into a stream of the particles arranged in a spaced row of the particles;

providing a treatment chamber though which the particles pass in the stream;

introducing electromagnetic radiation into the chamber operable to sterilize the particles;

and increasing the probability of interaction of the electromagnetic radiation with the particles by using multiple reflections to increase the optical path length of the electromagnetic radiation through the treatment chamber.

In this arrangement, preferably the particles are singulated by passing through at least one duct carried on a rotating member so that centrifugal forces generated by rotation of the rotating member overcome frictional forces between the particles and the duct to cause acceleration and separation of the particles in the duct.

According to one aspect of the invention which can be used independently or with any of the other features defined herein there is provided a method for applying electromagnetic radiation to reactant materials in a reaction chamber comprising:

introducing the electromagnetic radiation into the chamber;

and increasing the probability of interaction of the electromagnetic radiation with the reactant materials by using multiple reflections to increase the optical path length of the electromagnetic radiation through the reaction chamber;

the chamber having at least one port between an interior and an exterior;

wherein there is provided a mirror outside of said port so as to reflect escaping electromagnetic radiation back into the chamber.

According to one aspect of the invention which can be used independently or with any of the other features defined herein there is provided a method for sterilizing a forced air flow in a duct comprising:

passing the air flow through the duct in a stream;

introducing photons into the duct from at least one source operable to sterilize the air flow;

directing the photons in the duct along a specific path;

and arranging at least two reflective surfaces in the duct at spaced positions so as to cause reflections back and forth between the two reflective surfaces and thus increase the probability of interaction of the electromagnetic radiation with the air flow by increasing the optical path length of the photons through the duct.

According to one optional feature of the invention which can be used with any of the other features defined herein the air flow is generated by a fan having fan blades and wherein at least one of the reflective surfaces is provided by at least one component of the fan.

According to one optional feature of the invention which can be used with any of the other features defined herein the air flow is generated by a fan having fan blades and at least one of the reflective surfaces is provided by at least one blade of the fan.

According to one optional feature of the invention which can be used with any of the other features defined herein the air flow is generated by a fan having fan blades and at least two of the reflective surfaces are provided by blades of the fan to provide reflections between the two blades.

According to one optional feature of the invention which can be used with any of the other features defined herein the air flow is generated by a fan having fan blades and at least one of the reflective surfaces is provided by a hub of the fan.

According to one optional feature of the invention which can be used with any of the other features defined herein another of the reflective surfaces comprises a mirror at a position spaced radially outwardly from the fan blades.

According to one optional feature of the invention which can be used with any of the other features defined herein the fan blades have a reflective surface which is different in shape from an air engaging surface of the fan blade.

According to one optional feature of the invention which can be used with any of the other features defined herein the air engaging surface is transparent so that the photons pass through to the reflective surface.

According to one optional feature of the invention which can be used with any of the other features defined herein more than 75% of the reaction chamber interior surface has a specular reflection coefficient for electromagnetic radiation at the selected wavelengths greater than 90%.

According to one optional feature of the invention which can be used with any of the other features defined herein at least one reflective surface of the reaction chamber comprises a dielectric mirror with reflectivity at the selected wavelengths greater than 99% and another reflective surface comprises a reflective material of reduced reflectivity.

According to one optional feature of the invention which can be used with any of the other features defined herein electromagnetic radiation is transferred from a first location within the reaction chamber to a second location within the reaction chamber by a light pipe.

According to one aspect of the invention which can be used independently or with any of the other features defined herein there is provided a method for applying electromagnetic radiation to reactant materials in a reaction chamber comprising:
  providing at least two reflective surfaces at spaced positions so as to cause reflections back and forth between the two reflective surfaces and thus increase the probability of interaction of the electromagnetic radiation with the reactant materials by increasing the optical path length of the electromagnetic radiation;
  wherein the chamber is shaped to define an optical axis between said reflective surfaces;
  wherein the electromagnetic radiation is introduced into the chamber by at least one source arranged to emit the electromagnetic radiation mainly in the direction of the optical axis.

The optical axis can form a single straight path between the surfaces or the optical axis can be comprised of a plurality of straight paths where a redirecting body such as a reflective surface generates a second path at an angle to the first path.

According to one optional feature of the invention which can be used with any of the other features defined herein said at least two sources comprise two sources which are located at respective positions spaced outwardly from the axis and angularly spaced around the axis at an angle different from 90 degrees for example at 60 degrees.

According to one optional feature of the invention which can be used with any of the other features defined herein the two sources are located at respective positions spaced outwardly from the axis.

According to one optional feature of the invention which can be used with any of the other features defined herein the source or sources and the axis are arranged such that the back and forth reflections create a virtual source symmetrically located around the axis relative to the source which is at 180 degrees to the actual source. Thus a single source will generate an additional virtual source at 180 degree spacing and on the same radial distance from the axis. Similarly additional sources which are preferably therefore not at 180 degree spacing generate an array of actual and virtual sources around the axis.

According to one optional feature of the invention which can be used with any of the other features defined herein the electromagnetic radiation is introduced into the chamber by said at least two LED sources and the LED sources include separate heat sinks.

According to one optional feature of the invention which can be used with any of the other features defined herein the two LED sources each have a transverse dimension of an emitting area of less than 1 mm.

According to one aspect of the invention which can be used independently or with any of the other features defined herein there is provided a method for applying electromagnetic radiation to reactant materials in a reaction chamber comprising:
  providing at least two reflective surfaces at spaced positions so as to cause reflections back and forth between the two reflective surfaces and thus increase the probability of interaction of the electromagnetic radiation with the air flow by increasing the optical path length of the electromagnetic radiation;
  wherein the surfaces are shaped to define an optical axis of said at least one reflective surface;
  wherein the electromagnetic radiation is introduced into the chamber by at least one source;
  and wherein said at least one source is located at a position spaced outwardly from the axis;
  wherein said at least one source and the axis arranged such that the back and forth reflections create a virtual source symmetrically located around the axis at a position 180 degrees relative to said at least one source.

According to one aspect of the invention which can be used independently or with any of the other features defined herein there is provided an apparatus for applying electromagnetic radiation to reactant materials in a reaction chamber comprising:
  a reaction chamber defined by at least one reflective surface arranged to provide multiple reflections to increase the optical path length of the electromagnetic radiation through the reaction chamber;
  wherein the electromagnetic radiation is introduced into the chamber by at least two LED sources;
  and wherein the LED sources include separate heat sinks separated by enough that little heat diffuses between the LED sources.

According to one aspect of the invention which can be used independently or with any of the other features defined herein there is provided an apparatus for applying electromagnetic radiation to reactant materials in a reaction chamber comprising:
  a reaction chamber defined by at least one reflective surface arranged to provide multiple reflections to increase the optical path length of the electromagnetic radiation through the reaction chamber;
  wherein said at least one reflective surface is formed by a mirror layer carried on a substrate;
  wherein the electromagnetic radiation is introduced into the chamber by at least one LED;
  wherein the LED is carried on the substrate;
  and wherein the substrate carries electrically conductive components of an electrically conductive layer for providing power to the LED.

According to one optional feature of the invention which can be used with any of the other features defined herein the substrate additionally carries thermally conductive components for conducting heat away from the LED.

According to one optional feature of the invention which can be used with any of the other features defined herein the LED is located at a hole in the mirror layer.

According to one optional feature of the invention which can be used with any of the other features defined herein a lens is located in the hole in the mirror layer.

According to one optional feature of the invention which can be used with any of the other features defined herein the lens comprises a micro lens arranged to reduce the angular divergence of radiation emitted by a light emitting regions of the LED.

According to one optional feature of the invention which can be used with any of the other features defined herein the LED has a light emitting area and the hole is sized to match the size of the light emitting area.

According to one optional feature of the invention which can be used with any of the other features defined herein the electrically conductive components comprise conductive traces lying longitudinally along the substrate beneath the mirror layer.

According to one optional feature of the invention which can be used with any of the other features defined herein the conductive traces are separated by one or more longitudinally extending insulating layers.

According to one optional feature of the invention which can be used with any of the other features defined herein the electrically conductive components form a layer patterned with a network of conductive strips analogous to a printed circuit board.

According to one optional feature of the invention which can be used with any of the other features defined herein the LED has an anode and cathode which are connected to separate conductive traces.

According to one aspect of the invention which can be used independently or with any of the other features defined herein there is provided an apparatus for applying electromagnetic radiation to reactant materials in a reaction chamber comprising:
  a reaction chamber defined by at least one reflective surface arranged to provide multiple reflections to increase the optical path length of the electromagnetic radiation through the reaction chamber;
  wherein said at least one reflective surface is formed by a mirror layer carried on a substrate;
  wherein the electromagnetic radiation is introduced into the chamber by at least one LED;
  wherein the LED is carried on the substrate;
  wherein the LED is located at a hole in the mirror layer.

According to one aspect of the invention which can be used independently or with any of the other features defined herein there is provided an apparatus for applying electromagnetic radiation to reactant materials in a reaction chamber comprising:
  a reaction chamber defined by at least one reflective surface arranged to provide multiple reflections to increase the optical path length of the electromagnetic radiation through the reaction chamber;
  wherein said at least one reflective surface is formed by a mirror layer carried on a substrate;
  wherein the electromagnetic radiation is introduced into the chamber by at least one LED;
  wherein the LED is carried on a support substrate separate from and mounted on said substrate;
  and wherein the support substrate is located with a light emitting area of the LED positioned at an aperture in the substrate and with an air gap between the substrate and the support substrate.

In this arrangement, preferably the aperture comprises a hole in the mirror layer.

In this arrangement, preferably a lens is located in the hole in the mirror layer.

According to one important feature of the invention which can be used alone or on combination with any of the other features of the invention, there is provided an apparatus for reflecting an incident ray of electromagnetic radiation comprising:
  a dielectric mirror formed by plurality of layers of dielectric materials arranged in a stack;
  the layers of dielectric materials in the stack being arranged with selected thicknesses such that the incident ray of light is reflected by the stack if the angle of incidence of the ray falls within a predetermined range of angles and is transmitted through the stack if the angle of incidence of the ray falls in a different predetermined range of angles;
  and a reflective mirror surface located behind the stack so that the transmitted rays are reflected by the mirror surface back through the stack.

In accordance with another important and independent feature, the reflective mirror surface is immediately adjacent or in contact with a rear surface of the stack.

In accordance with another important and independent feature, the reflective mirror surface is integral with a structural support for the stack.

In accordance with another important and independent feature, the stack contains alternate layers of dielectric materials where a selection of the materials and/or the thickness thereof determines the range of angles.

In accordance with another important and independent feature, the alternate layers comprise high refractive index and low refractive index materials.

According to one important feature of the invention which can be used alone or on combination with any of the other features of the invention, there is provided an apparatus for reflecting an incident ray electromagnetic radiation comprising:
  a dielectric mirror formed by plurality of layers of dielectric materials arranged in a stack;
  wherein one part of the stack has a first area arranged with selected thicknesses such that the incident ray of light is reflected by the stack if the angle of incidence of the ray falls within a first predetermined range of angles and is transmitted through the stack if the angle of incidence of the ray falls in a different predetermined range of angles and a second area arranged with selected thicknesses such that the incident ray of light is reflected by the stack if the angle of incidence of the ray falls within a second predetermined range of angles different from the first predetermined range of angles and is transmitted through the stack if the angle of incidence of the ray falls in a different predetermined range of angles.

According to one important feature of the invention which can be used alone or on combination with any of the other features of the invention, there is provided an apparatus for treating reactant materials comprising:
  a treatment chamber;
  an arrangement for forming a stream of the reactant materials which passes through the chamber in the stream;
  a source of photons of UV light arranged to be introduced into the chamber;
  one or more dielectric mirrors arranged to increase the probability of photon interaction with the reactant materials by using multiple reflections on to increase the optical path length of photons through a reaction region of the reaction chamber;
  wherein the dielectric mirrors have characteristics defined above or herein.

According to one important feature of the invention which can be used alone or on combination with any of the other features of the invention, there is provided an apparatus for supplying sterilized air to a wearer comprising:

headwear for wearing by a wearer;

a chamber through which air passes from environment around the headwear;

a source of UV light arranged for sterilizing the air in the chamber;

a duct for carrying the sterilized air from the chamber to a location adjacent the nose and mouth of the wearer.

In accordance with another important and independent feature, the probability of photon interaction with the reactant materials is obtained by using multiple reflections to increase the optical path length of photons through a reaction region of the reaction chamber.

In accordance with another important and independent feature, the headwear comprises a helmet. This can be a sports helmet such as for use in hockey, football or the like or can be any other type of helmet such as for construction or motorcycle or equestrian. The face shield or mask can be optional so that the sterilized air can be directed from a nozzle to a position in front of the face of the wearer without a confining mask.

In accordance with another important and independent feature, the chamber is mounted on the headwear. It may be integral but can also be detachable.

In accordance with another important and independent feature, the chamber is separate from the headwear.

In accordance with another important and independent feature, the chamber is enclosed within the helmet body.

In accordance with another important and independent feature, the headwear includes a face shield.

Preferably the duct includes an aperture proximate to the top of the face shield.

Preferably there is provided an air movement device which generates positive air pressure between the face of the wearer and the face shield Preferably the duct includes a nozzle a direction of which adjustable.

In accordance with another important and independent feature, wherein there is provided an air cooler.

In accordance with another important and independent feature, the headwear can comprise a hat, headband or balaclava. This can carry or be combined with a mask or shield in front of the face of the wearer.

Preferably each mirror is flat so that it has an aspect ratio of 10:1 or more.

Preferably each mirror is a micro-mirror so that it has a linear dimension in the range of 10 microns to 2000 microns.

In accordance with another important and independent feature, the flexible substrate can be used to form a chamber which is deformable or collapsible.

In accordance with another important and independent feature, the flexible substrate can be used to form a support for a dielectric mirror which flexes in response to environmental activity to prevent fracturing of the dielectric mirror.

The mirror arrangement herein can be used in many different situations. For example it can be used in a multi-pass photochemistry system that increases the probability of photon interaction with reactant material by increasing the optical path length of photons through a reaction region.

In one important application the reactant is a chemical substance that is modified by a photochemical reaction.

In another important application, a first reactant, which may be a catalyst or electron donor acceptor (EDA), is raised to an excited state by absorption of one or more photons and said reactant in excited state reacts with a second reactant.

In an important application, the reactant material is a pathogen and absorption of one or more ultraviolet (UV) photons modifies the chemical structure of bio-molecules such as nucleic acids within the pathogen thereby inactivating the pathogen. The pathogen may be suspended as particles or droplets in air. The pathogen may be surrounded by a liquid solution, for example water and biological molecules. The pathogen may be attached to a surface, for example a food product.

The arrangement herein may provide one or more of the following features and objectives. A first objective of the present invention is to provide an energy efficient reaction system thereby reducing the cost of UV sterilization and photochemistry applications. A second objective of the present invention is to reduce the exposure time required for a given energy input. A further objective of the present invention is to provide a compact UV sterilization system for space sensitive applications. A particular objective is to provide a real-time UV sterilization system. There may be a net cost reduction because the reflective optics generally cost less than light sources, particularly in the UV spectral region, and further there may be a reduction in operating cost as less power is required for fewer light sources.

In the present invention the effective optical path length is multiplied by using highly reflective surfaces arranged to direct photons along a predetermined optical axis across the same reaction volume multiple times, thereby amplifying the probability that a photon will interact with a sample material. A reaction chamber may have a plurality of predetermined optical axes within the scope of the invention wherein the photon flux along a first optical axis is substantially independent of photon flux along a second optical axis: that is a photon associated with a first optical axis has a less than 10% probability of becoming associated with a second optical axis. For example, a first optical axis may be perpendicular to a second optical axis wherein the first and second optical axes contain a common sample interaction volume. A predetermined optical axis may consist of a sequence of segments wherein each segment has a different direction and wherein substantially all (>90%) of the photon flux in a first segment is transferred to the next segment in the sequence. The sequence of segments may for example form a closed loop with N segments wherein photon flux from the Nth segment is transferred to the first segment. Photon flux is added to the reaction chamber in the direction of an optical axis and preferably displaced from the optical axis. Photon flux emitted from a source located on an optical axis has a higher probability of being reflected back to the source and being absorbed than photon flux emitted from a source displaced from an optical axis. Conversely the probability that photon flux emitted from a source displaced from an optical axis escapes the optical axis increases with displacement from the optical axis. The inventors found that the optimal source placement for concave spherical end mirrors is a displacement of 0.62 times the mirror radius from the optical axis. Lesser or greater displacements ranging from zero (on axis) to greater than the mirror radius may be used, but are not optimal.

The arrangement herein is primarily concerned with a single straight optical axis between the reflective surfaces, but may use options such as multiple or bent paths. This makes the distinction between ray segments associated with each axis fuzzy. Below the recipe is to select the axis with the highest order parameter for a consecutive sequence of ray segments.

A reactive material moves on a path through the reaction volume, possibly entrained in a carrier fluid. The optical enhancement is limited only by the reflectivity of the reflective surfaces as the intensity of the reflected photons decreases as $I=R^N$, where I is the intensity, R is the reflection coefficient of the surface, and N is the number of reflections. The reflectivity depends on material properties of the reflecting surface and the angle of incidence. By directing photons along a predetermined optical axis, the reflectivity R can be maximized. The effective intensity is the sum of electromagnetic radiation intensities passing through the sample volume.

The electromagnetic radiation intensities may be modeled by a set of ray segments in a sequence wherein each ray segment has an origin vector, direction vector, polarization vector, and phase. The direction vector is in the direction of the Poynting vector and the polarization vector represents the electric field amplitude. The intensity, or equivalently number of photons passing through a test surface per unit time, is proportional to the electric field amplitude squared. The first ray segment in each sequence has a pre-set number of photons large enough that statistical fluctuations are insignificant. At each interaction with a sample material or surface, a new ray segment is generated with origin at the location of the sample material or surface intersection. Hence the length of each ray segment is the distance traveled from the point of origin to the point of interaction. In general, the direction and phase are changed and the amplitude is reduced with each interaction. Longer ray segments correspond to greater photon lifetimes for photons included in the segment amplitude and hence greater probability of interacting with sample material. Hence, the present invention statistically maximizes ray segment lengths by the arrangement of reflective surfaces (within system volume constraints).

The term ray path herein refers to the set of ray segments generated by one original ray. Each ray path may be traced until the intensity falls below a threshold value. Unless otherwise specified, the threshold value used herein is 0.0001 of original intensity. The optical path length for each ray path herein is defined as the sum of ray segment lengths for which the intensity is above the threshold.

The number of reflections herein refers to the number of ray segments in a ray path for which the intensity is above the threshold value.

The term amplification herein refers to the sum of ray segment intensities wherein the intensity of each ray segment included in the sum is above the threshold value. Theoretically the amplification for a closed chamber is given by $$A=1/(1-R)$$

where R is the reflectivity of the chamber walls. For a reflection coefficient of 0.90 typical of an aluminum mirror, the maximum theoretical enhancement is 10×. For a reflection coefficient of 0.9975 typical of a narrow band dielectric mirror the maximum theoretical enhancement is 400×. The theoretical limit is not realizable due to optical losses caused by necessary features such as light sources, absorption by the reactive material, carrier fluid, and ports for input and output of reactive material and carrier fluid. The present invention configures reflective surfaces to obtain a substantial fraction of the theoretical amplification limit.

The term segment moment herein refers to the product of the displacement vector (from the ray segment origin to the point of intersection with a surface) of a ray segment multiplied by the intensity of the segment. The segment moment is a more useful measure of photonic efficiency than amplification because the segment moment accounts for the photon lifetime. Useful statistics can be calculated by summing ray segment moment magnitudes and by summing ray segment moment component magnitudes wherein the ray segment moment components are projections of the ray segment moments onto axes parallel and perpendicular to a predetermined optical axis.

The order parameter S is a useful measure of the degree of alignment of ray segments with a predetermined optical axis. S is defined herein as $$S=<\tfrac{1}{2}(3\cos^2(q)-1)>$$

Where q is the angle between the direction vector of each ray segment and a predetermined optical axis and the angle brackets indicate an average over all ray segments. In an isotropic system, such as a chamber lined with a diffuse reflector S is close to zero, generally less than 0.1. In an anisotropic system such as a laser cavity S is close to one. A consecutive sequence of ray segments is associated with a predetermined first optical axis if the order parameter for said sequence is larger than the order parameter for any second predetermined optical axis.

The sample volume may be divided into sub volume elements and the radiation flux through each sub volume element may be calculated by summing the intensities of each ray segment weighted by the distance.

The reflective surfaces of the reaction chamber are collectively arranged to preferentially direct photon flux along a predetermined optical axis so as to increase the order parameter relative to said predetermined optical axis. For each optical axis the order parameter is at least 0.2. Preferably the order parameter is at least 0.5. Most preferably the order parameter is at least 0.8. Put another way, the moment relative to the optical axis is at least twice the moment of any axis perpendicular to the optical axis. Preferably the moment relative to the optical axis is at least five times the moment of any axis perpendicular to the optical axis.

Preferably the source of radiation is at least partially collimated and the at least partially collimated radiation is directed so as to preferentially propagate along a reaction chamber optical axis.

Preferably radiation enters the reaction chamber through an aperture wherein the aperture is sized and positioned to maximize the probability that photons emitted through the aperture are propagated a plurality of times along ray segments at least partially aligned with a predetermined optical axis minimize the probability that a photon emitted through said aperture is directed back into said aperture by reflective surfaces of the reaction chamber. These dual objectives are met by minimizing the aperture size and positioning the aperture axis parallel to and displaced from the predetermined optical axis.

Preferably the reflective surfaces of the reaction chamber are dielectric. Preferably each region of the dielectric surfaces is fabricated so as to maximize reflectivity for a selected range of wavelengths at a selected range of angles of incidence for each surface region wherein the orientation of each surface region (and hence angles of incidence) is selected to increase the order parameter for radiation propagated relative to a predetermined optical axis.

Due to the optical amplification, the required flux of photons required to deliver a given dose is reduced by the effective amplification factor, thereby reducing the cost of light sources required for a given reactive material throughput. The reduced cost of light sources is partially offset by the increased expense of highly reflective optical surfaces. Optical amplification may also be used to reduce the time required to carry out a photochemical reaction, for example the time required to sterilize a volume of fluid. Significantly, the present invention provides a means to sterilize air on a time scale comparable with human breathing enabling the deployment of re-useable masks to stop the spread of pandemic virus.

In accordance with an important feature of the invention, there is provided a reaction chamber, a source of electromagnetic radiation (EM) in communication with the reaction chamber, a reactant material, an input port, an output port, a plurality of flow paths between the input port and output port and a plurality of paths for EM radiation wherein at least one path for EM radiation includes at least two reflections from at least two reflective regions of the reaction chamber surface and wherein at least one EM radiation path intersects each flow path. The reactive material may be a fluid or entrained in a fluid. Preferably a majority of EM radiation paths include at least two reflections from reflective regions of the reaction chamber surface. Preferably a majority of EM radiation paths include at least ten reflections from reflective regions of the reaction chamber surface. Most preferably a majority of EM radiation paths include more than one hundred reflections from reflective regions of the reaction chamber surface.

The number of reflections is calculated as the number of times a ray is incident on and reflected from a reaction chamber surface with intensity greater than threshold intensity equal to 0.0001 of its initial intensity. There are two requirements: firstly that the path is within the reaction chamber and secondly that the intensity is greater than the threshold intensity. For purposes of this calculation a path that includes a ray that exits the reaction chamber and is reflected back into the reaction chamber is deemed to be within the reaction chamber. The reflection back into the reaction chamber is a feature of the invention. A path is terminated if a ray permanently exits the reaction chamber, for example through a port. Theoretically an EM wave can be reflected an infinite number of times between two surfaces. The sum of intensity for an infinite number of reflections is $1/(1-R)$ where R is the reflectivity. The threshold is chosen so that the calculated sum includes 99.99% of the intensity that would be calculated if the sum included an infinite number of terms. For surfaces with constant reflectivity R the number of reflections N is given by $N=\log(t)/\log(R)$. For example, for aluminum with average reflectivity of 92%, the number of reflections over the threshold is 110. For a dielectric mirror with reflectivity 99% the number of reflections over the threshold is 916. However, the reflectivity depends on the angle of incidence and polarization of the EM radiation which in general are different for each reflection from the reaction chamber surface. The reaction chamber is shaped to maximize the number of reflections with high reflectivity and to minimize the number of reflections with low (or zero) reflectivity.

Preferably the reflective regions of the reaction chamber surface reflect at least half of incident EM radiation. More preferably the reflective regions of the reaction chamber surface reflect at least 90% of incident EM radiation. More preferably the reflective regions of the reaction chamber surface reflect at least 99% of incident EM radiation. Most preferably the reflective regions of the reaction chamber surface reflect at least 99.9% of incident EM radiation. The reaction chamber is shaped and formed to maximize the number of EM radiation reflections and to maximize the number of times an EM radiation path intersects a flow path.

The EM radiation source may for example be a lamp filament, a laser, a gas vapor discharge tube, or a LED. The term "EM radiation source" includes the EM emitter and all circuitry and power supplies associated with and required for the emitter to operate. The EM radiation source may emit EM radiation over a range of similar wavelengths characterized by a central wavelength and a bandwidth. Unless explicitly stated otherwise, all references to an EM wavelength herein refer to a band of wavelengths labeled by the central wavelength of the band. Unless otherwise stated, the term "EM radiation" herein refers to electromagnetic radiation with wavelengths between 180 nm and 700 nm.

In an important embodiment, the EM radiation has wavelengths in the UVC range of 180 nm to 300 nm. For embodiments with wavelengths in the UVC range the term "sterilization chamber" may be used in place of, or interchangeably with the term "reaction chamber" to specify the intended operating wavelengths. The UV wavelength or wavelengths emitted into the sterilization chamber may vary according to the type of microorganism to be inactivated. The UV wavelengths may be chosen to correspond with absorption bands of the microorganism(s) to be inactivated. The UV wavelengths may be chosen to generate ozone or oxygen radicals that harm or damage the microorganism to be inactivated. The UV wavelength may for example be approximately 255 nm, known to be germicidal. The UV wavelength may for example be approximately 265 nm, known to be germicidal.

In accordance with an important optional feature of the invention which can be used independently with any of the above or following features, there is provided at least one region of the reaction chamber that reflects EM radiation specularly. The macroscopic angle of reflection is equal to the macroscopic angle of incidence. Specular reflection regions may for example be mirrors. The mirrors may for example be coated aluminum with typical reflectivity of approximately 95% in the UVC region. The mirrors may for example be dielectric mirrors with reflectivity over a bandwidth of 100 nm greater than 99%.

In accordance with an important optional feature of the invention which can be used independently with any of the above or following features, there is provided at least one region of the reaction chamber that absorbs EM radiation. Absorbing regions may be located proximate to the input port, the output port, or both. The absorbing regions function to prevent transmission of EM radiation from inside the reaction chamber to outside the reaction chamber.

In accordance with an important optional feature of the invention which can be used independently with any of the above or following features, there is provided at least one region of the reaction chamber that reflects at least a portion of EM radiation diffusely. For example, a mirror may include features that scatter radiation at non-specular angles. The features may for example be scratches or tooling marks that are deliberately retained for the purpose of reflecting a small percentage of incident radiation at non-specular angles. Diffuse reflectance regions may be used to homogenize the intensity of EM radiation within the reaction chamber.

In accordance with an important optional feature of the invention which can be used independently with any of the above or following features, there is provided a fluid flow chamber wherein the fluid flow chamber is comprised of a material that transmits EM radiation and wherein the fluid flow chamber is contained within the reaction chamber. The fluid flow chamber is formed and shaped to confine fluid flow to regions with high EM radiation field density. The fluid flow chamber may for example be comprised of quartz, sapphire, fused silica, or other UV transparent material.

In accordance with an important optional feature of the invention which can be used independently with any of the above or following features, there is provided a particulate filter. The particulate filter is operable to remove and retain particles with size greater than a threshold size from the fluid. The threshold size is selected to reduce accumulation of particles on reflective surfaces. The particulate filter may be proximate to the input port. The primary purpose of the particulate filter is to prevent fouling of reflective surfaces and consequent degradation of reflectivity.

In accordance with an important optional feature of the invention which can be used independently with any of the above or following features, there is provided a plurality of fluid flow chambers within the reaction chamber wherein each fluid flow chamber has input and output ports distinct from the input and output ports of another fluid flow chamber. For example, the sterilization chamber may be integral to a medical respirator wherein a first fluid flow chamber may be used to sterilize air inhaled and a second fluid flow chamber may be used to sterilize air exhaled.

In accordance with an important optional feature of the invention which can be used independently with any of the above or following features, there is provided a plurality of electrodes operable to generate an electric field within the sterilization chamber. The electric field may vary temporally and spatially within the chamber. The electric field is operable to orient molecules within reactive materials relative to the polarization of the EM radiation field at a location in the reaction chamber. EM radiation may become polarized after multiple reflections and the polarization may vary spatially within the reaction chamber. The purpose of the electric field is to preferentially orient a molecular transition dipole moment in the direction of EM polarization so as to increase the probability that a photon is absorbed by the molecule.

In accordance with an important optional feature of the invention which can be used independently with any of the above or following features, there is provided a fluid flow regulation means. The fluid flow regulation means may for example be a pump, fan, or valve that changes the rate of fluid flow through the reaction chamber.

In accordance with an important optional feature of the invention which can be used independently with any of the above or following features, there is provided a spectroscopy port integral to the reaction chamber. The spectroscopy port may include a radiation emitting device, a radiation receiving device and a radiation measuring device. The spectroscopy port may for example be used to provide information about the type and concentration of microorganisms present. The spectroscopy port may for example be used to provide information about the viability of microorganisms. The spectroscopy port may for example include an infrared spectrometer or a Raman spectrometer wherein the infrared or Raman spectrum provides a spectral fingerprint of microorganisms present. In one embodiment, the UV source excites a Raman spectrum and Raman scattered radiation is analyzed by a spectrometer. In another embodiment infrared radiation is reflected by reaction chamber surfaces a plurality of times to interact with a plurality of fluid flow locations and the infrared radiation is analyzed to provide information about a material in the flow. The material may for example be an exhaled metabolic product such as carbon dioxide, methane, ketones, aldehydes, alcohols, hydrocarbons and various volatile organic compounds (VOCs). The material may for example be a biological material. The information obtained can be used to control the various parameters of the process including intensity and flow rate.

In accordance with an important optional feature of the invention which can be used independently with any of the above or following features, there is provided a flow rate measurement means. The flow rate measurement means may for example be a flow meter.

In accordance with an important optional feature of the invention which can be used independently with any of the above or following features, there is provided a control means operable to change at least one operating parameter of the reaction chamber. The operating parameter may for example be the wavelength and/or intensity of EM radiation provided by the EM radiation source. The operating parameter may for example be the fluid flow rate through the reaction chamber. The operating parameter may for example be the electric field generated at a location in the reaction chamber.

In an embodiment that may be used in combination with any of the preceding or following embodiments, the reaction chamber has the general shape of a confocal cavity wherein light may be reflected between opposing surfaces an infinite number of times suffering losses only due to absorption.

In an embodiment that may be used in combination with any of the preceding or following embodiments, the reaction chamber has the general shape of a White cell, differing from a White cell insofar as no optical output port is provided and is instead replaced with a reflective surface.

In an embodiment that may be used in combination with any of the preceding or following embodiments, the reaction chamber has the general shape of a Herriott cell, differing from a Herriott cell insofar as no optical output port is provided and is instead replaced with a reflective surface.

In an embodiment that may be used in combination with any of the preceding or following embodiments, the reaction chamber has the general shape of a circular multipass cell, differing from a circular multipass cell insofar as no optical output port is provided and is instead replaced with a reflective surface.

The term "apparatus" is used herein to refer to the reaction/sterilization chamber and all associated structures.

In an embodiment that may be used in combination with any of the preceding or following embodiments, the reaction chamber functions as a sterilization apparatus is used to neutralize or deactivate an infectious agent wherein the infectious agent is a prion, virus, bacteria, fungi, protozoan, helminth, yeast, or biological warfare agent. In some embodiments the sterilization apparatus neutralizes or deactivates infectious agents in air, for example in a HVAC system for a building. In some embodiments the sterilization apparatus neutralizes or deactivates infectious agents in water, for example in a municipal drinking water system or in a municipal wastewater treatment system. In some embodiments the sterilization apparatus neutralizes or deactivates infectious agents in a cryogenic fluid, for example in tissue bank, culture bank, or blood bank stored under liquid nitrogen.

In an embodiment that may be used in combination with any of the preceding or following embodiments, the reaction apparatus is used to neutralize or deactivate a chemical agent. The chemical agent may for example be a toxin such as an insecticide, fungicide, or herbicide that is sprayed for agricultural use. The chemical agent may for example be a chemical warfare agent. The reaction apparatus processes air to limit human exposure to the toxin. The reaction apparatus may neutralize or deactivate chemical agents by photo-disintegration or by photo-catalysis of a reaction that destroys the chemical agent. The wavelength of EM radiation is adjusted to maximize absorption by the chemical agent.

In an embodiment that may be used in combination with any of the preceding or following embodiments, the reflective surfaces of the reaction chamber are formed and shaped such that the intensity of EM radiation at a location in the reaction chamber is at least in part proportional to the fluid flow rate at that location. In a related embodiment, the reflective surfaces of the reaction chamber are formed and shaped such that the EM radiation dose received by a fluid element integrated over each fluid flow path is greater than a required dose threshold. The density of EM radiation (photons per unit volume) at a location along a fluid flow path may be increased by angling a reflective surface to reflect EM radiation along a path through the fluid flow location.

In an embodiment that may be used in combination with any of the preceding or following embodiments, the control means determines the time a fluid element spends at each location along a fluid path and adjusts the intensity of EM radiation such that the integrated intensity of EM radiation received along the fluid flow path is greater than a threshold required dose. This embodiment is useful in applications with a temporally varying flow rate.

In an embodiment that may be used in combination with any of the preceding or following embodiments, the control means determines a type of microorganism present in a fluid element and adjusts the intensity of UV radiation such that the integrated intensity of UV radiation received along the fluid flow path is greater than a threshold required dose for said microorganism type. The control means may for example determine a type of microorganism by comparing the infrared or Raman spectrum of a fluid element with a spectral database.

In an embodiment that may be used in combination with any of the preceding or following embodiments, the fluid entering the reaction chamber at the input port is a liquid. The liquid may for example be water or a water solution. The liquid may for example be solvent containing monomers that are polymerized by a photochemical reaction.

In an embodiment that may be used in combination with any of the preceding or following embodiments, a micro-fluidic array is integral to the reaction chamber. The micro-fluidic channels may for example be used to produce pharmaceutical products such as anti-malaria drug Artemisinin via photochemical reactions. In some embodiments a plurality of different reactant materials flow along different micro-fluidic channels, are converted into intermediate products by photochemical reactions, and the plurality of intermediate products are combined to form a final product in a final photochemical reaction.

In an embodiment that may be used in combination with any of the preceding or following embodiments, the sterilization apparatus may be integral with drinking water infrastructure such as a municipal water treatment plant. The sterilization apparatus may for example be used in a municipal water treatment plant. The multiple reflection arrangement of the sterilization apparatus reduces the amount of UV radiation required, and hence the electric power requirement resulting in lower operating cost. The sterilization apparatus may for example be integral with or in line with a drinking water outlet in a commercial or residential building. The sterilization apparatus for drinking water application may replace or supplement filters that are prone to development of bacteria biofilms. The sterilization apparatus may for example be used with a portable water supply wherein the fluid flow path is a reservoir of disinfected water. The fluid flow path may for example hold one liter of water and UV radiation is supplied for a disinfection period wherein the disinfection period is found by experiment to be effective. The sterilization apparatus may be used for example to provide a laboratory with sterile water wherein the water is sterilized immediately before use.

In an embodiment that may be used in combination with any of the preceding or following embodiments, the fluid entering the sterilization chamber at the input port is a gas. The gas may for example be air.

In an embodiment that may be used in combination with any of the preceding or following embodiments, the sterilization apparatus is integral with a face mask. The face mask includes an air chamber proximate to the nose and mouth. The air chamber may be comprised of a transparent material. The air chamber may be sealed to the face with a soft compliant gasket material. The air chamber may be connected with one or more ports of a sterilization chamber. In one embodiment, air is inhaled and exhaled through the same port. In a second embodiment, air is inhaled through a port connected with a sterilization chamber and exhaled through a flap valve in the air chamber opened by positive air pressure. In a third embodiment, air is inhaled through a port connected with a first fluid flow path through the sterilization chamber and air is exhaled through a port connected with a second fluid flow path through the sterilization chamber. In some embodiments the fluid flow paths may be removed for cleaning or replacement.

In an embodiment that may be used in combination with any of the preceding or following embodiments, the sterilization apparatus is integral with a medical respirator. In this embodiment, inhaled and exhaled air is sterilized to prevent cross contamination. Preferably at least one property of the exhaled air is measured to provide information about a health condition. The property may be measured for example with the spectrometer port.

In an embodiment that may be used in combination with any of the preceding or following embodiments, the sterilization apparatus is integral with a portable air cleaning unit. In this embodiment air is drawn into the portable unit with a fan, passes through the sterilization apparatus, and is discharged. The portable unit may be used for example to reduce the concentration of an infectious agent such as a virus in a room. The portable unit may for example be operated in a room occupied by a person infected with a virus to reduce the risk of infection spreading through air to adjacent rooms. The portable unit may for example be integrated into a dental evacuator proximate to a patient's face to collect and sterilize air exhaled by the patient during dental procedures.

In an embodiment that may be used in combination with any of the preceding or following embodiments, the sterilization apparatus is integral with the air distribution system of a vehicle. For example, the sterilization apparatus may provide a stream of sterilized air to each passenger in a car, bus, ship, or airplane. For example, the sterilization apparatus may accept air drawn from the immediate vicinity of each passenger in a car, bus, ship, or airplane.

In an embodiment that may be used in combination with any of the preceding or following embodiments, the sterilization apparatus is integral with the heating and ventilation system of a building. The sterilization apparatus may for example be integral to a central heating and air conditioning plant. The sterilization apparatus may for example be integral with ducts supplying each room or region thereof. The sterilization apparatus may for example be integral with the air supply of an elevator. The sterilization apparatus may for example be integral with a ducts supplying each cubicle in an office. The sterilization apparatus may also be used in the HVAC systems supplying sterilized air to clean rooms and labs. For example, sterile air is required to prevent microbial contamination in processes that are sensitive to microbial contamination such as pharmaceutical, biologic, medical device production and packaging as well as diagnostic procedures and microbiology experiments. The sterilization apparatus may also for example be integrated into a biocontainment lab or biocontainment chamber to disinfect air leaving the biocontainment area.

In an embodiment that may be used in combination with any of the preceding or following embodiments, the reactive material is the surface of a solid object that is passed through the reaction chamber. The solid object may for example fall under the influence of gravity through a reaction chamber without contacting the reaction chamber walls. The solid object may for example be entrained in a fluid flow. The solid object may for example be a polymer block wherein the surface is activated for a subsequent reaction by irradiation with electromagnetic radiation. The solid object may for example be a surgical instrument, medical device or personal protective equipment that is sterilized by irradiation with UVC radiation. The solid object may for example be a food object such as a chicken breast with *Salmonella* inactivated by irradiation with UVC radiation. The solid object may for example be a container used to package a medical device, pharmaceutical, or food product. The solid object may for example be a package for a consumer product irradiated in the reaction chamber with UVC radiation to prevent the transmission of an infectious agent by postal or courier delivery.

BRIEF DESCRIPTION OF THE DRAWINGS

FIG. 3A is a cross sectional view of an arrangement according to the present invention for use in a water sterilization reactor.

FIG. 3B is an axial view of the water sterilization reactor of FIG. 3A.

FIG. 15 shows a cross-sectional view of a deformable mirror according to the present invention.

FIG. 15A shows cross-sectional view of one mirror component of the arrangement of FIG. 15.

FIG. 15B shows a schematic cross-sectional view of a deformable scale mirror array according to the present invention.

FIG. 15C shows cross-sectional view of one mirror component of the arrangement of FIG. 15B.

FIG. 15D is a schematic cross-sectional view of a deformable mirror comprised on an ordered array of mirrors according to the present invention.

FIG. 15E shows cross-sectional view of one mirror component of the arrangement of FIG. 15A.

FIGS. 18A, 18B and 18C show intensity sequences of slices through the reaction chamber of FIG. 17A perpendicular to the chamber axis.

DETAILED DESCRIPTION

Embodiments of the present disclosure are described in detail with reference to the accompanying drawings. Detailed descriptions of constructions or processes known in the art may be omitted to avoid obscuring the subject matter of the present disclosure. Further in the following description of the present disclosure, various specific definitions found in the following description are provided to give a general understanding of the present disclosure, and it is apparent to those skilled in the art that the present disclosure can be implemented without such definitions.

Figure 1:
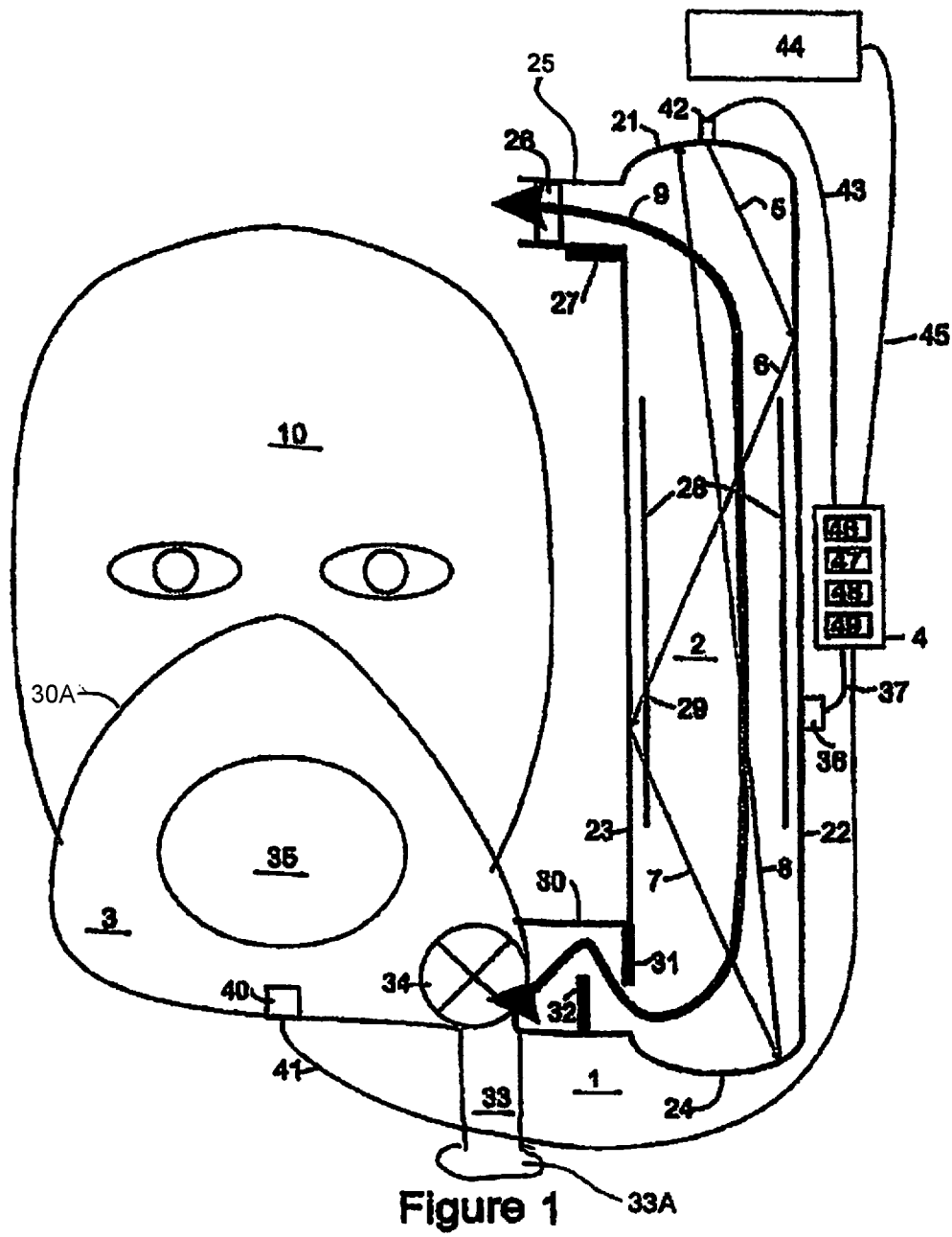
FIG. 1 is a schematic illustration of an arrangement according to the present invention for use in an air disinfection system for a face mask.

FIG. 1 shows schematic view of a portable arrangement generally indicated at 1 for sterilizing air supplied to a face mask. The major components are sterilization chamber 2, face mask 3, and control 4.

Sterilization chamber 2 includes input port 25 and output port 30. On inhalation, air is drawn through input port 25 through particulate filter 26 along the path indicated at 9. A particulate filter 26 operates to remove dust from the incoming air to prevent fouling of optical surfaces within the sterilization chamber. The filter mesh of the filter 26 is selected to remove most dust without unduly restricting air flow. As indicated at 27, surfaces proximate to the input and output ports may be comprised of a material that absorbs ultraviolet light. As indicated at 31 and 32 one or both of the input and output ports may include a sequence of baffles forming a tortuous path to prevent direct transmission of ultraviolet radiation through the port and outside the sterilization chamber. Preferably baffles 31 and 32 have reflective surfaces and are shaped to reflect incident radiation back into reaction chamber 2. It will be noted that in order to improve the efficiency of reflection, the inlet and outlet ports are not on an axis of symmetry of the reaction chamber.

As shown, the output port 30 includes a valve 34 that passes air from the port 30 and chamber 2 into facemask 3 on inhalation and directs exhaled air from the facemask to an exhaust 33 on exhalation. However, in a preferred embodiment, the valve 34 and exhaust 33 are omitted and exhaled air passes in reverse path through sterilization chamber 2 so as to be sterilized both in inhale and exhale both directions.

Sterilization chamber 2 includes an ultraviolet source 42 which may be a discharge lamp or a LED with peak emission between 200 nm and 410 nm. The ultraviolet source may for example be a LED with peak emission at about 255 nm available from Seoul Viosys. Ultraviolet rays are emitted from source 42 over a range of angles (not shown) into the sterilization chamber 2. Preferably the ultraviolet source 42 includes an integral optical element that reduces the angular divergence of emitted radiation. Preferably the angular divergence half angle is 30 degrees or less. Most preferably the angular divergence half angle is 3 degrees or less. An example ultraviolet ray is shown at 5, which is incident on reflective surface 22 and reflected toward reflective surface 23 as indicated as ray 6. The sterilization chamber may include a transparent tube 28 that guides air flow 9 to pass through regions of the sterilization chamber 2 with ultraviolet flux higher than a threshold flux. As shown schematically the tube forms a straight duct guiding the air flow. In some embodiments (not shown) the transparent tube can form other complex shapes such as a helix so as to form a coiled tube passing through the ultraviolet radiation field within the sterilization chamber a plurality of times. As shown the ray 6 passes through the transparent tube 28 as indicated at 29 and is reflected specularly by reflective wall 23 as shown at ray 7. Ray 7 is reflected specularly and focused by end face 24 toward end face 21 as shown at ray 8. The ultraviolet ray path indicated at 5, 6, 7, and 8 will in general include N reflections where N is greater than 2, limited only by the surface reflectivity and optical losses at ports and the ultraviolet source. With average reflectivity of 95% and neglecting port losses, the ultraviolet flux density is increased by a factor of 20. With average reflectivity of 99% and neglecting port losses, the ultraviolet flux density is increased by a factor of 100. Transparent tube 28 acts to confine the material to be treated within the tube path so that material passing through the tube passes through a sequence of regions of the radiation field that deliver an integrated radiation dose higher than a predetermined minimum dose. The tube path for example can be located in an area where the flux density is higher than or more homogeneous than regions exterior to the tube within the remainder of the chamber.

While the concave reflective surfaces 21 and 24 are shown of the same shape and diameter, this is not required. One of the surfaces can be flat or of a different profile from the other. The surfaces can be of different shapes and diameters to match the profile of a contained into which they are inserted. Thus for example in a water container or bottle a larger end may have a larger surface and an opposed end be smaller Control 4 receives electrical power from battery 44 through cable 45. When activated by switch 46, electrical power energizes ultraviolet source 42 via cable 43. As shown, the ultraviolet flux in sterilization chamber 2 is measured by optional detector 36 in communication with control 4 via cable 37. The measured flux may be logged to provide a record of functionality. In critical applications, the sterilization chamber may include redundant power supplies and ultraviolet sources (not shown). If the ultraviolet flux exceeds a threshold, indicator 47 is activated. Indicator 47 may for example be a green or blue LED or other visual indicator. Facemask 3 as shown includes optional microphone 40 in communication with control 4 via cable 41. Audio signals from microphone 40 may be broadcast by speaker 48 or wireless transmitter 49 to facilitate communication. In some embodiments, a smart phone may perform some or all of the control functions.

As shown, facemask 3 covers the nose and mouth region of human face 10. Facemask 3 is comprised of impermeable frame material 30A that conforms to the face preventing air exchange except through sterilization chamber 2. Preferably the impermeable material is transparent. The facemask frame may support a membrane region 35 thin enough to transmit human audio communications.

In some embodiments of the mask arrangement of FIG. 1, valve 33 directs exhaled air into a bladder shown schematically at 33A and the bladder when filled vents air at a controlled rate into the interaction volume 2. The bladder is useful for catching the excess volume of a cough or sneeze and directing the excess volume through the sterilization volume 2 at a controlled rate such that complete sterilization is achieved.

In some embodiments of the mask arrangement of FIG. 1, the inner surface of the mask 3 is lined with layers of a disposable absorbent material (not shown). The absorbent material may catch mucus and saliva from a cough or sneeze. The absorbent layer may be removed to present a clean surface to the mask wearer.

In some embodiments of the mask arrangement of FIG. 1, the mask is carried on a strap, so as to be readily available but not in place on the face, and brought to cover the face by the user only when a cough or sneeze is imminent. In this embodiment, the radiation source amplitude is increased relative to the amplitude required for normal breathing. The air velocity associated with a cough or sneeze is higher that the air velocity associated with normal breathing. In some embodiments the length of the optical cavity is increased by the ratio of air velocities to equalize the residence times of air volume elements in the normal breathing and cough/sneeze cases.

In some embodiments of the mask arrangement of FIG. 1, a sensor detects the increase in air pressure within the mask associated with a cough or sneeze and the amplitude of the radiation field is increased.

Figure 2:
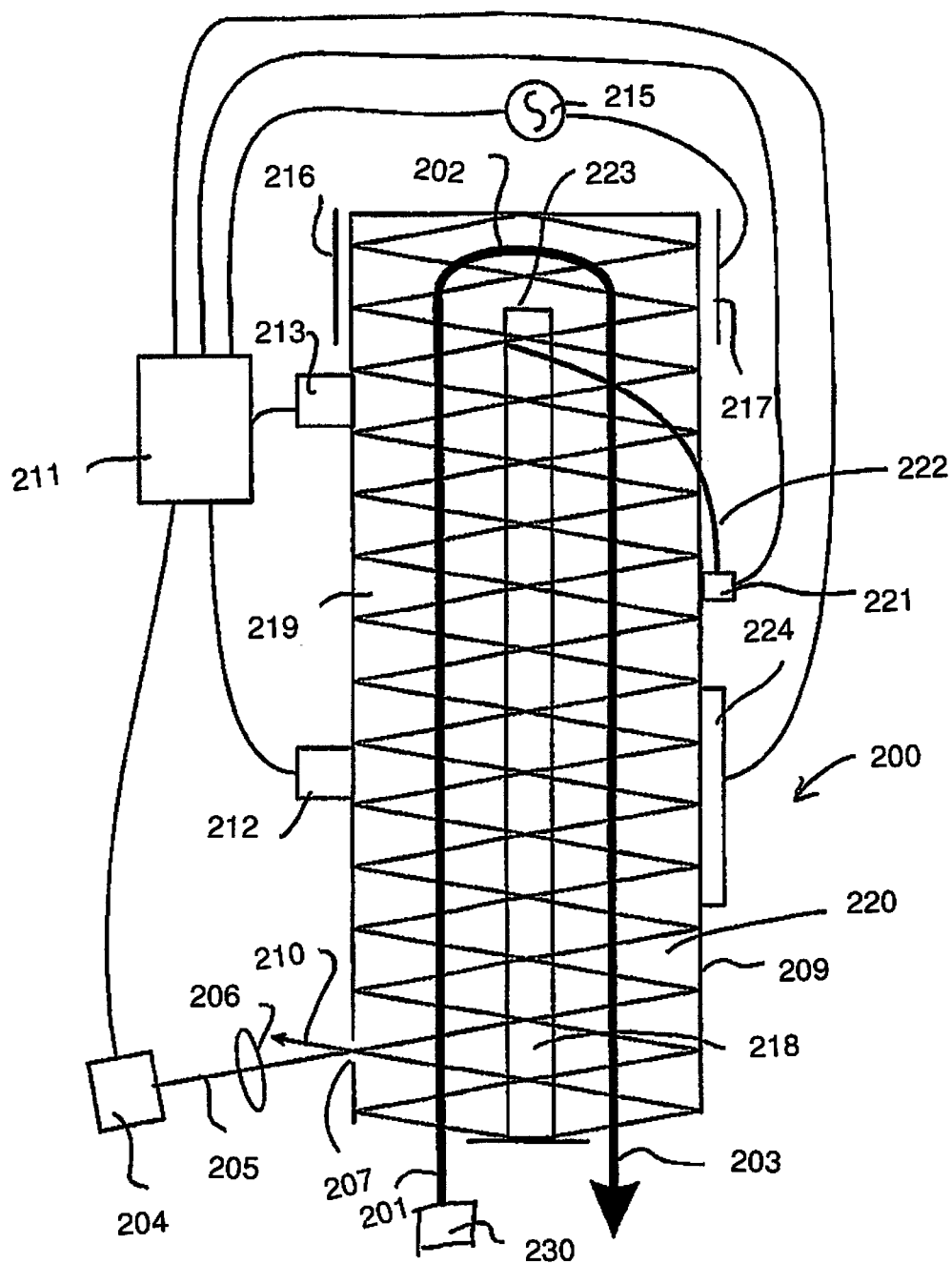
FIG. 2 is a schematic illustration of an arrangement according to the present invention for use in a photochemistry reactor.

In some embodiments of the mask arrangement of FIG. 1, the chamber 2 is divided, similarly to that in FIG. 2, by a longitudinally extending transparent divider so that the air path is doubled in length.

FIG. 2 is a schematic representation of a photochemistry reactor generally indicated at 200. Reactive materials enter the reactor chamber at 201 and follow the path indicated at 202 and exit as products at 203. The reactive materials may for example be an odor molecule, a fat molecule by interaction with electromagnetic radiation. The reactive material may for example be pharmaceutical precursors that are assembled into pharmaceutical molecules in a photochemical reaction. The reactive material may for example be waste water that is converted to clean water by photochemical reactions. The reactive material may include a catalyst that is activated by absorption of photons, or that acts with an activated reactant. The reactive material may include sensitizer molecules that absorb electromagnetic radiation and transfer a part of the energy absorbed to a second reactant. The reactive material may include an electron donor acceptor that participates in a REDOX reaction.

A first source of electromagnetic radiation is indicated at 204 external to the reaction chamber. Electromagnetic radiation 205 is focused by an optical system 206 through aperture 207 into reaction chamber 208. The walls 209 of the reaction chamber 208 [209] are highly reflective causing the electromagnetic radiation to reflect between reactor walls as indicated. The radiation that does not interact with a reactive material or the reactor walls exits at ray 210. The amplitude of the electromagnetic radiation at ray 210 is a small fraction of the input amplitude in ray 205 at opening 207, generally less than 1%: that is the number of reflections is set such that virtually all of the electromagnetic radiation is available to, and used by, the photochemical reactions.

Light source 204 is in communication with control 211, which regulates the amplitude of output light from the source to meet the requirements of a photochemical reaction. The photochemical reactions are monitored by an infrared spectrometer 212 and a Raman spectrometer 213 located to measure different stages of a photochemical process. Both spectrometers are in communication with the control 211.

Control 211 may adjust the flow rate of reactive materials by operating a flow rate control 230 and the amplitude of electromagnetic radiation from the source 204 according to feedback from the spectrometers.

Control 211 is connected with a voltage source 215 operable to produce a voltage between electrodes 216 and 217. The voltage difference generates a electric field that may be used to align reactive molecules relative to the electromagnetic radiation field. The flow in reactor 200 is guided by a block of transparent material 218 that divides the flow into an upper channel 219 and a lower channel 220. The transparent block transmits more than 90% and preferably more than 99% of incident electromagnetic radiation.

A second source of electromagnetic radiation is indicated at 221 in communication with control 211. Electromagnetic radiation may be coupled into a light pipe 222 and guided to a location 223 proximate to a photochemical reaction that utilizes the waveband generated by source 221.

A third source of electromagnetic radiation indicated at 224 is an array of LED light sources integral with an interior wall of the reaction chamber surface. The LED light sources are in communication with control 211 and may be activated individually to produce different wavelengths. Alternately the LED light sources 224 may produce the same waveband and the array increases the total photonic output. Individual LED's of the array may be distributed to different regions of the photochemistry reactor.

FIG. 3B shows a water sterilization reactor generally indicated at 300. Water to be treated is pumped into reactor 300 by pump 301 at inlet 302 and follows path 303 to outlet 304 with flow meter 305 measuring the flow rate. Control is in communication with pump 301 via cable 307 and flow meter 305 via cable 308. Water flows in channel 309 with transparent wall 310. The channel 309 may for example be fabricated with quartz or fused silica. As best seen in cross section in FIG. 3A, discharge lamps 311, 312, 313, 314, and 315 are arranged symmetrically about water channel 309 and have reflectors 316 shaped to direct UVC radiation toward water channel 309. The reflectors 316 may have a circular or parabolic cross section to reflect UVC radiation toward channel 309 in a direction generally perpendicular to the axis of 309 as shown at 317.

Figure 4:
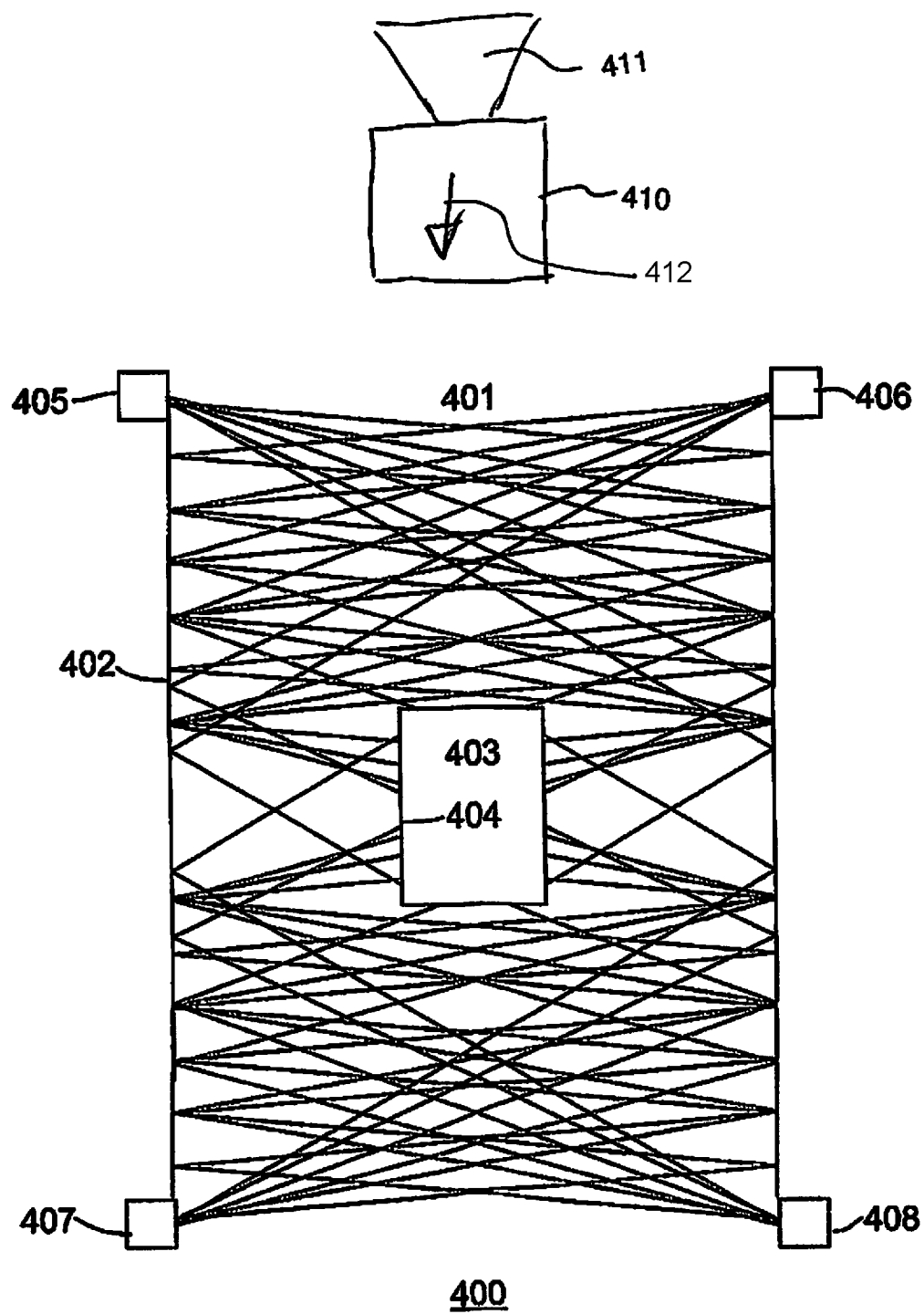
FIG. 4 is a schematic illustration of an arrangement according to the present invention for use in irradiation of solid objects.

In FIG. 4 is shown an arrangement 400 for treating solid bodies 403 such as a chicken breast where bacteria and other pathogens on an outer surface 404 are required to be disinfected or such as a body within a manufacturing process where an exterior coating on the exterior surface is required to be activated. These are only examples and many other uses of the system can be found. In this arrangement a duct 402 confines the bodies to pass along a path through the duct. A number of UV sources 405, 406, are provided at either side of an inlet 401 and two further sources 407 and 408 are located at an outlet. The sources all are arranged to direct the UV rays into the interior so as to pass across the duct to an opposed side for multiple reflections back and forth. The body is thus irradiated from each side and with a substantially homogeneous flux intensity.

In FIG. 4, the objects 403 to be sterilized can be carried on a suitable support such as a conveyor. However in one preferred arrangement, there is provided a singulation system 410 for singulating the particles from a source 411 into a stream 412 of the particles arranged in a spaced row of the particles.

Figure 5:
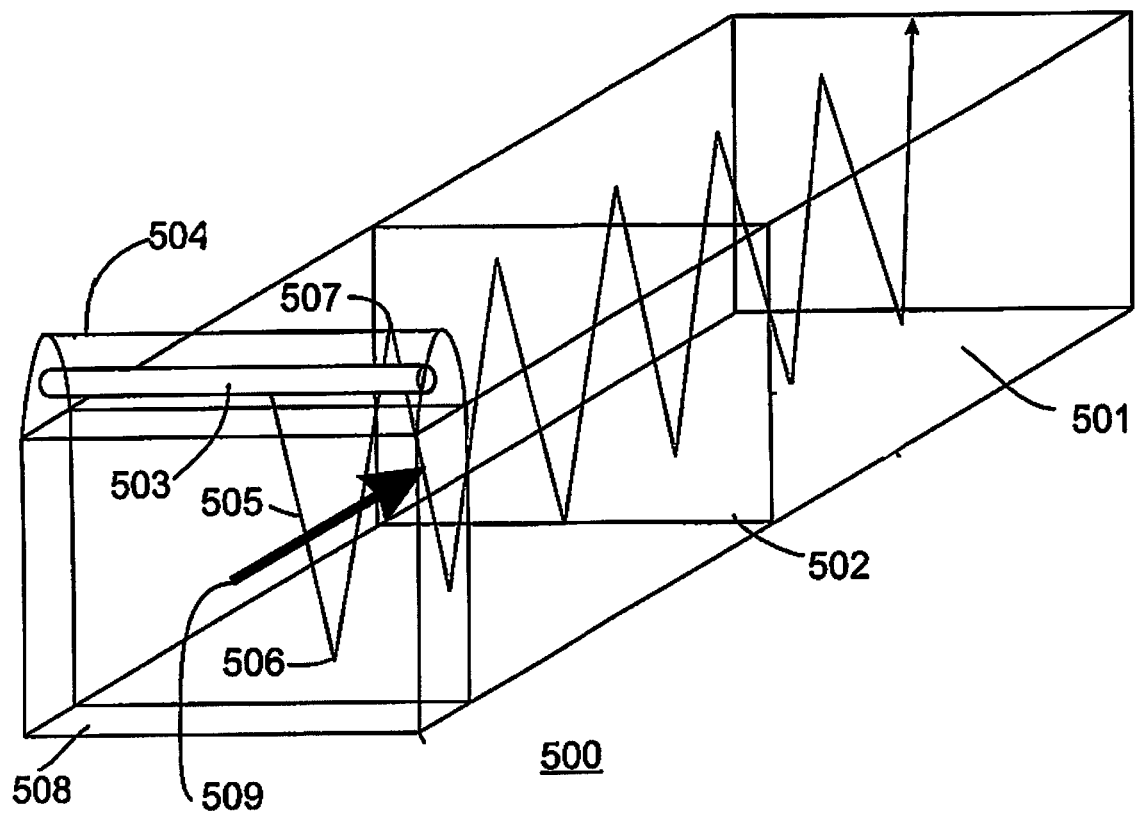
FIG. 5 is a schematic illustration of an arrangement according to the present invention for use in sanitizing air flow in an air duct of a HVAC system.

Preferably the particles are singulated by passing through at least one duct carried on a rotating member so that centrifugal forces generated by rotation of the rotating member overcome frictional forces between the particles and the duct to cause acceleration and separation of the particles in the duct. An arrangement of this type is shown in PCT Publication 2018/018155 published 1 Feb. 2018 by the present inventors, the disclosure of which is incorporated herein by reference or may be referenced for further detail of the rotating body and separation ducts. In this arrangement the duct 402 may form one of the ducts on the rotating body. The singulation of the particles causes them to be separated each from the next in an aligned row so that each is accessible relative to the next to allow the photons from the reflected beams to access each without interference from the others. Also the arrangement shown in this publication provides the ability to rotate the particles both to align their longitudinal axis if they are elongate and to rotate them about the axis. In this way the singulation and orientation provided by this system or by other similar systems allows all faces of the particles to be impacted by the radiation and properly sterilized In FIG. 5 is shown an arrangement 500 using an air duct 501 defined by walls 502 forming a rectangular construction. A fan 508 is mounted at a suitable location in the system so as to drive air through the duct along the path 509. A source 503 of UV light is mounted in a parabolic reflector 504 powered by a power source and controlled by a control system as previously described. The elongate source lies across the duct and generates rays 505 which reflect back and forth from the walls parallel to the source in the manner previously described. This can be used to reduce the number of pathogens within the duct by the interaction with the UV light. Absorption materials and labyrinth seals previously described can be used to prevent escape of the UV rays.

Figures 6, 6A:
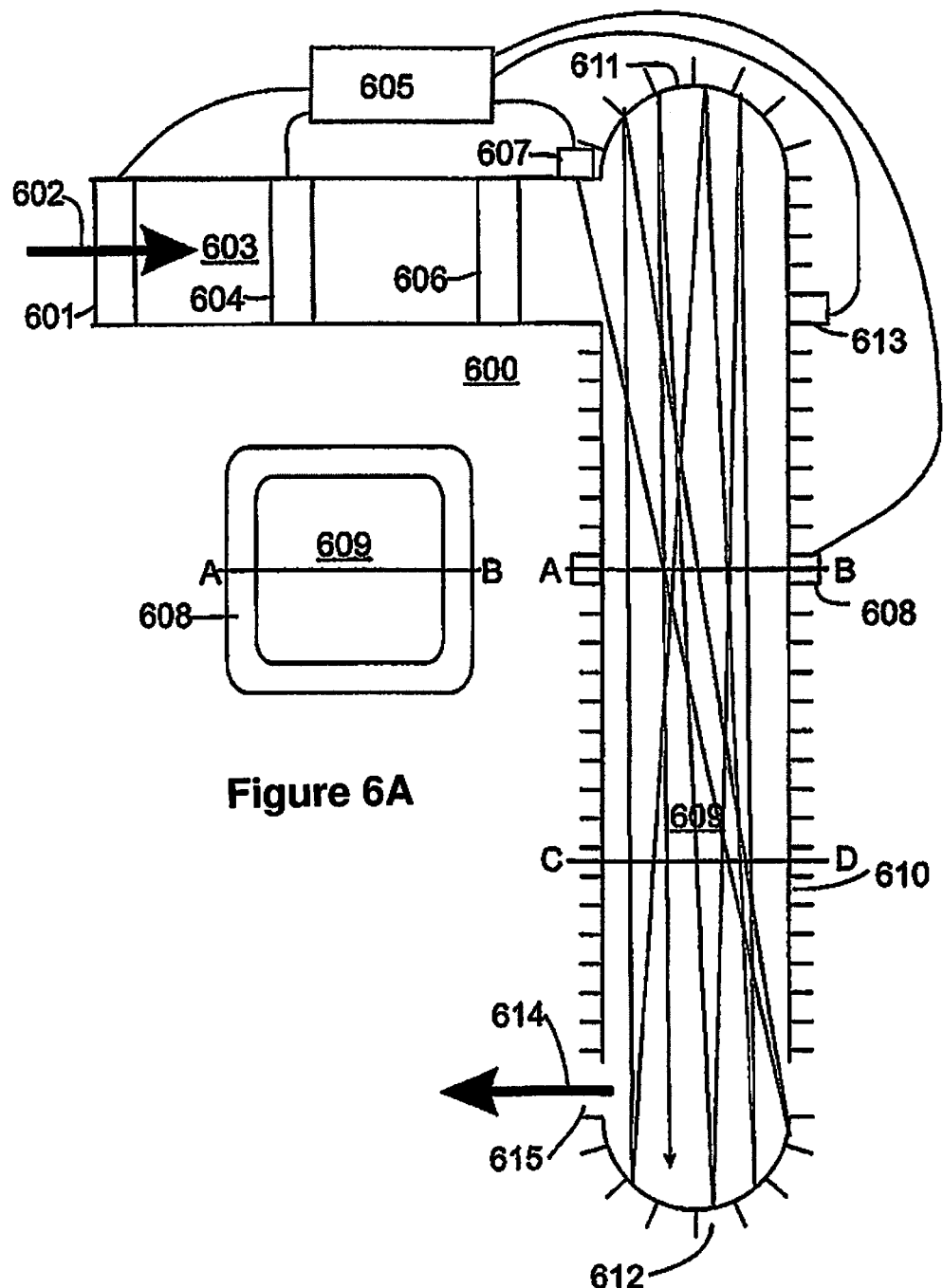
FIG. 6 is a schematic illustration of an arrangement according to the present invention for use in treatment of a fluid.
FIG. 6A is a cross-section along the lines A-B of FIG. 6.

In FIG. 6 is shown an arrangement 600 for treating a fluid such as air in which the fluid is fed along a path 602 in a duct 603 driven by a fan 601. A flow meter 604 detects the rate of flow which can be used to control the treatment system at a controller 605. A particle filter 606 extracts particles to reduce contamination of the reactor. The reactor 609 is formed of a cylindrical wall 610 capped at its ends by hemispherical end walls 611 and 612. The end caps are preferably formed of a dielectric mirror. The cylindrical tube may be a dielectric mirror or a reflective metal of lower reflectivity than the dielectric end mirrors. The source 607 directs UV rays into the reactor at the junction between the duct 603 and the reactor. The reactor has an outlet 615 at which the stream of fluid 614 escapes with the outlet and inlet being arranged symmetrically on one side of the center line of the reactor so that they do not interfere with the reflectivity which is primarily longitudinal of the reactor between the end caps. A sensor 613 is mounted on the side wall of the reactor to detect one or more conditions within the reactor so as to apply control to the light source or sources by the controller 605. An additional annular source is located around the side wall of the reactor as shown in FIG. 6A to supplement the UV light and to form rays which reflect back and between the side walls.

While the end caps 611 and 612 are shown as being hemispherical in shape, parabolic cross-sections can be used.

In some cases, the source can be located at an aperture at a position between the center and periphery of one end cap. However, the source is in some embodiments advantageously located at the edge of one end cap since this requires that the beam is directed inwardly toward the center axis connecting the two end caps. This causes the locus of the reflections to lie on a spiral at each end cap moving from the edge closer to the center axis and this can provide a better coverage by the beams within the cylindrical volume defined by the reflected beams.

In another arrangement, the wall 610 can be curved along its length so that its diameter at the center is larger or smaller than its diameter at the end caps. In this way the beams escaping from the cylinder defined by the end caps impacts the wall at an angle of incidence which can be adjusted by the amount of curvature and the direction of curvature. This change in the angle of incidence can be used or tailored relative to the reflective character of the wall to maximize the reflections and reduce the losses. The wall 610 can be cylindrical or be formed of flat panels to define a polygon.

The chamber into which the fluid is injected as shown in FIG. 6 can contain devices for fluid disturbance such as impellers or guide surfaces which direct the fluid into a path to increase interaction with the radiation. The flow can thus be condoled or turbulent to obtain the best interaction. Such devices can be located at spaced positions along the duct. The entrance and exit ports can communicate with a surrounding ring to allow escape around the full periphery of the chamber and connection to a single port connected to the ring.

When used with liquid, for example for sterilizing water, the chamber can be arranged so that it is fully filled by gravity by the entering liquid so as to avoid liquid surfaces within the chamber which can interfere with the radiation paths and cause unsuitable or less efficient reflections. In this way, entry at the bottom and discharge from an exit duct above the top reflective surface is preferred to that the chamber is filled up to and above the top reflective surface.

Figure 7:
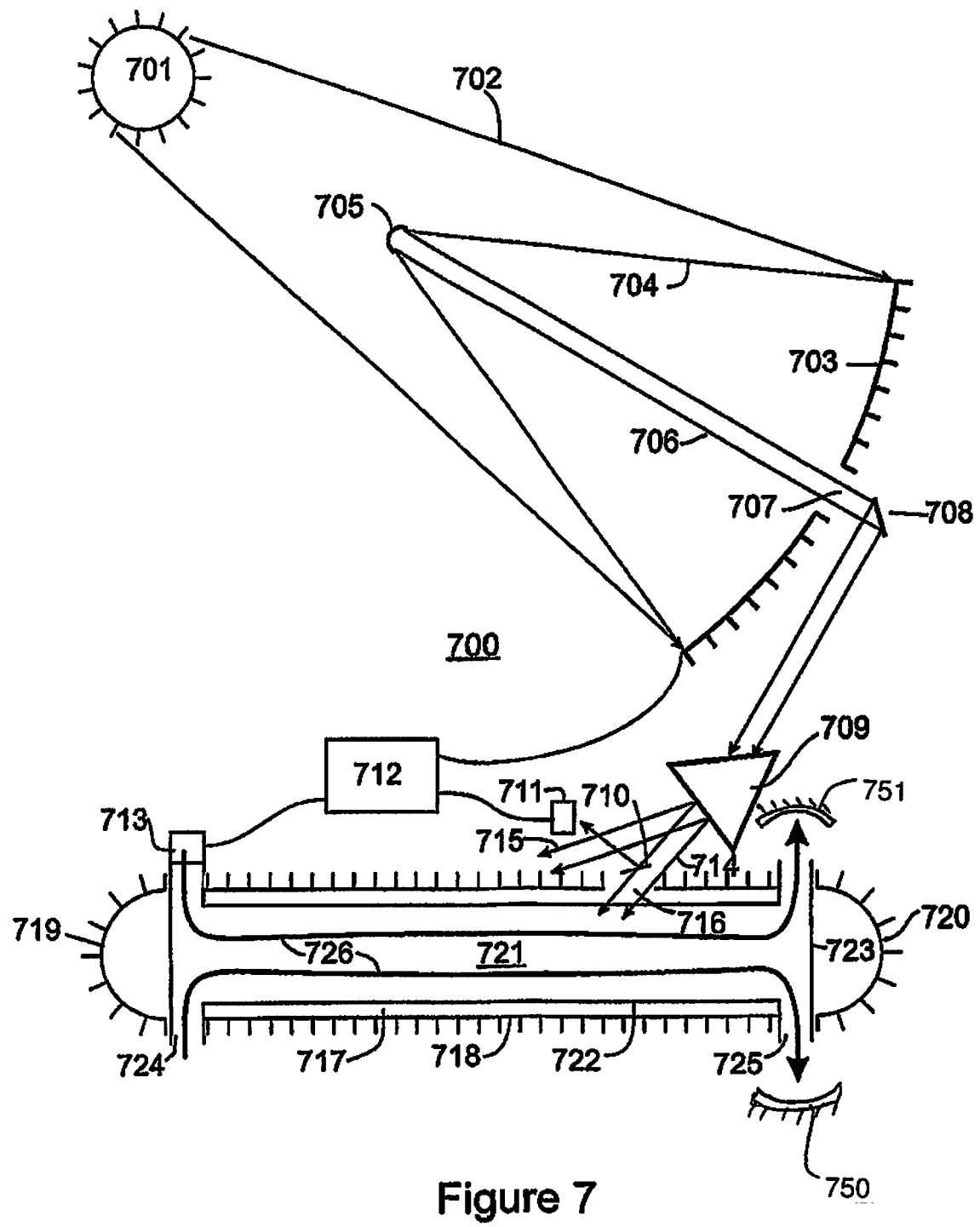
FIG. 7 is a schematic illustration of an arrangement according to the present invention for use in treatment of a water supply.

FIG. 7 shows a water treatment system generally indicated at 700. An external light source 701 emits electromagnetic rays 702 that are incident on a reflective collector 703. The external light source may be the sun. In an alternate arrangement (not shown) the external light source is a discharge tube, filament, or LED. The reflective collector 703 has a convex shape that focuses reflected electromagnetic radiation 704 at collimator mirror 705 to produce collimated beam 706. The convex shape may for example be parabolic or spherical. The combination of collector 703, collimator 705 and aperture 707 may be a Cassegrain reflector or a functional equivalent. Control in communication with reflective collector 703 may transmit codes to motors (not shown) that orient collector 703 relative to the sun to maximize solar radiation collected. Collimated beam 706 passes through aperture 707 to steering mirror 708 and is directed to wavelength separator 709 that directs different wavelength along different paths as indicated at 714 and 715. As shown rays 714 with selected wavelengths pass through slit 716 and enter optical cavity 717. A reflective surface 710 reflects a small constant fraction of selected wavelengths to detector 711 in communication with control 712. The reflection at surface 710 may for example be Fresnel reflection from a glass surface or a polka dot reflector. Detector 711 may be a photodiode and associated circuits that transmit a voltage proportional to irradiation to control 712. Control 712 integrates the irradiation over time to calculate a radiation dose in optical cavity 717. Control 712 is in communication with flow regulator 713 and adjusts the flow rate such that each volume element of water receives at least a threshold dose of radiation. Water to be treated enters at port 724, flows through transparent channel 721 and exits at port 725 as indicated by flow line 726. The transparent channel walls 722 may be fabricated from quartz, sapphire, fused silica or other UV transparent material. Optical cavity 717 is comprised of reflective side walls 718, reflective end walls 719 and 720 and slit 716. Slit 716 as shown is located on a side wall, but in an alternative arrangement may be located on an end wall. As shown, end walls 719 and 720 are concave so as to form a confocal cavity. In this arrangement photons are reflected between the end walls along the optical cavity axis until absorbed. Depending upon the reflectivity of the end walls and absorption by contaminants in the water, a photon may travel the length of the cavity several hundred times before being absorbed. The long optical path length maximizes the probability of absorption by an unwanted contaminant in the water at low concentration. The reflective side walls and end walls may be first surface metal mirrors or dielectric mirrors. In an alternative arrangement (not shown), the end walls may be plane mirrors. In the plane mirror embodiment, the ray path will walk off the end mirrors if the mirrors are not perfectly parallel, but such walk off is of no consequence if the contamination concentration (and absorption) is high.

Figure 8:
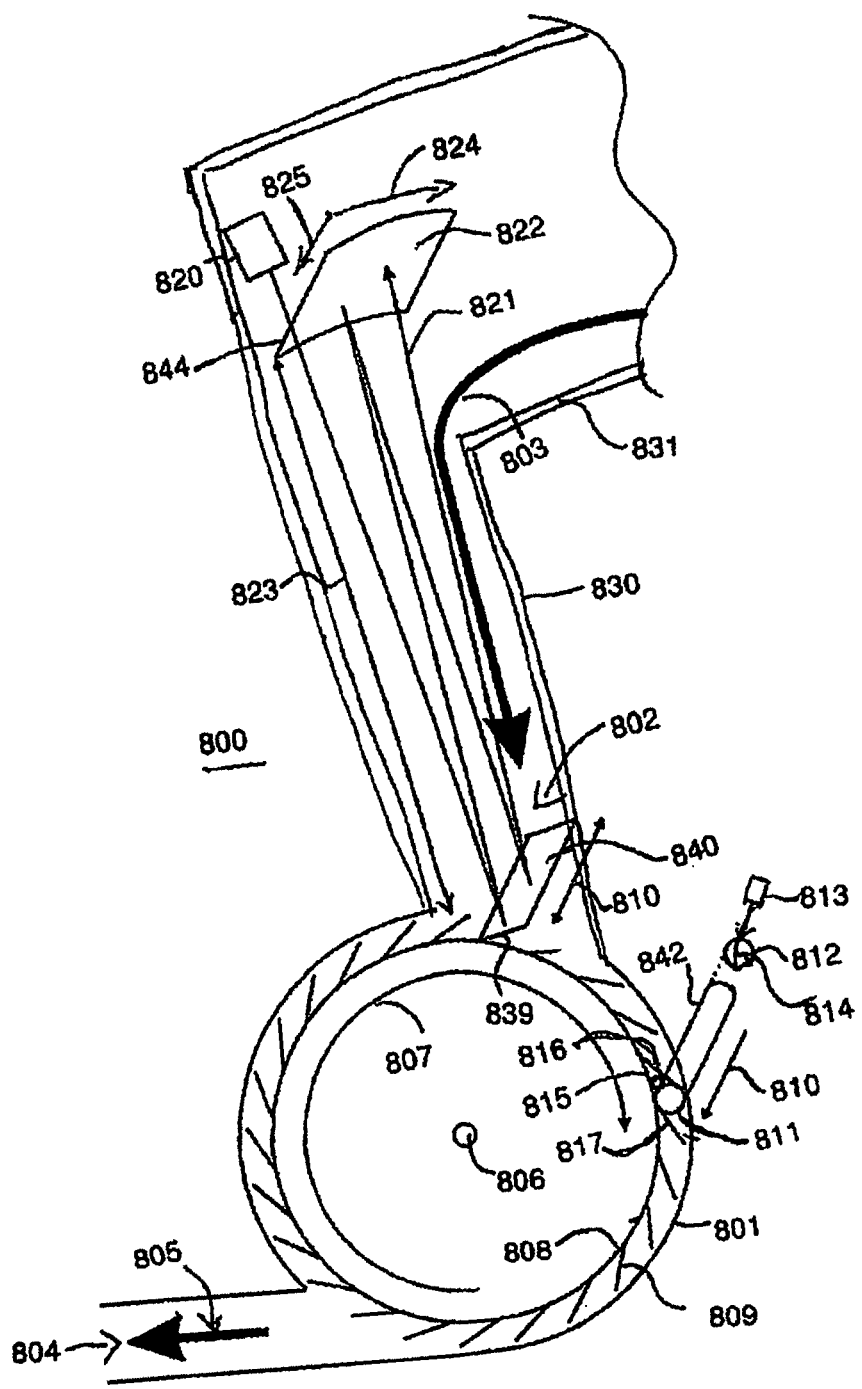
FIG. 8 is a schematic side elevational view of a fan arrangement according to the present invention for use in a chamber of a forced air system.

FIG. 8 shows a drum fan in an arrangement generally indicated at 800 which is configured to sterilize an air flow with ultraviolet radiation. The arrangement may be used to sterilize air inline in a HVAC system. The drum fan has a casing 801 with inlet 802 and outlet 804. Air flows toward the inlet along a path indicated at 803 through a duct 830 with an elbow 831. Air flows from the outlet along the path indicated at 805. Drum 808 rotates as shown at 807 about axis 806. The blades 809 are attached to the drum 808 and angled forwardly and outwardly from a cylindrical surface of the drum to propel entrained air between the drum 808 and the casing 801 from the inlet 802 to the outlet 804. As shown in the single blade marked at 839 which is shown in isometric so that its upper surface and length can be seen, all of the blades 809 have a reflective surface 840 extending at least the width of the blade as indicated at 810 which is equal to the width of the inlet 802. The blades 809 may be comprised of a reflective material such as aluminum with a mirror finish on the surface. The average ultraviolet reflectivity of aluminum between 250 nm and 280 nm is about 92% at near normal incidence. The blades 809 can also be comprised of a structural material such as steel with a reflective material coating attached. The reflective material may be a dielectric mirror.

As described above, the blades act as mirrors in relation to UV light beams transmitted from a source 820 at the elbow 831 which reflect back and forth between each blade as it passes the inlet 802 and a concave mirror 822.

As shown, the blades 809 have a plane surface. In some embodiments, each blade 809 may have a convex outer curved surface shaped to optimize air flow and an inner concave surface which is reflective with a space between the two surfaces. The reflective inner surface is shaped to optimize the number of reflections between each blade 809 as it passes the opening and the mirror 822. The gap between the inner curved reflective surface and outer curved surface may be filled with a transparent material such as fused silica or quartz. The outer surface does not act to cause the reflection so that its shape can be independent of the inner surface.

Ultraviolet light is emitted and collimated by source 820 toward blade 809 and is reflected between blade 809 and mirror 822 a plurality of times as indicated by the path 821. Preferably mirror 822 has little or no curvature in a direction 825 parallel to the direction of the drum axis 806 and has a circular or parabolic profile in the direction indicated at 824. Preferably the distance from the mirror 822 to the blade edge is approximately equal to the focal length of the concave mirror as indicated at 823. The mirror 822 is preferably a dielectric mirror with reflectivity greater than 99% between 250 nm and 280 nm at near normal incidence. As the drum 808 rotates and when the blade has a flat reflective surface, the angle of incidence of ultraviolet radiation from the source 820 onto the blade 809 changes over a range of several degrees and radiation is reflected to different portions of the mirror 822. The curvature of the mirror 822 causes radiation to be reflected to a position on the blade proximate to the position illuminated by source 820. In an embodiment suitable for small angular displacements (less than about 6 degrees) between adjacent blades, the optical surface of the blade is a plane. In another embodiment suitable for larger angular displacements between blades, the optical surface of the blade may be concavely curved. Preferably the focal length of the blade curvature is about the same as the focal length of mirror 822.

In the preferred arrangement, the source 820 is located at one edge 844 of the mirror and is angled relative to the axis 825 so that radiation incidence from the source 820 has a small direction cosine component along the axis 810 causing radiation to "walk" along the axis 825 that is across the width of the reflective surface of the blade over the course of multiple reflections.

Also the location of the source at the edge 844 also causes the radiation to walk across the mirror along the axis 824. This movement of the points of reflection increases the spread of the radiation over the area of the air path to increase interaction between the radiation and the air stream.

Alternately the whole width of the blade 810 may be illuminated by source 820. The radiation path 821 is approximately collinear and coincident with the air flow path 803. Air between the blade 810 and the mirror 822 is exposed to a dose of ultraviolet radiation proportional to the distance between blade 810 and mirror 822 and the effective number of reflections given as the sum of amplitudes of each reflection through the air volume to be sterilized.

For simplicity of illustration only one blade is illuminated. In some embodiments a plurality of blades spanning the air inlet are illuminated.

Another embodiment is shown again in isometric view at the blades 816 and 817, where mirrors 811 and 812 are placed to form an optical cavity 842 located between the pair of blades 816 and 817. This can be used as an alternative to the mirror 822 or as an addition to that embodiment.

The mirrors 811 and 812 are separated by a spacing which is effectively equal to the blade width 810. Although only one example of the optical cavity 842 is shown between blades 816 and 817, the embodiment is understood to include a similar optical cavity 842 between each pair of blades 809. In this way, ultraviolet radiation between from a source 813 is injected into each optical cavity 842 through a small aperture 814 in the end mirror 812. Alternately ultraviolet radiation may be injected into each optical cavity 842 proximate to the edge of mirror 811 as shown at 815. Preferably the mirrors 811 and 812 are concave and form a confocal cavity. Preferably the mirrors 811 and 812 are comprised of a dielectric material with reflectivity greater than 99% between 250 nm and 280 nm.

As the drum 808 rotates from the intake 802 to output 804, air entrained between each pairs of blades 816 and 817 is irradiated by ultraviolet radiation with a dose proportional to the input amplitude from source 813 multiplied by an amplification factor.

The amplification factor in each embodiment is related to the mirror reflectivity as $q/(1-r)$, where q is a factor less than or equal to 1 that accounts for optical losses due to geometric effects. For example, a perfect cavity (q=1) and r=99.9% amplifies the radiation from source 813 by a factor of 1000 and the required residence time in the radiation field for a given dose is consequently reduced by a factor of 1000.

Figure 9:
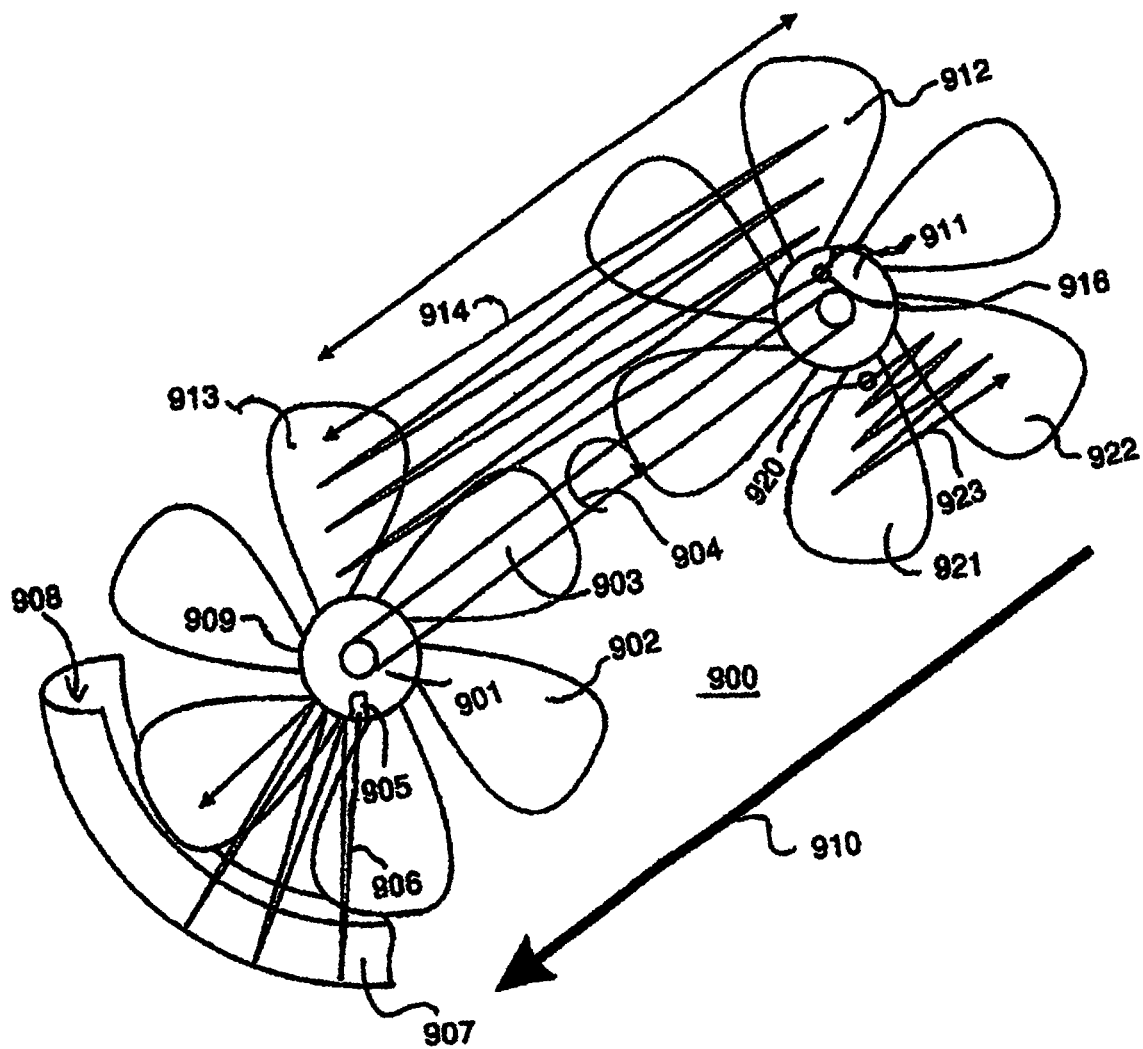
FIG. 9 is a schematic side elevational view of a fan arrangement according to the present invention for use in a chamber of a forced air system.

FIG. 9 shows a further embodiment generally indicated at 900 of an axial fan arrangement for sterilizing air. The arrangement may be used to sterilize air inline in a HVAC system. Hub 901 with blades 902 rotates as shown at 904 on axial shaft 903. Light source 905 mounted on hub 901 directs ultraviolet radiation at an angle slightly offset from a radial direction along path 906 toward mirror 907. Preferably light source 905 is a LED that includes an integral lens or mirror that operates to reduce the angular divergence of the emitted UV radiation. The angular divergence is selected such that radiation is confined between concave mirror 907 and hub mirror 909.

The mirror 907 is shaped as a ring centered on the axis of the shaft 903 with an inwardly facing concave surface 908. In some embodiments mirror 907 corresponds to part of the outer surface of a toroid. In some embodiments the cross section of mirror 907 indicated at 908 has a parabolic shape.

The outer surface of the hub 901 has a reflective surface as shown at 909. In some embodiments hub surface 909 is cylindrical. In some embodiments hub surface 909 is concave along the axial direction (not shown). Preferably the reflective surfaces 908 and 909 are dielectric mirrors with reflectivity greater than 99% for wavelengths between 250 nm and 280 nm near normal incidence. As shown at 906, radiation is reflected between mirrors 908 and 909 a plurality of times with progressively advancing angular displacement about axis of shaft 903 so as to form a circular curtain of radiation lying in the radial plane of the axis of shaft 903. Air propelled by fan blades 902 passes through the curtain of radiation in the axial direction as indicated at 910 receiving a dose proportional to the optical amplification factor as discussed above and the residence time in the radiation field.

In another embodiment which can be used with the above embodiment or as an addition thereto, shaft 903 has two sets of fan blades axially spaced as shown at hubs 901 and 911 carrying blades 902 and 912 respectively thereon. As shown fan blades 902 and 912 on the hubs 910 and 911 have reflective facing surfaces and rotate synchronously. These can be angularly aligned as shown or in some embodiments (not shown), the reflective surfaces of the axially spaced fan blades 902 and 912 are also angularly offset.

The reflective surfaces may be covered with a transparent material such as fused silica, sapphire or quartz that forms an outer surface of each blade which is optimized to propel air in the axial direction 910. The reflective surfaces can therefore be optimized to the light reflection rather than the air flow. The reflective surfaces may for example be aluminum, however more preferably the reflective surfaces are dielectric mirrors. Ultraviolet radiation emitted by a source 916 mounted on the hub 911 is transmitted between the two fan sets and is reflected back and forth between the fan blades 913 and 912 a plurality of times as shown at 914. Preferably the reflective surfaces of the fan blades are shaped to increase the number of reflections at each radial distance from the axis of shaft 903 in proportion to the square of the axial distance. As the blades rotate through a circle, a cylindrical volume between the fan blades is irradiated with ultraviolet radiation with intensity proportional to the optical amplification factor between the facing blades. Although a single pair of facing reflective blades 902, 912 is sufficient to irradiate the entire cylindrical volume spanning the axial offset, in preferred embodiments all fan blades 902 attached to a first hub 901 reflect radiation to a respective fan blade 912 attached to a second hub 911.

In some embodiments the optical cavity between the facing blades 902, 912 is arranged by the shape of the blade surfaces to form a confocal cavity. In some embodiments, the reflective surfaces of a combination of blades form a confocal cavity.

In another embodiment which can be used with the above or as an alternative, sterilizing ultraviolet radiation is reflected between fan blades 921 and 922 attached to the same hub 911 a plurality of times as indicated by path 923. Fan blades 921 and 922 have reflective surfaces. As the fan blades rotate, the radiation field of path 923 sweeps out a disk and air passing through the disk is irradiated.

Light paths 906, 914, and 923 may be used in any combination. For example, axial light paths of type 914 may be combined with angular light paths of type 922 to form multiple curtains of light sweeping through a cylindrical volume between sets of fan blades.

Figures 10A, 10B, 10C, 10D:
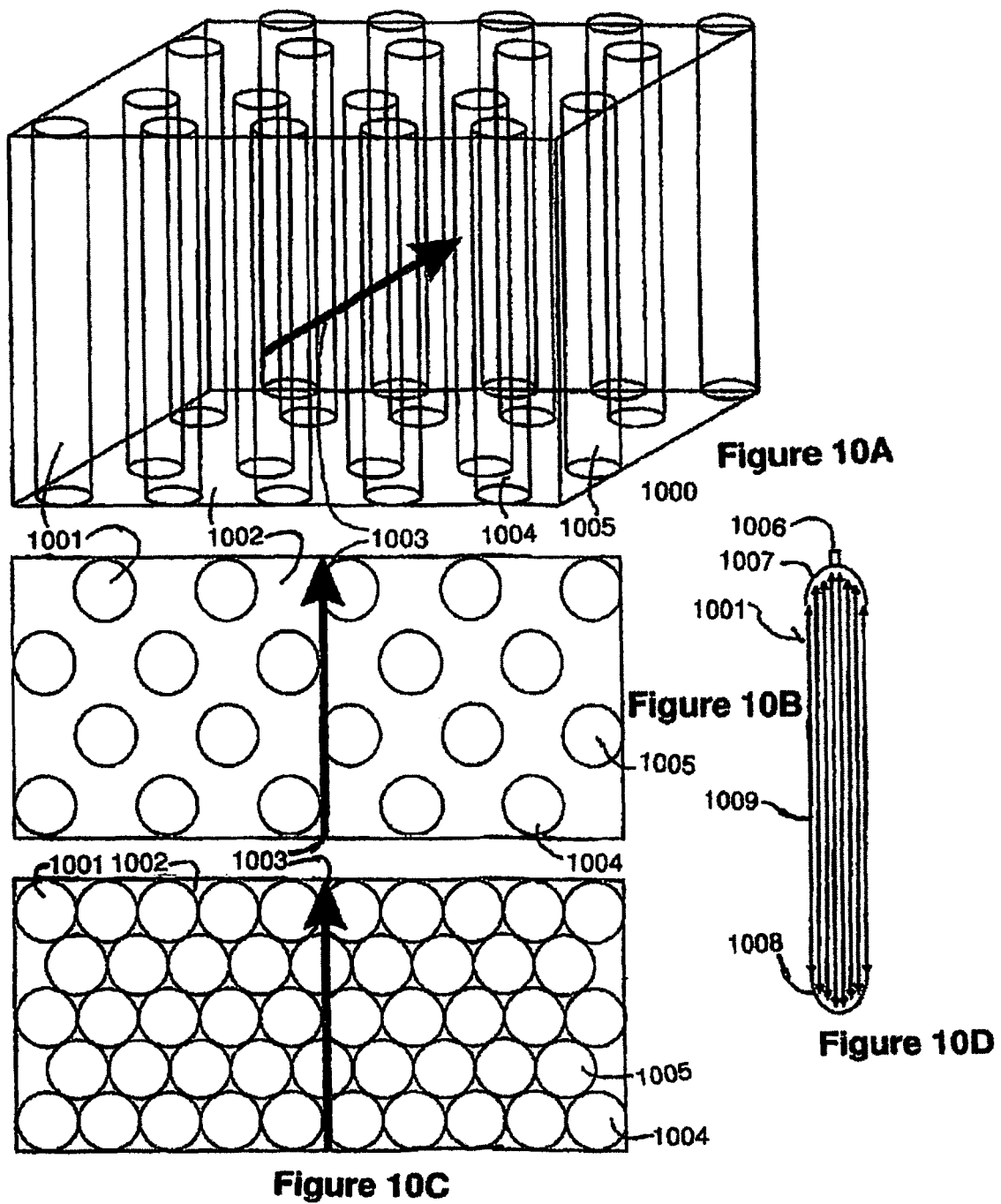
FIG. 10A shows a section of a duct forming a chamber according to the present invention for use in a forced air system.
FIG. 10B is a top plan view of the section of FIG. 10A.
FIG. 10C is a top plan view of a section similar to that of FIG. 10A showing a modified array of the treatment volumes.
FIG. 10D is a cross-sectional view of the section of FIG. 10A showing the end caps which generate a treatment volume.

FIG. 10A shows an isometric view of radiation field zones in an air duct generally indicated at 1000. The radiation field zones 1001, 1004, 1005 are generally cylindrical volumes within an optical cavity with a high density of germicidal ultraviolet photons. The duct volume 1002 contains a plurality of radiation field zones 1001. The fields are defined only by concave end mirrors 1007 and 1008 with no intervening walls so that the light is only confined by its reflections from the mirrors.

The radiation field zones are arranged in an array such that a straight air flow path along the duct intersects with at least one and preferably more of the volumes so that the volumes in effect overlap relative to such a straight line path such that each air flow path 1003 passes through at least one radiation field zone. FIG. 10B shows a top view of the arrangement in FIG. 10A. FIG. 10C shows a top view of a preferred arrangement in which the radiation field zones 1001 are hexagonal close packed in the air duct 1002.

As best seen in FIG. 10D, the radiation field zones 1001 are defined by the interior of a confocal optical cavity. Ultraviolet radiation enters the cavity from source 1006 through a small aperture (not shown) in concave end mirror 1007. Concave end mirror 1007 together with concave end mirror 1008 thus form a confocal optical cavity. End mirrors 1007 and 1008 are preferably recessed into the duct walls so as to minimally interfere with the air flow. Only the radiation field between the end mirrors indicated at 1009 extends into the air flow region of the duct. End mirrors 1007 and 1008 may be comprised of aluminum with reflectivity 92%. Preferably end mirrors are comprised of a dielectric material with reflectivity greater than 99%. The radiation source may for example be a LED. Most preferably the end mirrors 1006 and 1007 have reflectivity greater than 99.9%. The end mirrors may have a concave spherical surface. Most preferably the end mirrors have a concave parabolic profile so as to maximize the number of reflections between end mirrors 1007 and 1008. Increasing the number of reflections amplifies the radiation field produced by the source 1006 alone.

In an embodiment (not shown), the walls of the air duct may be lined with a transparent material such as fused silica or quartz to present a smooth surface for air flow. However, the reduction in air resistance must be balanced against optical losses from Fresnel reflection at the added optical interfaces. That is the reduced energy requirement to move air must be balanced against the increased energy requirement for radiation sources 1006 due to increased optical losses.

As shown in FIG. 10 A, the radiation field zones are generally perpendicular to the direction of air flow 1003 in duct 1002. In another embodiment (not shown), the axis of the radiation zones may be angled to have a component in the direction of air flow 1003, thereby increasing the residence time (and dosage received) of a volume element of air in the radiation field.

Figure 11:
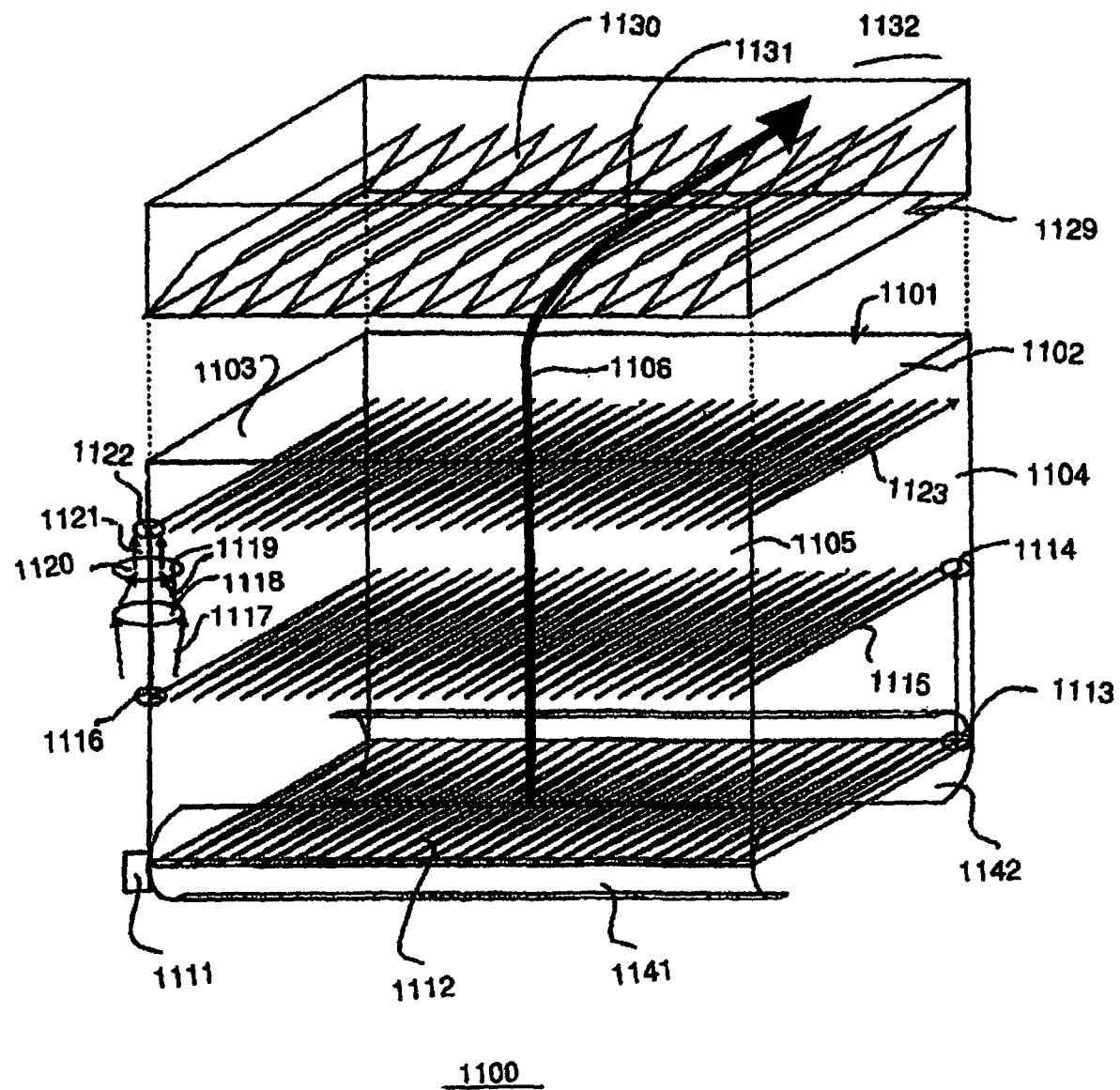
FIG. 11 is a schematic isometric view of a section of a duct forming a chamber according to the present invention for use in a forced air system.

FIG. 11 shows a schematic arrangement for air duct sterilization with multiple light curtains generally indicated at 1100. Air duct 1101 is bounded by duct walls 1102, 1103, 1104 and 1105. Air flows through duct 1101 along the path indicated at 1106, which optionally includes a louver assembly 1129 with louvers 1130 that deflect air flow as shown at 1131 into volume 1132. Volume 1132 may for example be a room. The louvers 1130 are comprised of an absorbent material and shaped to block radiation from passing from air duct 1001 to room volume 1132.

Radiation source 1111 directs a collimated germicidal ultraviolet radiation beam onto path 1112 reflecting between concave mirrors 1141 and 1142 mounted at respective duct walls 1105 and 1104 with a small angle of incidence along the mirrors. The angle of incidence is set such that the distance between successive reflections on the same mirror is less than the radiation beam width, thereby creating a continuous curtain of radiation. The mirrors at the duct walls are comprised of a reflective material. As an alternative, the mirrors are omitted and the reflection is carried out by the walls 1104 and 1105. In this case, the duct walls are comprised of a highly reflective material such as a dielectric mirror at locations where the radiation beam intersects a duct wall. Rather than provide a separate mirror, the duct walls 1104 and 1105 have a locally defined concave shape acting in the same manner as the mirrors that acts to focus the incident radiation beam and limit angular divergence to the plane of path 1112. As shown at 1113, a mirror is angled to direct the radiation beam from path 1112 toward mirror 1114. Mirror 1114 directs the radiation beam onto path 1115, which zigzags between the duct walls 1004 and 1005. Mirrors 1113 and 1114 are functionally equivalent to a periscope and are composed of a highly reflective material that maximizes radiation transfer from path 1112 to path 1115. The intersection points of path 1115 with duct walls are highly reflective concave surfaces (not shown). Radiation from path 1115 is reflected by mirror 1116 toward a collimation arrangement schematically represented by lenses 1118 and 1120. The collimation arrangement may also be comprised of reflective optical elements (not shown). As indicated at 1117 the radiation beam reflected from mirror 1116 is divergent. First optical element 1118 focuses the divergent beam as shown at 1118 and second optical element 1120 collimates the radiation beam as indicated at 1121. The collimated beam is reflected by mirror 1122 onto path 1123.

Radiation paths 1112, 1115 and 1123 form three light curtains that intersect air flowing along path 1106. As shown, the light curtains are perpendicular to the direction of air flow. In a preferred embodiment (not shown), the light curtains are be angled such that a component of the radiation beam direction is parallel or anti parallel to the direction of air flow, thereby increasing the residence time of an air volume element in the radiation field of each light curtain.

It will be appreciated that there is no intended exit port for the photons so that the photons remain in the chamber unless they escape through unintended openings such as fluid inlet/outlet openings. As shown in FIG. 7 this unintended escape is reduced or eliminated in that there is provided a mirror 750, 751 behind each unintended opening such as the fluid inlet/outlet openings 725 so as to reflect escaping photons back into the chamber. Preferably as shown the mirror is a focusing mirror so as to reflect escaping photons back through the opening into the chamber.

Figure 12:
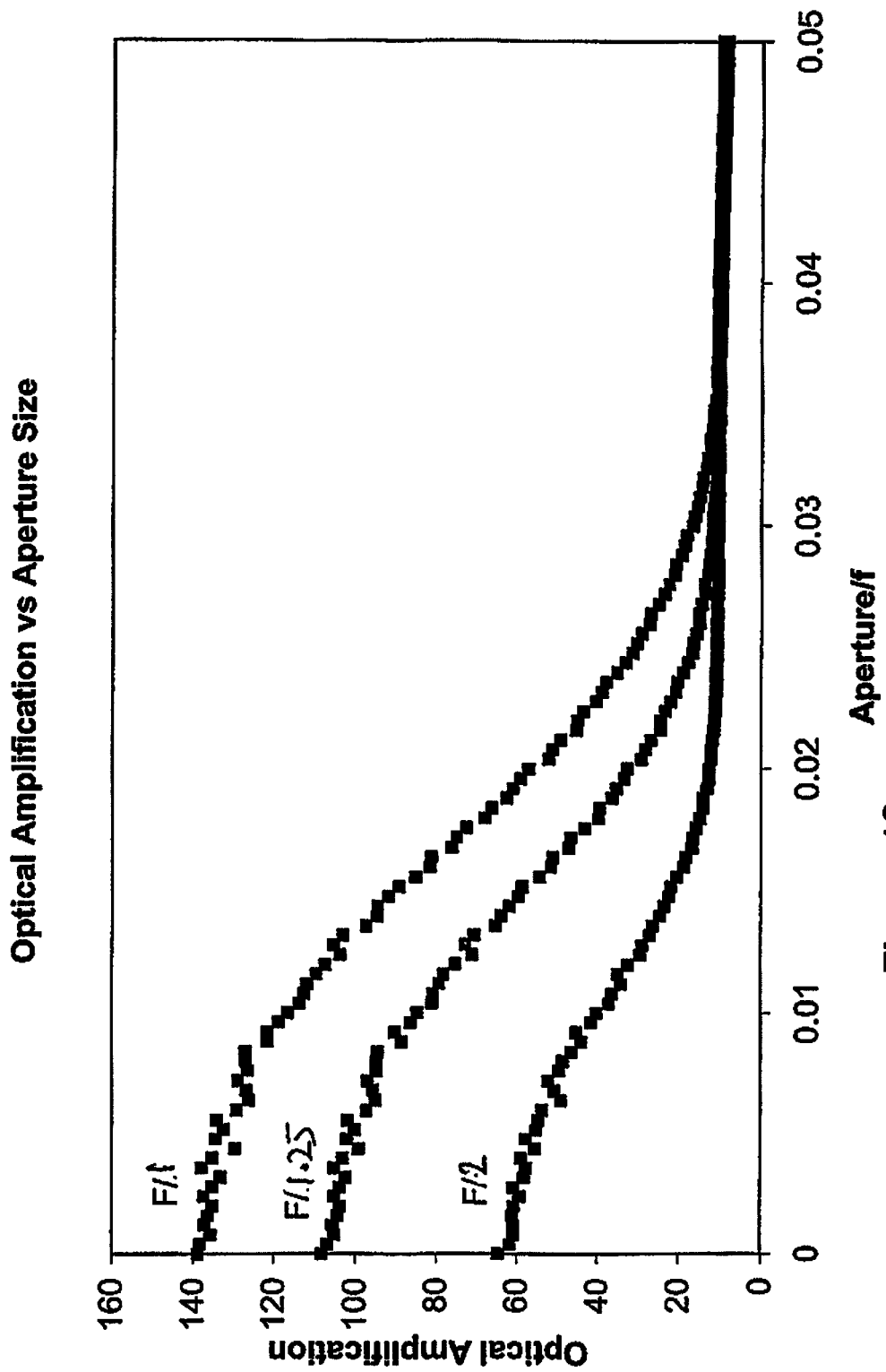
FIG. 12 is a graph showing the effect of optical amplification relative to a dimension of a source of the radiation when located on one of the mirrors of the opposed mirror arrangements of FIG. 1 or FIG. 6.

FIG. 12 is a graph showing three separate plots of the effect of optical amplification relative to a dimension of a source of the radiation when located on one of the mirrors of the opposed mirror arrangements of FIG. 1 or FIG. 6. The graph is normalized for focal length of the mirrors: that is the x axis shows values of aperture size divided by focal length. The three plots shown relate to three values of focal length F divided by the diameter of the mirror. The conclusion for the three plots is that, in all cases the transverse dimension of the source when located within the bounds of the mirror surface generally at or adjacent the center axis of the mirror as shown for example at source 42 in FIG. 1, the transverse dimension should be less than 0.03 times the focal length of the mirror and most preferably less than 0.01 times the focal length of the mirror. It will be appreciated that the size or transverse dimension of the source can be determined either by selection of a source of the required dimension or my focusing the radiation from a larger source through an aperture of the required dimension.

Figure 12A:
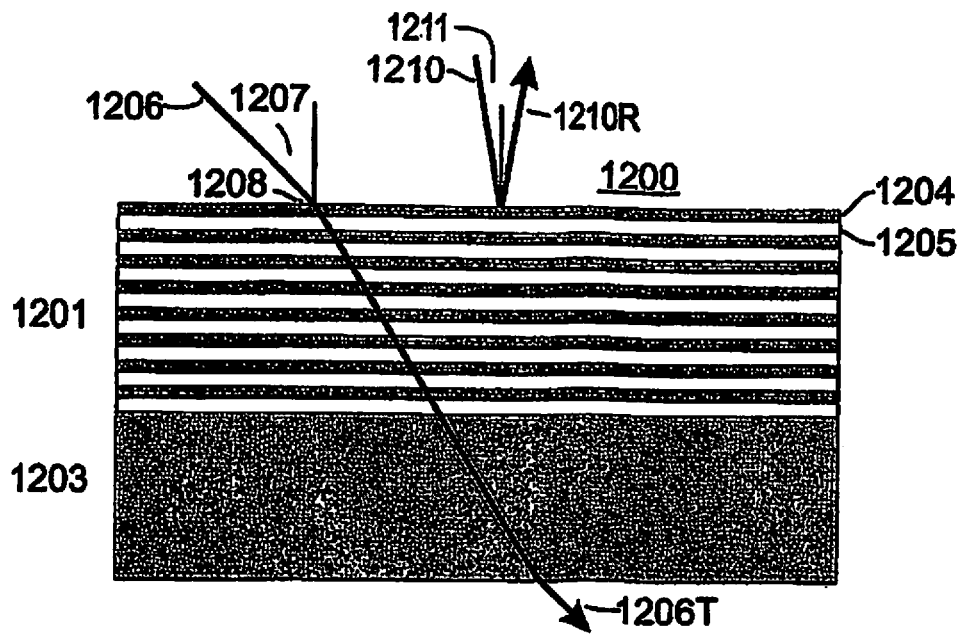
FIG. 12A shows a schematic cross-sectional view of a prior art dielectric mirror.

FIG. 12A shows a schematic cross-sectional view of a prior art dielectric mirror generally indicated at 1200. The dielectric mirror consists of a stack of dielectric layers 1201 on a substrate material 1203. Although the substrate as shown is flat, the substrate may be curved to produce for example a spherical or parabolic mirror in the arrangements as shown above. The layers 1204 and 1205 are comprised of high refractive index and low refractive index materials, respectively. Refraction and reflection occur at each interface in the stack (not shown). Reflections occur that add constructively contribute to the dielectric mirror reflectivity.

For example, a light ray 1206 entering at first angle of incidence 1207 is incident on the dielectric mirror at 1208 and is refracted. The reflections from the dielectric layers do not satisfy the condition for constructive interference so the light ray 1206 is transmitted as shown at 1206T.

For example, a light ray 1210 is incident upon the dielectric mirror with a second angle of incidence 1211. Due to the different angle, the optical path lengths through the dielectric layers are combined with the phase change on reflection give a total phase change corresponding to integer multiples of the light wavelength and the reflected waves interfere constructively as shown at 1210R. In commercial mirrors of this type, the layer thickness and refractive index are selected to optimize reflectivity over a predetermined range of wavelength and angle of incidence. Higher reflectivity can be obtained as the design wavelength range or angle of incidence range is narrowed. That is different mirrors are available which are designed to have selected range of operation in respect of wavelength and angle of incidence.

In the reaction chamber of the present invention as described in the embodiments above where the angles of incidence change, the optical amplification obtained is limited by optical losses when actual angles of incidence fall outside the optimal working range of the mirror. The dielectric end mirrors shown at 611 and 612 in FIG. 6 are ideally designed for near normal incidence. In this case, rays with angles of incidence above a threshold value of about 45 degrees are transmitted rather than reflected. The reaction chamber should be designed such that the angle of incidence does not exceed this threshold. However, high reflectivity over a large range of angles of incidence is desirable to homogenize the radiation flux within the chamber volume.

Figure 12B:
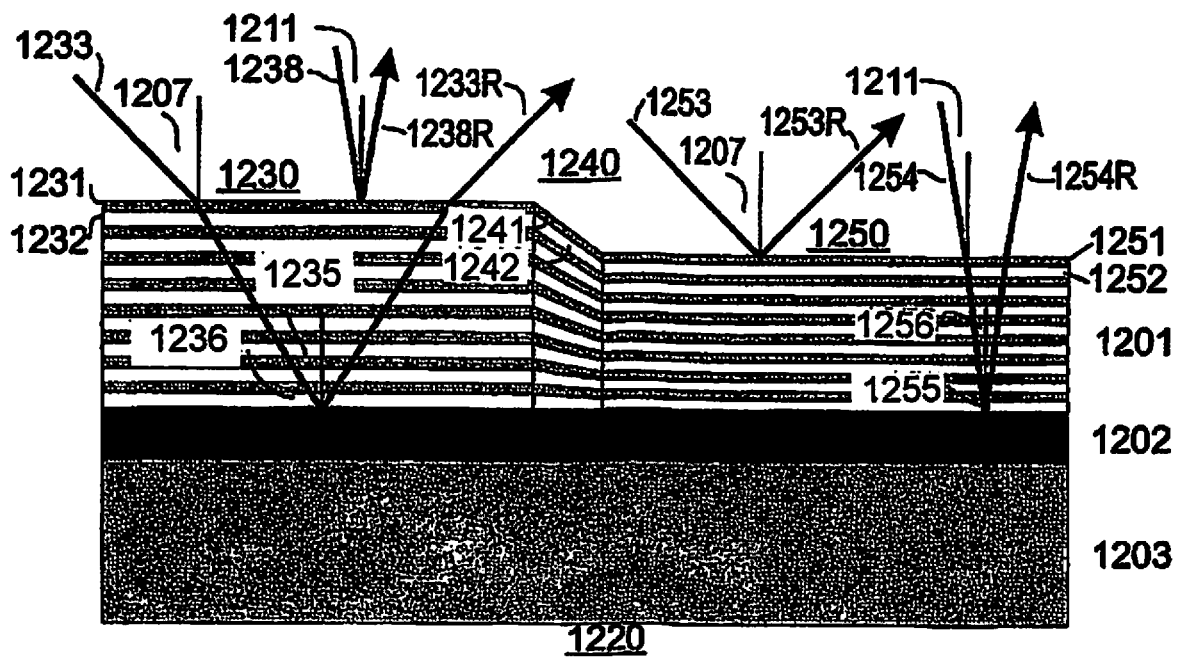
FIG. 12B shows schematic cross-sectional view of an improved dielectric mirror according to the present invention.

FIG. 12B shows schematic cross-sectional view of an improved dielectric mirror generally indicated at 1220. The dielectric mirror is comprised of a layered stack of dielectric layers 1201, a first surface mirror 1202, and a substrate

1203. The order of the substrate and first surface mirror layers may be interchanged (not shown). The first surface mirror 1202 is comprised of any material that is highly reflective in the wavelength region of interest. Suitable choices for the first surface mirror that cover a wide spectral range are aluminum for UV wavelengths, silver for visible wavelengths and gold for infrared wavelengths. Other materials may be used. The first surface mirror 1202 may be a thin layer of reflective material deposited on a substrate material 1203 or the first surface mirror may be a block of material thick enough to provide both reflectivity and mechanical support, in which case the substrate layer 1203 may be omitted.

Three types of dielectric mirror stacks are shown generally indicated at 1230, 1240, and 1250.

In dielectric mirror region 1230, the thickness of high refractive index layer 1231 and low refractive index layer 1232 are chosen such that the optical path lengths are odd integral multiples of wavelength/4 for near normal angles of incidence giving high reflectivity for small angles of incidence.

Incident light ray 1233 at first angle of incidence 1207 is outside the designed angle of incidence for the mirror and hence is not reflected but instead is transmitted (with refraction) through the dielectric stack and is incident upon the first surface mirror 1202 at 1236 with angle of incidence 1235 less than first angle of incidence 1207. The angle of incidence 1235 at the first surface mirror can be modified by choice of refractive index of layers 1231 and 1232. The dielectric layers may be designed such that the most frequently occurring angles of incidence 1207 correspond to angles of incidence 1235 where first surface mirror 1202 has high reflectivity. Put another way, the design should avoid the angle 1235 corresponding to Brewster's angle for any mode with significant energy. Radiation reflected at the first surface mirror 1202 is refracted and exits as shown at 1233R. Light ray 1238 incident at second angle 1211 is reflected by the dielectric layers due to constructive interference and exits as light ray 1238R as discussed above. Hence in region 1230, light rays with a large angle of incidence 1207 are transmitted through the dielectric stack and reflected at the first surface mirror and light rays with a small angle of incidence 1211 are reflected by the dielectric stack.

In dielectric mirror region 1250, the thickness of high refractive index layer 1251 and low refractive index layer 1252 are chosen such that the optical path lengths are odd integral multiples of wavelength/4 for large angles of incidence giving high reflectivity for large angles of incidence. Incident light ray 1253 at first angle of incidence 1207 is reflected by the dielectric stack and exits as light ray 1253R. Light ray 1254 at second angle of incidence 1211 is transmitted by the dielectric stack and is incident on first surface mirror 1202 at location 1255 with angle of incidence 1256. Angle of incidence 1256 is less than second angle of incidence 1211 and may be adjusted by design as discussed above. Radiation reflected by first surface mirror 1202 at 1255 is refracted and exits as shown at 1254R. Hence in region 1250, light rays with a large angle of incidence 1207 are reflected by the dielectric stack and light rays with a small angle of incidence 1211 are reflected by the first surface mirror.

As illustrated in region 1240, the high refractive index layer 1241 and low refractive index layer 1242 may have continuously varying thickness. Further, the overall number of dielectric layers in the stack may vary with location. Hence the reflectivity as a function of angle of incidence will be intermediate between the reflectivity of regions 1230 and 1250. With the arrangement of FIG. 12B, the overall reflectivity is greater than or equal to the reflectivity of the first surface mirror for all angles of incidence.

Figure 13:
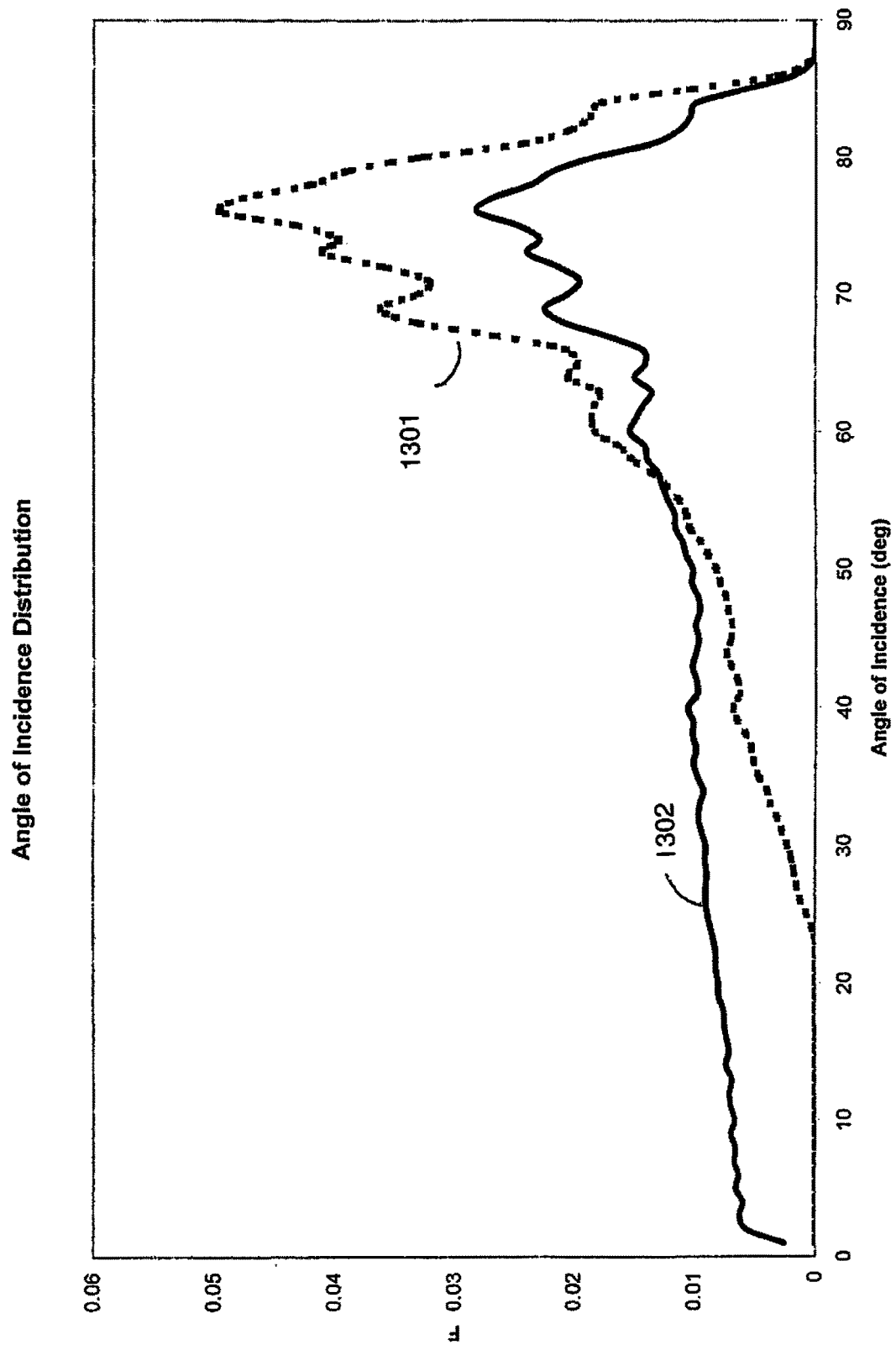
FIG. 13 is a graph showing the distribution of angles of incidence for a simulation of the arrangement shown in FIG. 6 wherein the end mirrors are dielectric mirrors and the side walls are a first surface aluminum mirror.

FIG. 13 shows the distribution of angles of incidence for a simulation of the arrangement shown in FIG. 6 wherein the end mirrors 611 and 612 are dielectric mirrors and the side walls 610 are a first surface aluminum mirror. The dashed curve shows the normalized distribution of angles of incidence on sidewall 610. Small angle reflections below about 25 degrees correspond to large angles of incidence at the end mirrors and are lost to transmission as shown at 1206T in FIG. 12A. Rays with grazing angles of incidence between 70 degrees and 80 degrees at the side walls correspond to small angles of incidence at the dielectric end mirrors and propagate for hundreds of reflections. The solid line curve 1302 shows the normalized distribution of incident angles for a simulation in which all of the surfaces are of the type shown in region 1230 of FIG. 12B. All other parameters are the same between the two cases. The distribution of incident angles is more uniform giving a more homogeneous radiation field in the reaction chamber. The optical amplification is more than 2× higher for the arrangement 1230. Use of the composite mirror arrangement permits more favorable choices for radiation source parameters leading to a gain in optical amplification of more than 8×.

Figure 14:
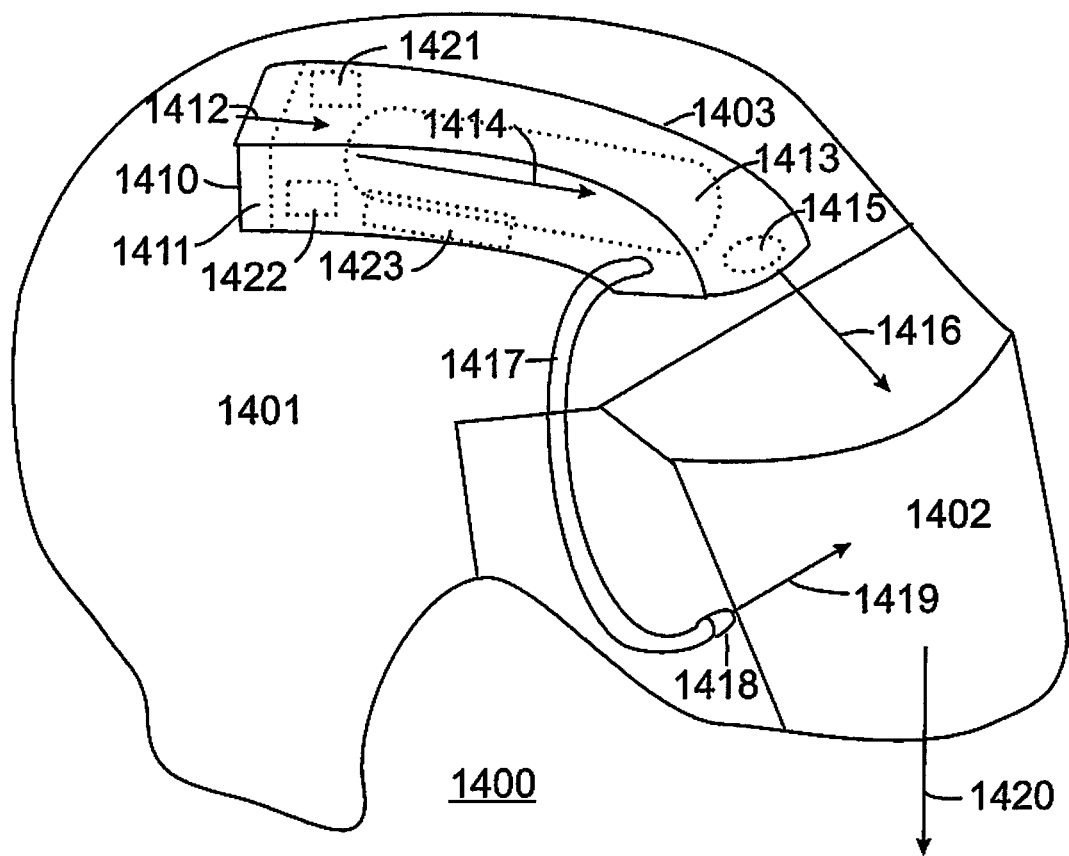
FIG. 14 is a perspective view of a sports helmet with an integral sterilization chamber according to the present invention.

FIG. 14 is a perspective view of a sports helmet with an integral sterilization chamber indicated generally at 1400. The sterilization chamber provides a stream of sterile air to the athlete wearing the helmet. The sports helmet consists of three main units: helmet body 1401, face shield 1402, and sterilization unit 1403. The sterilization unit may be an appendage such as a crest on the helmet body as shown. In an alternate embodiment (not shown), the sterilization unit may be enclosed within the helmet body. In an alternate embodiment (not shown), the sterilization unit may be mounted on the face shield, generally at the level of the nose, mouth, or neck of the wearer. The sterilization unit 1403 has similar form and function to the arrangements shown in FIG. 1 and FIG. 6. For brevity only the major components are shown schematically. Fan 1411 draws non-sterile air though a vent 1410 in the back of the helmet body 1401 generally in the direction from posterior to anterior as indicated at 1412. The non-sterile air enters sterilization chamber 1413 and flows through the sterilization chamber as indicated at 1414 in the presence of a UV radiation field which sterilizes the air as discussed previously for FIG. 1 and FIG. 6. The path through the sterilization chamber 1413 may be tortuous. In some embodiments, sterile air is directed though an aperture 1415 proximate to the top of the face shield 1402 in the direction indicated at 1416. In this embodiment sterile air flows generally across the face from the forehead toward the chin and is constrained to the vicinity of the face by the face shield. Air exhaled by the athlete together with remaining sterile air is expelled at the bottom of the face shield as shown at 1420. This embodiment has the additional benefit of providing cooling air across the entire face to the athlete. The fan 1411 generates positive air pressure between the face of the athlete and the face shield preventing non-sterile air from flowing into the facial region at the bottom of the face shield. That is the fan supplies a flow of sterilized air that is sufficient for both respiration and to displace non-sterile air at the bottom of the face shield.

In an alternate embodiment, sterile air is directed through a tube 1417 to a nozzle 1418 which directs a sterile air stream toward the nose and mouth region for respiration as indicated at 1420. The direction of nozzle 1418 is adjustable so that the athlete can aim air flow in a direction suited to the athlete's physiology. The sterilization unit includes a control unit 1421 and a power supply 1422 which perform the same functions as discussed for FIG. 1. Optionally the sterilization unit may include an air cooler shown schematically at 1423, which may for example be a thermo-electric cooler.

In an alternative embodiment (not shown), the helmet body 1401 is a hat, head band or balaclava without a face shield 1402. Nozzle 1418 is attached to the hat, headband or balaclava and directs sterilized air toward the mouth and nose region of the hat, headband or balaclava wearer's face. That is the hat, headband or balaclava provides structural support for the nozzle. The sterilization unit 1403 may be integral with the hat, headband or balaclava or worn on the person separately. Tube 1417 connects the sterilization unit with the nozzle.

In an embodiment that can be used with any of the following or preceding embodiments, the reaction chamber is comprised of a deformable material. The deformable material may for example be a malleable metal, rubber, plastic, foam, fabric, composite, liquid, or other suitable deformable material. In some embodiments, the deformable material is deformed by an external force and returns to its original shape when the external force is removed. For example, the deformable mirror may be used to form a sterilization chamber in a sports helmet that is subject to impact forces. In some embodiments, the deformable material does not return to its original shape. For example, a fabric may be used to form a sterilization chamber that can be collapsed for transport.

FIG. 15 shows cross sectional view of a deformable mirror generally indicated at 1510. The mirror is comprised of a deformable substrate material 1501 with deformable surface 1514 coated with a one or more layers of micro-mirrors. In some embodiments a first surface layer 1502 is comprised of first surface micro-mirrors 1511 and a second layer 1503 is comprised of dielectric micro-mirrors 1512. In this arrangement the dielectric micro-mirrors 1512 reflect light incident within a first range of angles and the first surface micro-mirrors 1511 reflect light incident at angles outside of said first range of angles and light that passes through gaps between micro-mirrors in the top layer 1503. In some embodiments, a deformable surface is covered with one or more layers of composite dielectric micro-mirrors 1513. The composite dielectric micro-mirrors may be of the type shown in FIG. 12B in which a stack of dielectric layers 1201 overlays a first surface mirror 1202. In this embodiment, the micro-mirrors 1513 are preferentially oriented such incident radiation is incident on the dielectric stack first. Most preferably the composite dielectric micro-mirrors 1513 are of the type shown in expanded view at 1504. The composite dielectric micro-mirror 1504 is comprised of a first surface mirror layer 1516 positioned between a first stack of dielectric layers 1515 and a second stack of dielectric layers 1517. The micro-mirror 1504 does not need to be oriented as dielectric layers 1515 face incident radiation in a first preferred orientation and dielectric layers 1517 face incident radiation in a second preferred orientation. The dielectric stacks 1512, 1515 and 1517 are comprised of alternating layers of high refractive index material 1518 and low refractive index material 1519. In some embodiments micro-mirrors of type 1511, 1512 or 1513 are attached to deformable surface 1514 by electrostatic forces. In some embodiments micro-mirrors of type 1511, 1512 or 1513 are attached to deformable surface 1514 with an adhesive 1505. In some embodiments micro-mirrors of type 1511, 1512 or 1513 are embedded in a layer of deformable transparent material 1506. The thin layer of deformable transparent material may for example be a polymer material. The micro-mirrors may for example be applied to deformable surface 1514 as in ink comprised of micro-mirrors 1511, 1512, or 1513 and a solution comprised of a solvent and a polymer material.

The micro-mirrors 1511, 1512, and 1513 have a generally planar shape wherein the linear dimension of the micro-mirror 1507 is much greater than the thickness 1508. For example, the aspect ratio may be 10:1 or more. The linear dimension may for example be in the range of 10 microns to 2000 microns. Because of the high aspect ratio, the micro-mirrors will tend to align parallel to the local plane of the deformable substrate material 1501 to minimize potential energy. The linear dimension 1507 is chosen to limit the mechanical stress on the micro-mirrors with deformation of surface 1514 to a stress below the yield point of the micro-mirror materials: that is the micro-mirror does not fracture. The gaps between micro-mirrors serve to relieve mechanical stress. In some embodiments the micro-mirrors are irregularly shaped flakes. In preferred embodiments, the micro-mirrors have regular shapes that form a space filling array: that is the space between adjacent micro-mirrors is minimized. For example the micro-mirrors may have the shape of hexagonal plates. In some embodiments, a plurality of micro-mirror sizes is used to form a space filling array. In some embodiments a plurality of micro-mirror layers are applied to deformable surface 1514 such that the reflective portions of micro-mirrors in a top layer overlay gaps between micro-mirrors in a bottom layer. In some embodiments the micro-mirrors are placed on the deformable surface with random centers, for example if the micro-mirrors are applied as an ink. In some embodiments the micro-mirrors are assembled in a self-assembling Langmuir-Blodgett film and the Langmuir-Blodgett film is applied to the deformable surface 1514. In some embodiments the micro-mirrors are applied to the deformable surface 1514 as arrays on a sheet joined with thin bridges of connecting material and the thin bridges are subsequently fractured or removed. In some embodiments the micro-mirrors are individually placed and attached to the deformable surface 1514.

FIG. 15B shows a schematic cross-sectional view of a deformable scale mirror array generally indicated at 1520. Mirror plates 1521 are arranged at quasi-regular intervals along a flexible connecting member 1522 in the general chain direction indicated at 1527. The intervals are chosen such that the mirror plates overlap and present a continuous reflective surface to radiation incident at all but grazing angles of incidence near the chain direction 1527. Flexible connecting member 1522 may for example be a wire or a fiber. In some embodiments mirror plate 1521 is comprised of substrate material 1524 and dielectric stack 1525. Substrate 1524 may have an aperture 1523, which functions as a point of connection between successive mirror plates: that is connecting member 1522 passes through aperture 1523. Aperture 1523 has a diameter larger than the diameter of connecting member 1522 allowing a limited range of translation and angular displacement of mirror plates 1521. Connecting members 1522 may form a two-dimensional surface. For example connecting members 1522 may be arranged in a rectangular or hexagonal grid with cross connecting members indicated at 1526. Cross members 1526 serve to limit the range of linear displacement of mirror plates 1521. Hence, as the web of connecting members deforms, the collective shape of the mirror formed by mirror plates deforms. In some embodiments the mirror plates are comprised substantially of a single material that forms both a base and a first surface mirror as indicated at 1526. The material may for example be a reflective metal such as aluminum, silver or gold, which may also include a protective layer of transparent material. In a preferred embodiment, substrate 1524 forms a first surface mirror and is covered with a dielectric mirror 1525. The composite mirror functions as discussed with reference to FIG. 12B.

FIG. 15D is a schematic cross-sectional view of a deformable mirror comprised on an ordered array of mirrors generally indicated at 1530. The deformable mirror consists of a deformable substrate material 1531 and at least two types of mirrors 1532 and 1533 that differ in the length of attachment member 1534. Mirrors 1532 and 1533 are arranged on a periodic lattice such that the reflective surfaces of mirrors of type 1533 overlap the reflective surfaces of mirrors of type 1532. Mirrors of type 1533 preferably reflect most incident radiation and mirrors of type 1532 reflect radiation that passes through gaps between mirrors of type 1533. The gap size and length of attachment member 1534 are selected to allow a specified range of angular displacement to a user. The range of angular displacement is in turn determined by the maximum surface curvature permitted by substrate material 1531. Attachment member 1534 of both types is firmly attached to deformable substrate 1531 and allows angular, but not translational displacement of mirrors 1532 and 1533 relative to the substrate material. Deformation of the substrate material may cause small changes in the periodicity of the mirrors 1532 and 1533 relative to a fixed frame of reference. In some embodiments, the mirrors 1532 and 1533 are comprised of a single material that also forms a front surface mirror with normal approximately perpendicular to the deformable substrate surface as shown at 1538. In preferred embodiment mirrors 1532 and 1533 consist of an attachment member 1534, base 1535 that also functions as a front surface mirror, and dielectric mirror 1537. Optionally dielectric mirror 1537 is encased in a front surface mirror as shown at 1536. Front surface mirror 1536 functions to prevent radiation from entering dielectric mirror 1537 through the side of the dielectric stack. As shown at 1539, the mirror surface may be convex. This feature may be used in a reaction chamber to make the radiation field more homogeneous. As shown at 1540, the mirror surface may be concave. This feature is particularly useful for focusing radiation incident on mirrors of type 1532 through the gap between mirrors of type 1533. In some embodiments, the mirror angular displacements are determined by deformation of the substrate 1531. In some embodiments the mirror angular displacements are determined at least in part by an electro-mechanical actuator. For example, the mirrors may form an electro-mechanical micro-mirror array with two overlapping layers. The addition of a second layer increases the optical efficiency of the array.

Figure 16A:
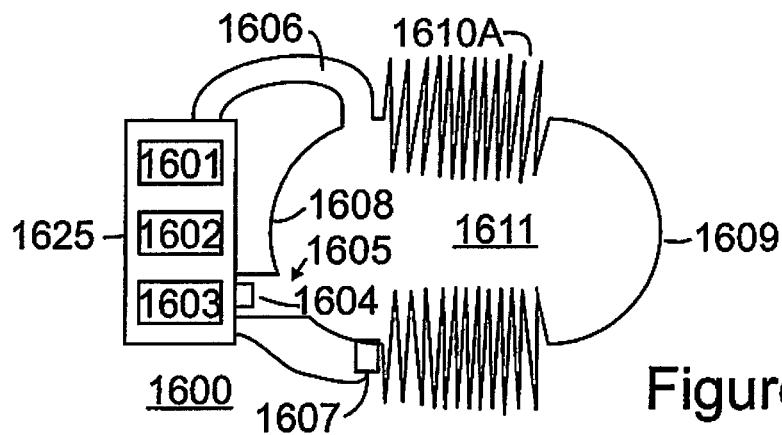
FIG. 16A is a schematic view of a portable sterilization chamber configured for transport according to the present invention.

FIG. 16A is a schematic view of a portable sterilization chamber configured for transport generally indicated at 1600. The major components of the portable sterilization chamber are a utility module 1625 and a sterilization volume 1611. The utility module includes a fan 1601 that draws air into the system, an electronic control module 1602 that includes the functionality described previously for control 4 in FIG. 1, and a power supply 1603. Power supply 1603 may for example be a rechargeable battery. Utility module 1625 is connected with UV radiation source 1604. UV radiation source may for example be a LED. UV radiation is emitted into cavity 1605 which is shaped to and formed to control the angular distribution of radiation emitted into sterilization volume 1611. That is the angular distribution of the emitted radiation is controlled such that the dominant emission angles correspond with angles of highest reflectivity of the deformable reflective material. Utility module 1625 is in communication with sensor module 1607. Sensor module 1607 is operable to measure UV radiation field amplitude and optionally the temperature, humidity, and particulate concentration of air in sterilization volume 1611. Air to be sterilized is directed along duct 1606 from fan input 1601 to sterilization volume 1611. Sterilization volume 1611 is bounded by end mirrors 1608 and 1609 and by deformable reflective material 1610A. In some embodiments end mirrors 1608 and 1609 are comprised of a deformable reflective material. The deformable reflective material may for example be selected from the arrangements described in FIGS. 15 to 15E. As shown, the deformable reflective material is folded to reduce the size of the apparatus for transport or storage.

Figure 16B:
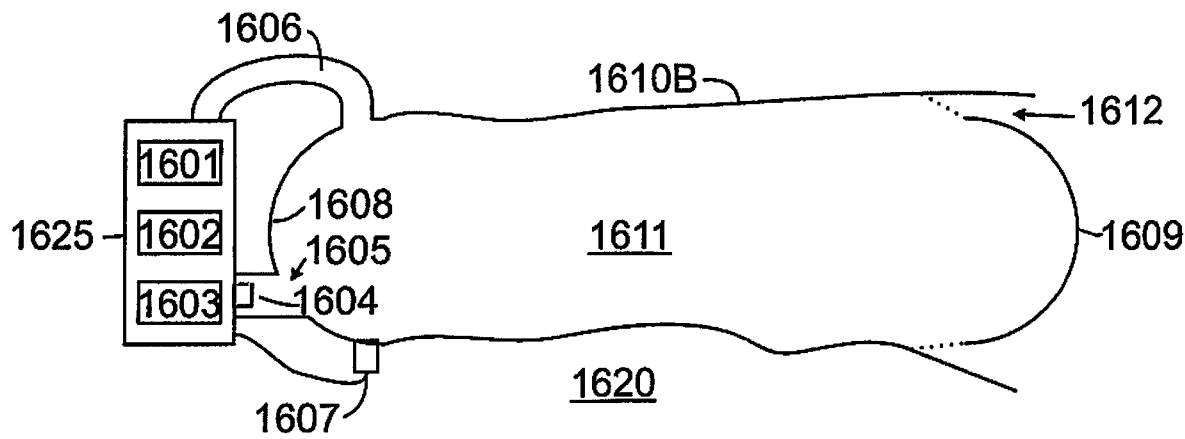
FIG. 16B shows a schematic view of a portable sterilization chamber configured for operation according to the present invention.

FIG. 16B shows a schematic view of a portable sterilization chamber configured for operation indicated generally at 1620. This arrangement is similar to the arrangement in FIG. 16A, except that the deformable reflective material is extended as indicated at 1610B. In some embodiments deformable reflective material 1610B is inflated and shaped by air pressure from fan 1601. The extended shape of the deformable reflective material may for example be approximately cylindrical. The extended shape of the deformable reflective material may for example be approximately rectangular. As shown, the surface shape of the deformable reflective material does not need to be smooth to be functional. The high reflectivity conferred by the arrangements in FIGS. 15 to 15E is more important than surface smoothness. The efficiency of the arrangement can be increased by increasing the distance between the end mirrors 1608 and 1609. Sterilized air is expelled through vent 1612. Vent 1612 may for example be connected with a mask for respiration.

Figure 16C:
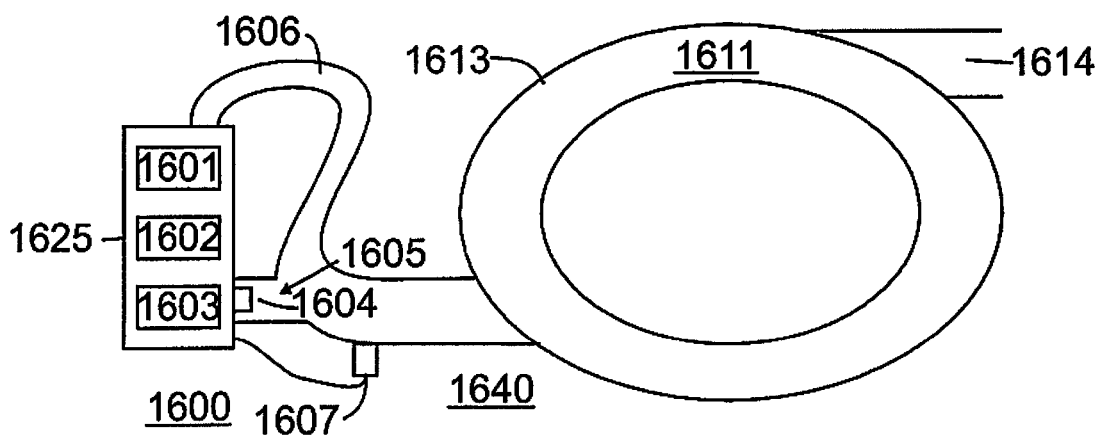
FIG. 16C shows a schematic view of a portable sterilization chamber with a flexible hollow light pipe according to the present invention.

FIG. 16C shows a schematic view of a portable sterilization chamber with a flexible hollow light pipe generally indicated at 1640. The arrangement in FIG. 16C is similar to the arrangement in FIG. 16B, except that sterilization volume is bounded by hollow flexible light pipe 1613 with exit 1614. Light pipe 1613 may be coiled as shown to reduce the size of the apparatus. UV radiation propagates concurrent with air along the length of the light pipe. The light pipe may for example have a length of more than 10 meters. Preferably the light pipe has a length of about 50 meters.

Figures 17A, 17B:
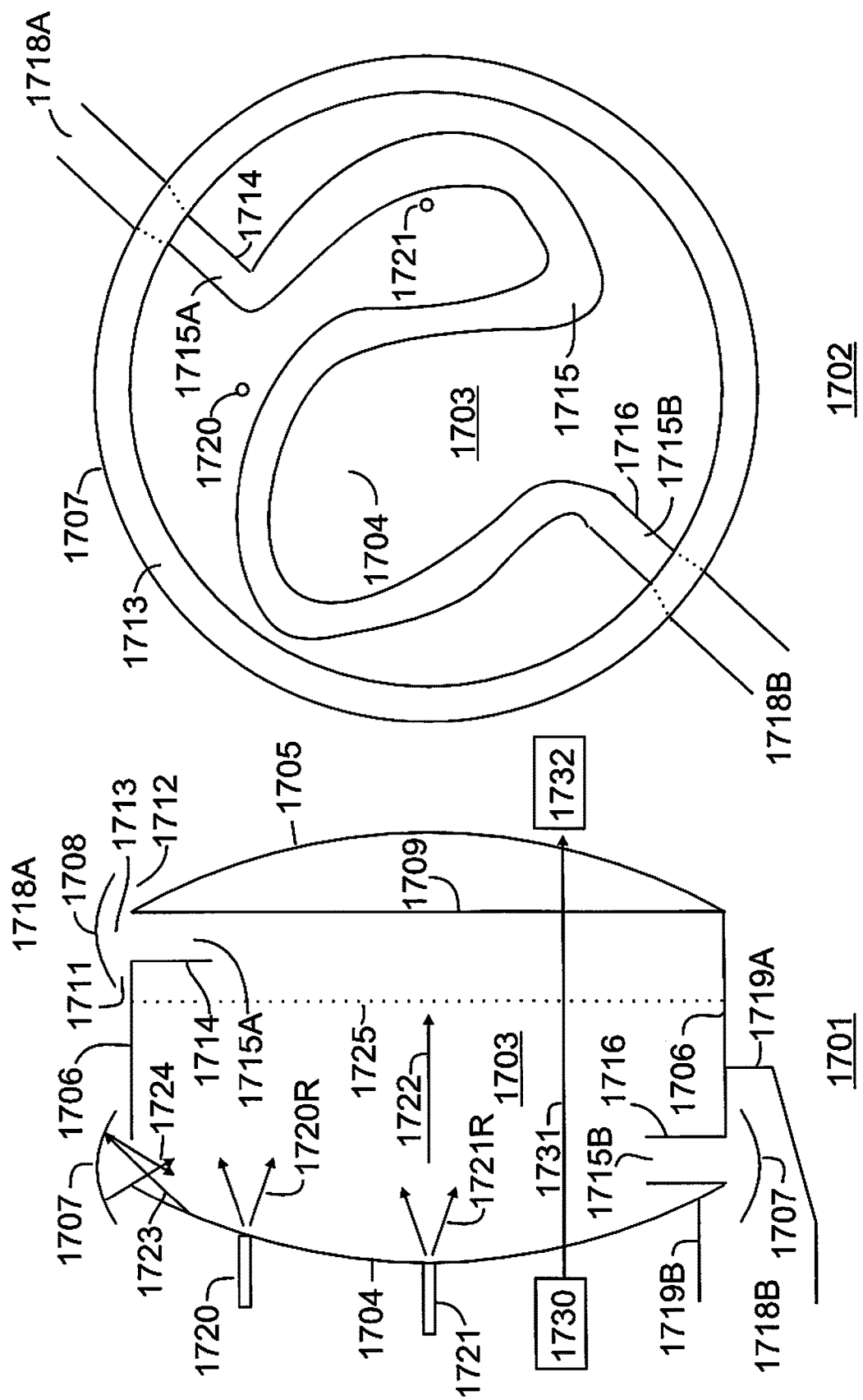
FIG. 17A shows a side view of a further embodiment of a reaction chamber according to the present invention.
FIG. 17B is a transverse cross-sectional view of the reaction chamber of FIG. 17A.

FIG. 17A shows a side view of a further embodiment of a reaction chamber according to the current invention generally indicated at 1701. The reaction chamber has reaction volume 1703 enclosed by concave mirrors 1704 and 1705 and optional side mirror 1706. Optionally mirrors 1704, 1705 and 1706 may be protected by a window comprised of a transparent material as shown schematically at 1709. Optional side mirror may for example have a generally cylindrical shape, possibly with regions removed to allow passage of sample material into or out of reaction volume 1703. Optional side mirror may for example consist of a plurality of reflective sections arranged parallel and displaced from reaction chamber axis 1722 to form a generally polygonal shape. Preferably the polygon has an odd number of sides. Preferably the number of polygon sides is greater than eight. As shown there is an optional gap 1713 between concave mirror 1705 and side mirror 1706. Gap 1713 may for example be an annular ring abutting the entire edge of concave mirror 1705. Alternately gap regions 1713 may abut only selected portions of the edge of concave mirror 1705 wherein the gap regions are selected to correspond with minima in incident flux.

As best seen in FIG. 18B, the flux density for radiation sources has the symmetry of the radiation sources and mirror images thereof. Hence the gap regions are preferably centered intermediate between symmetry axes of the flux density.

Optionally secondary mirror 1707 is positioned proximate to gap 1713 and shaped to reflect flux passing from reaction volume 1703 through gap 1713 back into reaction volume 1703. As illustrated at 1723, a ray passes through gap 1713 and is reflected by secondary mirror back into reaction volume 1703. Preferably secondary mirror 1707 has a generally concave shape with respect to any direction perpendicular to chamber axis 1722 and reflects incident rays to a focal point 1724 within reaction volume 1703. The concave shape may be an arc segment of a circle. Preferably the concave shape is parabolic. The solid of rotation for the concave profile is a semi-toroidal shape. The extent of the semi-toroid secondary mirror matches, or slightly exceeds the extent of gap 1713. As shown at 1707, the secondary mirror has a ring shape. As shown at 1708, the secondary mirror extends only part way around the perimeter proximate to concave mirror 1705. As shown at 1711, there may be a gap between secondary mirror 1708 and edge mirror 1711. As shown at 1712, there may be a gap between secondary mirror 1708 and concave mirror 1705. At least one gap 1711 or 1712 is required for the passage of sample material through gap 1712. A transparent material may be placed proximate to gap 1712 to guide the flow of sample material as shown at 1714 and 1716. In some embodiments the transparent material forms a conduit 1715 wherein sample material enters through region 1715A and exits through region 1715B.

As best shown in FIG. 17B, conduit 1715 may follow any path through reaction volume 1703. Conduit 1715 may for example have a generally spiral shape to increase the residence time of sample material within reaction volume 1703. Conduit 1715 may for example terminate near the center of reaction volume 1703 and sample material deposited proximate to the center moves radially outward toward gaps 1712. As best shown at 1718B, gaps 1711 and 1712 may be enclosed by walls 1719A and 1719B to form external exit conduit 1718B continuous with conduit 1715B. As best seen in FIG. 17B, conduit region 1715A is continuous with external input conduit 1718A.

Reaction chamber 1701 includes one or more radiation input ports as shown at 1720 and 1721. Preferably there are two or more input radiation ports to provide a more homogenous radiation field within reaction volume 1703. Preferably the radiation input ports are arranged at regular angular increments about reaction chamber axis 1722. Note that in the example shown the radiation pattern within reaction volume 1703 has inversion symmetry such that the two sources 1720 and 1721 with angular displacement 90 degrees produce a 4-fold symmetry axis as best seen in FIG. 18B. Radiation sources 1720 and 1721 preferably emit radiation distributions with axis parallel to reaction chamber axis 1722. As shown at 1720R and 1721R, a majority of the radiation emitted is within a cone with axis parallel to chamber axis. Preferably the full cone angle of radiation emitted from sources 1720 and 1721 is 60 degrees or less. More preferably the full cone angle of radiation emitted from sources 1720 and 1721 is 30 degrees or less. The collimation of radiation causes radiation to travel primarily back and forth between concave mirrors 1704 and 1705.

Sources 1720 and 1721 absorb incident radiation flux and consequently it is advantageous to minimize the area of each source. Preferably the radiation sources 1720 and 1721 include an aperture opening into reaction volume 1703 wherein the diameter of the aperture opening is 1 mm or less. Collimating the input radiation through an aperture may be accomplished by placing one or more optical elements (such as lenses) between an emitter and the aperture as described in more detail below. Further, absorption by radiation sources is minimized by radially displacing radiation sources 1720 and 1721 from chamber axis 1722. As the radial displacement is increased, the advantage of reduced absorption is offset by increased loss at gaps 1713. Empirically the inventors discovered that the radial displacement is preferably in the range of 0.5 to 0.75 times the radius of concave mirror 1704. Most preferably the radial displacement is 0.62 times the radius of concave mirror 1704. Note that the radius here is half of the diameter of the mirror and not the radius of curvature. Rays reflected many times primarily between concave mirrors 1704 and 1705 form a sequence of ray segments that are displaced one from the next and nearly parallel (or anti-parallel). The radiation field so produced is highly directional and best described by an order parameter $S=0.5*<3*\cos(\text{theta})-1>$, where theta is the angle between each ray and chamber axis 1722 and the angle brackets signify an average over all rays. The order parameter S so defined is widely used in the art to describe for example the alignment of liquid crystals. Whereas prior art describes reaction chambers with directionally isotropic radiation fields ($S<0.2$), the present invention describes a reaction chamber with a highly directional radiation field. The degree of optical amplification correlates with the order parameter. Preferably the order parameter of the radiation field in the reaction chamber of the present invention is more than 0.3. More preferably the order parameter of the radiation field in the reaction chamber of the present invention is more than 0.5. Most preferably the order parameter of the radiation field in the reaction chamber of the present invention is more than 0.7.

Mirrors 1704, 1705, 1706, 1707 and 1708 may for example be metallic mirrors with a protective coating to prevent oxidation. The preferred metals for the UV and visible ranges are aluminum and silver, respectively. Preferably mirrors 1704, 1705, 1706, 1707 and 1708 are dielectric mirrors with reflectivity optimized for design wavelength and angle of incidence ranges. The design wavelength range is determined by the type of photochemical reaction desired. For example, the optimal design wavelength range is between 255 nm and 275 nm for inactivation of bacteria and viruses. The design angle of incidence for each mirror or region thereof is selected to include a majority of the incident flux. In the example shown in FIG. 17A, the majority of flux incident on concave mirror 1704 is incident at angles between 0 and 20 degrees and hence the reflectivity of concave mirror 1704 is optimized for angles of incidence between 0 and 20 degrees. In the example shown in FIG. 17A, the majority of flux incident on optional side mirror 1706 is incident at angles between 60 degrees and 80 degrees and hence the reflectivity of side mirror 1706 is optimized for angles of incidence between 60 degrees and 80 degrees. Mirrors 1704, 1705, 1706, 1707 and 1708 may be any combination of metallic and dielectric mirrors.

FIGS. 18A, 18B and 18C show sequences of slices through reaction chamber 1701 perpendicular to chamber axis 1722 as shown at 1725. The chamber geometry is identical in each simulation.

FIG. 18A illustrates the radiation field obtained using a prior art diffuse reflector with reflectance 0.97. The radiation field is clearly stronger in proximity to the two emitters. The example shown in FIG. 18A features sources that are not collimated (Lambertian) as prior art cites this distribution as most advantageous. The order parameter for the radiation field in FIG. 18A is 0.0.

FIG. 18B shows the radiation field for a reaction chamber with all aluminum mirrors. This simulation best shows the symmetry of the radiation field in the present invention. The order parameter is 0.67. The average radiation moment of the Teflon chamber 18A and aluminum chamber 18B is the same (169) in both cases. That is radiation intensity times the interaction distance is the same. Hence the overall effectiveness is about the same despite the lower average reflectivity of aluminum (0.92 vs 0.97 for Teflon). That is the geometrical advantages of the present arrangement are sufficient to overcome the lower reflectivity of aluminum. FIG. 18C shows the radiation field in a preferred embodiment of the invention using dielectric reflectors on all surfaces. The order parameter is 0.67 and the average moment is 2397, an improvement of more than 14× over prior art.

Figure 19:
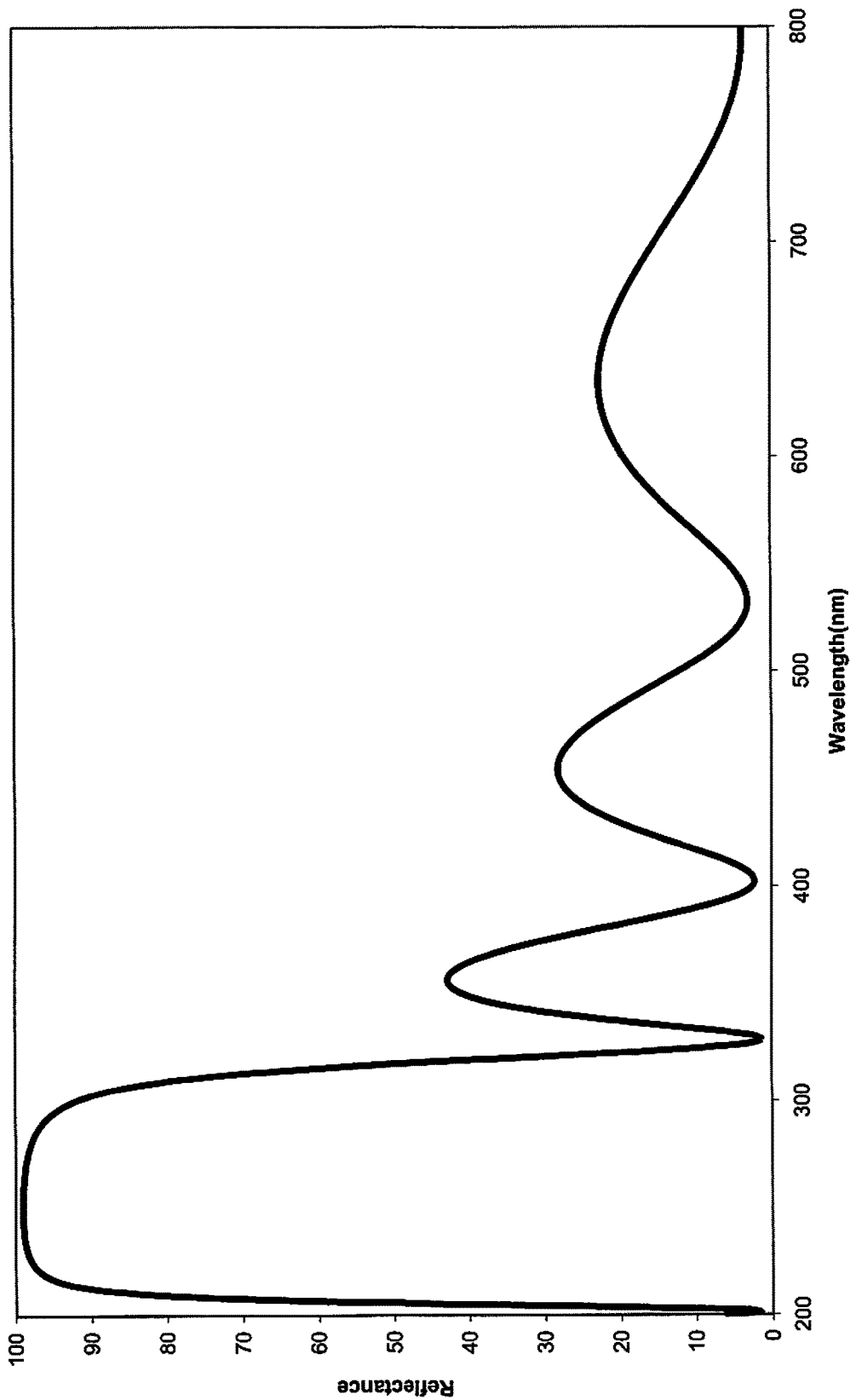
FIG. 19 is a plot of reflectivity vs wavelength of the dielectric stacks of FIG. 17A optimized for UV reflectivity.

The concave mirrors 1704 and 1705 may be comprised of dielectric stacks optimized for UV reflectivity as shown in the reflectivity vs wavelength plot shown in FIG. 19. As seen in FIG. 19, the dielectric stack has windows of near transparency centered near 400 nm, 530 nm and 800 nm. Probe radiation source 1730 may emit probe radiation as shown at 1731 within these spectral windows to interact with sample material and the interaction radiation is detected at detector 1732. For example source 1730 may emit radiation from a commercial LED source at 405 nm and fluorescence from within reaction volume 1703 is detected near 530 nm by detector 1732. For example source 1730 may be an argon laser emitting radiation at 514.5 nm and Raman scattered radiation from sample material in reaction volume 1703 is measured by detector 1732, in this case a spectrometer.

Figure 20A:
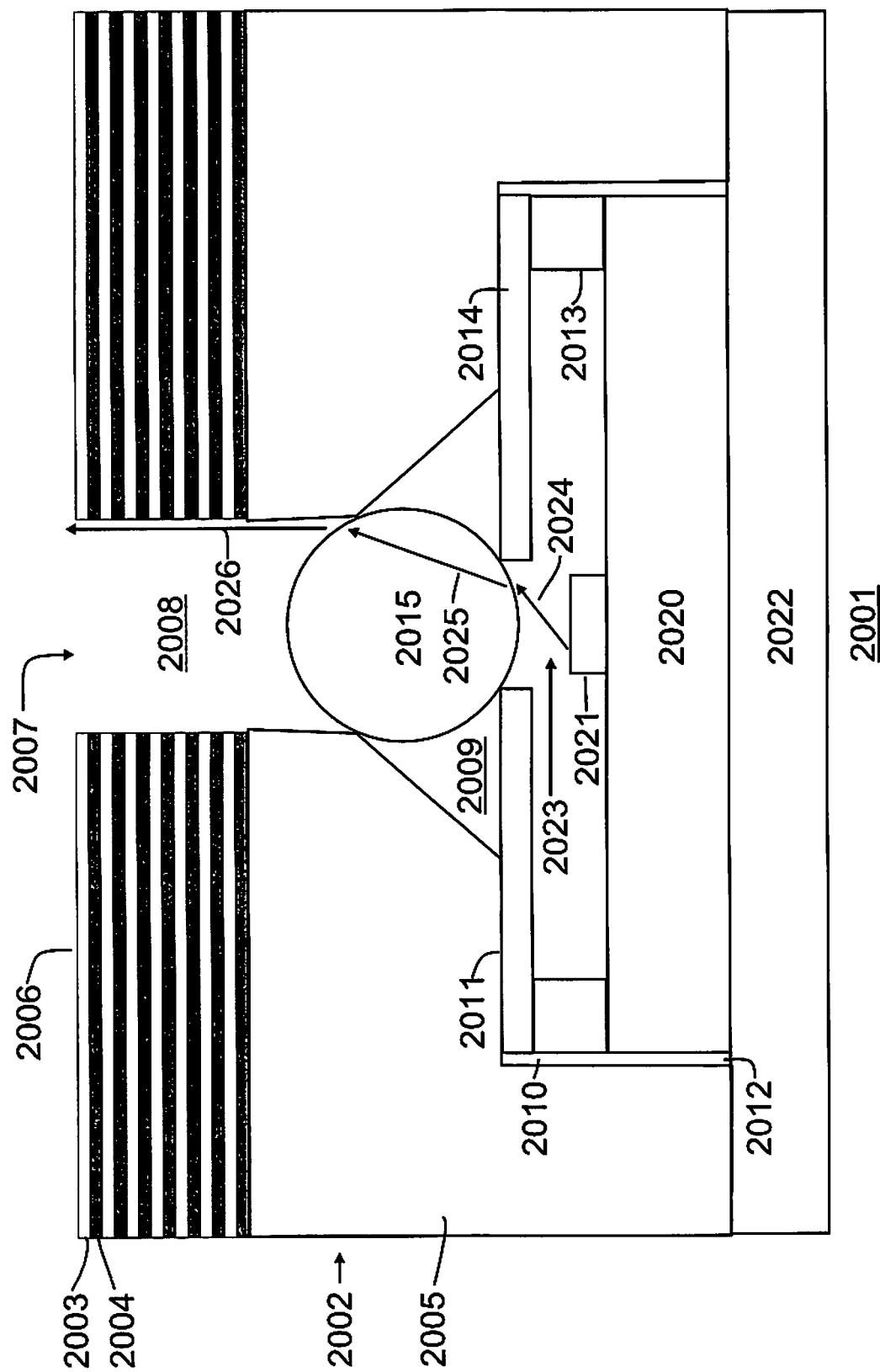
FIG. 20A shows an enlarged schematic side view of a first arrangement to emit radiation from a surface mount LED through an aperture into the chamber of FIG. 17.

FIG. 20A shows an enlarged schematic side view of an arrangement to emit radiation from a surface mount LED through an aperture generally indicated at 2001. The drawing is not to scale and is intended to convey the design ideas. This arrangement may be used as the emitters 1720 and 1721 shown schematically in FIG. 17A. Dielectric mirror 2002 consists of a plurality of alternating layers of low refractive index material 2003 and high refractive index material 2004 on a substrate material 2005. The dielectric mirror has a small hole 2007 with a stepped profile consisting of sections 2008, 2009 and 2010. Section 2008 is a small aperture in the dielectric mirror top surface 2006. Aperture 2008 has a diameter slightly smaller than the diameter of lens 2015. Preferably the diameter of aperture is less than 1 mm. In section 2009 the edge of the hole is angled such that the hole diameter increases with distance from mirror top surface 2006. The angled profile retains and centers lens 2015 on aperture 2008. Lens 2015 may for example be a quartz ball lens. Hole region 2010 has a flat upper surface 2011 and has diameter slightly larger than the diagonal size of surface mount LED 2020. Surface mount LED may for example be 3.5 mm×3.5 mm requiring hole region to have diameter 5 mm or larger to leave a gap 2012 between the edge of the hole region 2010 and surface mount LED 2020. Lens 2015 is retained in region 2009 by ring 2014 with central hole slightly smaller than the diameter of lens 2015. The upper edge of ring 2014 is retained by upper surface 2011 of hole region 2010 and the lower edge of ring 2014 is retained by a spacer 2013. The spacer 2013 is a ring with inner diameter selected such that the lower surface does not contact electronic components on LED 2020. Spacer 2013 functions to provide a small gap 2023 between emitter 2021 of LED 2020 and the bottom surface of lens 2015. The gap is selected such that rays 2024 from emitter 2021 are refracted by lens 2015 as shown at 2025 so as to pass through aperture 2008 least partially collimated as shown at 2026. The gap 2023 is typically less than 1 mm and preferably between 0.1 and 0.2 mm. LED emitter 2021 is mounted on and electrically connected with surface mount package 2020 which has integral anode, cathode and heat sink pads (not shown) electrically connected with printed circuit board 2022.

Figure 20B:
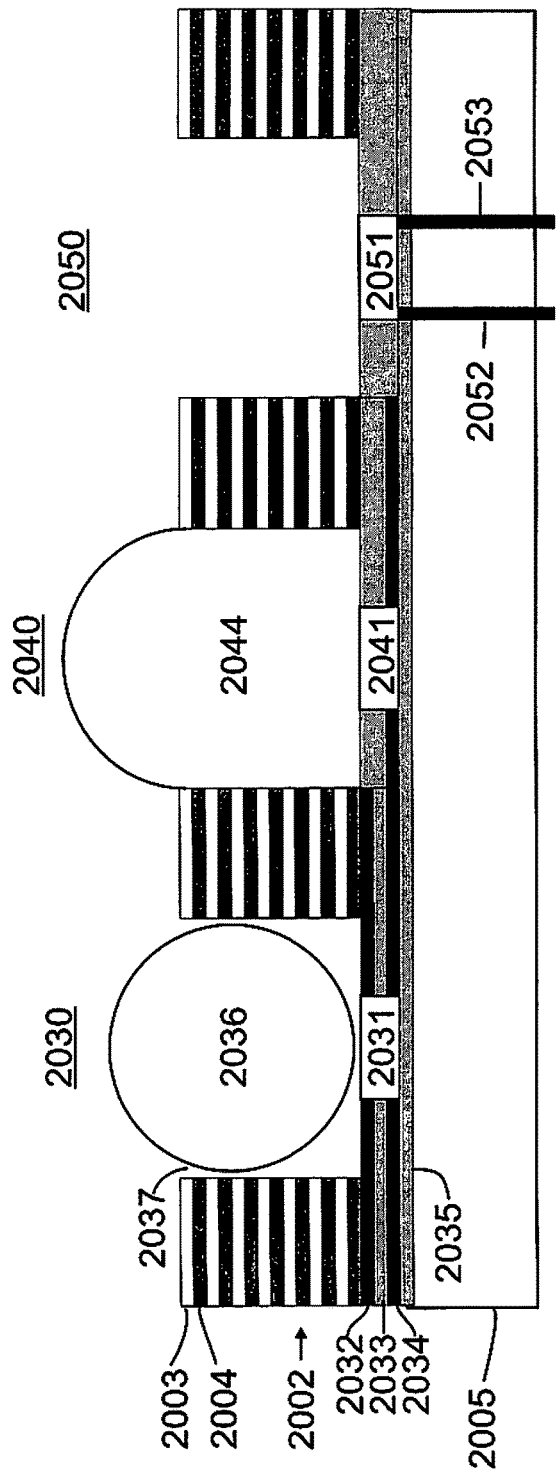
FIG. 20B shows an enlarged schematic side view of a second arrangement to emit radiation from a surface mount LED through an aperture into the chamber of FIG. 17.
Figure 20C:
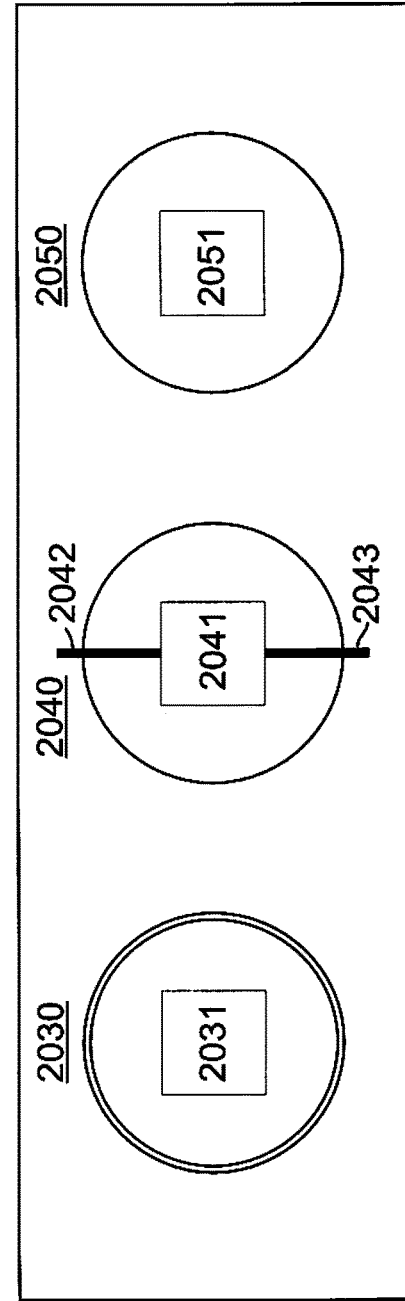
FIG. 20C is a plan view of the arrangement of FIG. 20B.

FIG. 20B and FIG. 20C show side and top views of arrangements for LED emitters embedded in a dielectric mirror. There are three arrangements of optical components and three arrangements of electrical connections. Any of the optical arrangements may be used with any of the electrical arrangements giving a total of nine possible combinations. The arrangements shown in FIGS. 20B and 20C may be the radiation emitters shown at 1720 and 1721 in FIG. 17A. Number labels that coincide with labels in FIG. 20A have the same meanings.

The first optical and electrical arrangements are shown schematically at 2030. Substrate layer 2005 is shown flat in the schematic and is close to flat on the scale shown. However on a larger scale substrate layer 2005 may take the shapes of mirrors 1704, 1705, 1706, 1707 or 1708 in FIG. 17A. Substrate layer may be comprised of a metal, plastic, ceramic, glass or other suitable material shaped to the mirror forms. Substrate 2005 may optionally be covered with electrically insulating layer 2035 if the substrate material is electrically conductive. Insulating layer 2035 may be overlaid by conductive layer 2034 in electrical contact with a first surface of light emitting diode crystal 2031. Conductive layer 2034 is electrically isolated from conductive layer 2032 by insulating layer 2033. Conductive layer is in electrical contact with a second surface of light emitting diode crystal 2031. Hence when a voltage difference is applied between conductive layers 2032 and 2034, electrical current may pass through light emitting diode crystal 2031 and excite emission of electromagnetic radiation. As shown micro lens 2036 is positioned immediately above light emitting diode crystal 2031 in well 2037 and functions to reduce the angular divergence of electromagnetic radiation emitted by the embedded light emitting diode.

The second optical and electrical arrangements are shown schematically at 2040. In this arrangement there is only one electrically conductive layer 2034 overlaid on insulating layer 2035. Electrically conductive layer 2034 is patterned with a network of conductive strips analogous to a printed circuit board, except that the conductive traces are laid over and follow the contours of optical substrate 2005. The anode and cathode of light emitting diode crystal 2041 are connected to separate conductive traces 2042 and 2043. When a voltage is applied across conductive traces 2042 and 2043, light emitting diode crystal emits electromagnetic radiation into integral micro lens 2044 embedded in dielectric mirror 2002. Micro lens 2044 functions to at least partly collimate electromagnetic radiation emitted from the surface of dielectric mirror 2002.

The third optical and electrical arrangements are shown schematically at 2050. In this arrangement the light emitting diode crystal 2051 is embedded in an insulating layer 2033 with no overlaying dielectric layers. The anode and cathode of light emitting diode 2051 are connected to wires 2052 and 2053, respectively that pass through substrate 2005 to external circuitry. In this arrangement, radiation is emitted with a wide angular divergence.

Figure 21B:
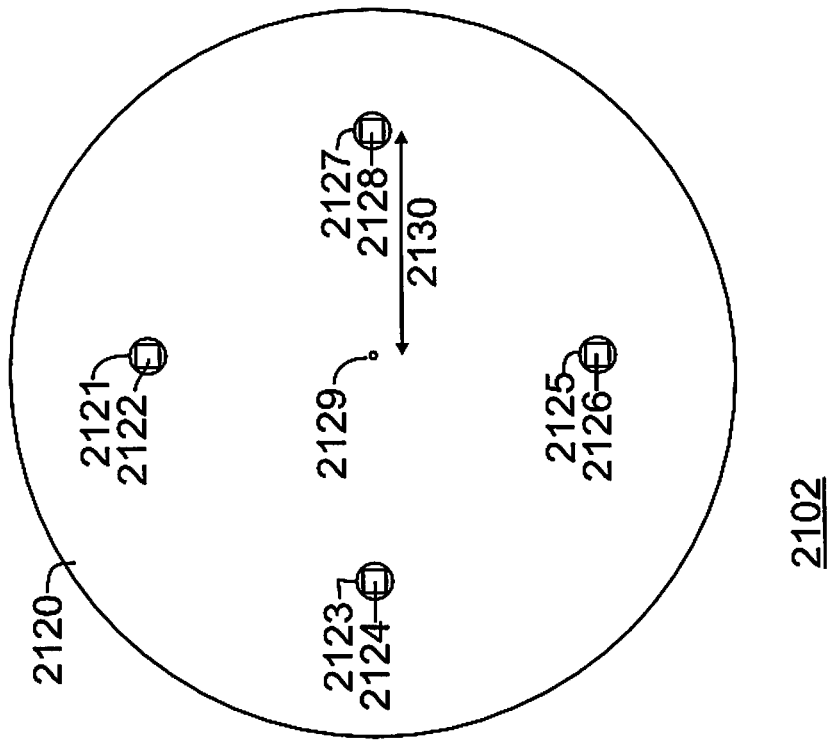
FIG. 21B shows a scale drawing of LED light sources embedded in a dielectric mirror according to the present invention.
Figure 21A:
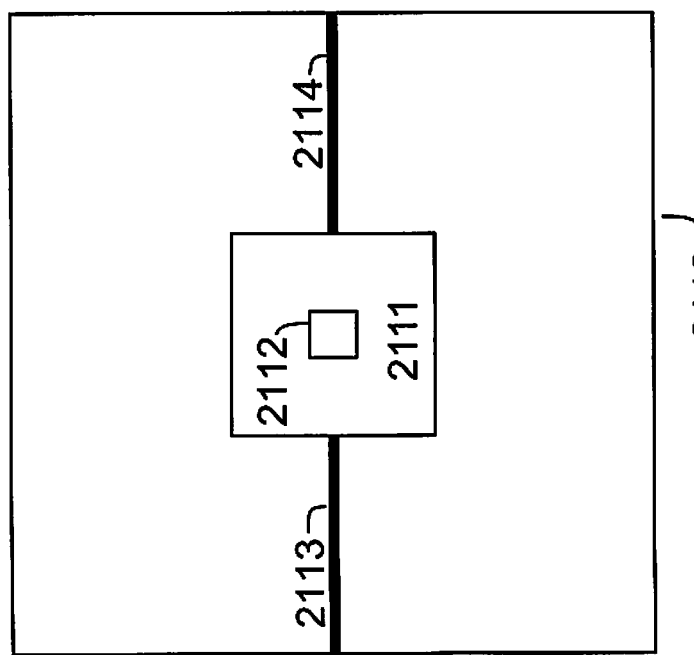
FIG. 21A shows a PRIOR ART scale drawing of a LED mount on a substrate.

FIG. 21A shows a scale drawing of a prior art LED mount on a substrate generally indicated at 2101. FIG. 21B shows a scale drawing of LED light sources embedded in a dielectric mirror according to the present invention generally indicated at 2102. The scale of FIGS. 21A and 21B are the same. In FIG. 21A surface mount LED 2111 with light emitting area 2112 is attached to substrate 2110 and electrically connected to external circuitry by wires 2113 and 2114. The package of surface mount LED 2111 (3.5 mm×3.5 mm) is 19.1× larger than the emitting area (0.8 mm×0.8 mm). The LED emitting area 2112 absorbs incident radiation and the remaining package area is either absorbing or poorly reflective, depending on the choice of commercial LED. The intensity of radiation incident on the package area of surface mount LED 2112 and the areas of wires 2113 and 2114 is attenuated. The maximum driving current and hence radiant output of light emitting area 2112 is determined by the capacity of a heat sink (not shown) to maintain device 2112 below a threshold temperature.

In the mounting scheme of the present invention shown in FIG. 21B light emitting crystal regions 2122, 2124, 2126, and 2128 are embedded in dielectric mirror 2120 and arranged symmetrically about dielectric mirror axis 2129 as illustrated in FIG. 20B. The symmetrical arrangement improves the homogeneity of the radiation field in the reaction chamber. As shown, the radial distance from the axis of the LED regions indicated at 2130 is 0.62 R, where R is the radius of dielectric mirror 2120. Regions 2122, 2124, 2226, and 2128 are overlain by micro lens 2121, 2123, 2125, and 2127, respectively. The micro lens function to reduce the angular divergence of radiation emitted by light emitting regions 2122, 2124, 2126, and 2128. The reduction in angular divergence increases the order parameter and amplification factor of the reaction chamber. As shown the emitting areas are square and the lenses are circular with diameter equal to the diagonal of the square emitting areas. These geometries are commercially available. However circular emitting areas are preferred. The total lens area is 10% of the area of the surface mount LED package 2111 and hence the absorption of incident radiation is reduced by a factor of 10 as compared with prior art. The choice of four emitting areas is for illustrative purposes only. The general concept of the invention is to divide a given emitting area into a plurality N portions where N is any integer greater than or equal to 2. The total area of light emitting crystal is the same as shown in FIG. 21A, but the area is divided into four equal portions 2122, 2124, 2126, and 2128. This has the beneficial effect of reducing the heat load by a factor of approximately four. Because there is more surface area for heat dissipation LED regions 2122, 2124, 2126, and 2128 can be run at a slightly higher current density than LED region 2112 giving higher total radiant flux. As best seen in FIG. 20B, the electrical connections to LED regions 2122, 2124, 2126, and 2128 are beneath dielectric mirror layers and hence do not contribute to absorption of incident flux. Preferably LED regions 2122, 2124, 2126, and 2128 are electrically connected in series, which has the beneficial effect of stabilizing the electric current and balancing the radiant output of the LED regions, again improving the homogeneity of the radiation field in the reaction chamber.

Figure 22:
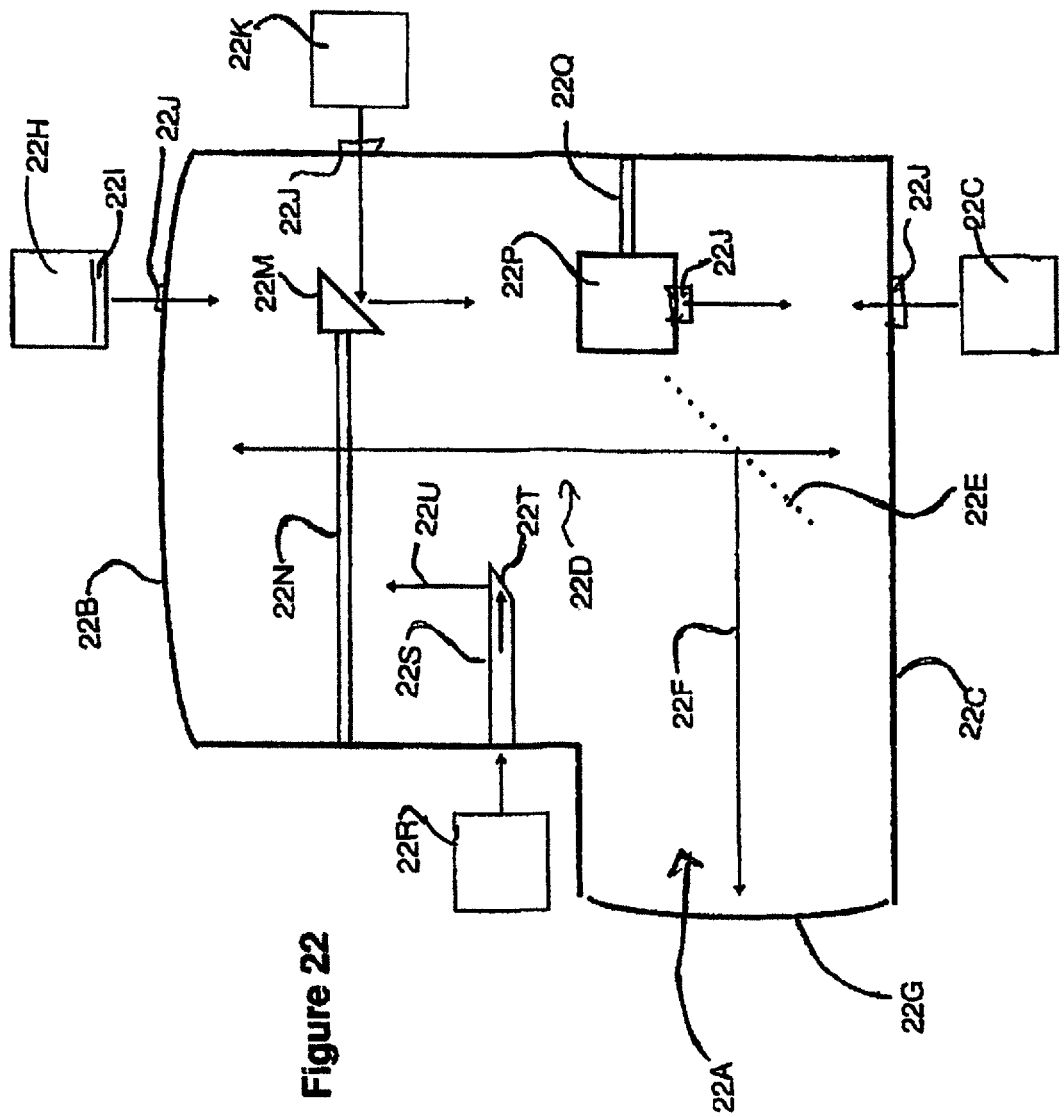
FIG. 22 is a compilation illustration of a number of different alternatives for the location and arrangement of one or more sources of the radiation and different transfer arrangements for carrying the radiation to a required location within the reaction chamber.

Turning now to FIG. 22 there is shown a reaction chamber 22A of a type generally as described above. In this case the chamber 22A is formed by reflective surfaces 22B and 22C where surface 22B is concave and surface 22C is flat. As long as surface 22B is concave, any inaccuracies in the orientation of or plane of the flat mirror 22C do not interfere with the required back and forth reflections that are required. As before, the reflective surfaces 22B and 22C are preferably high reflectivity dielectric mirrors. The side surfaces can be comprised of a reflective material which may be a dielectric or a lower cost, lower reflectivity material. The reaction chamber is shaped such that the side walls receive less radiation intensity per unit area than the surfaces on the optical axis. Hence lower reflectivity at the side walls has a smaller effect on overall optical gain than lower reflectivity of surfaces along the optical axis. The highest optical gain is realized if all surfaces are high reflectivity dielectric mirrors.

The surfaces 22B and 22C generate a center optical axis 22D at right angles to the surfaces and centered on the center of the concave surface 22B.

In this embodiment there is provided a reflective surface or other redirecting surface 22E part way along the axis 22D to form a second axis portion at an angle to the first so that instead of the axis 22D forming a single straight line, it is formed into two sectors or portions at an angle. The second portion 22F cooperates with a second concave mirror 22G.

The figure also shows a number of different alternatives for the location and arrangement of one or more sources of the radiation and different transfer arrangements for carrying the radiation to a required location within the reaction chamber.

Thus at 22H is shown a first possible source which is located external to the chamber and includes a collimation system 221 so that the radiation from the source is carried to the external wall of the chamber and passes through a limiting orifice 22J to enter the chamber at a position offset from the axis 22D as previously described.

A further source of the same construction is located at 22L which can be used as an alternative to or as an addition to the source 22H. Source 22L is located on the flat surface 22C and the latter is located on the concave surface.

As a further alternative, an external source 22K directs radiation through its orifice 22J on one of the side surfaces of the chamber onto a redirecting body 22M carried on a support 22N which redirects the radiation onto the path parallel to but offset from the axis 22D. Preferably support 22N is comprised of a transparent material.

At 22P is provided a further alternative source which in this case is located inside the chamber and carried on mounting support 22Q. The source 22P is located inside a mirrored contained forming a cube with six mirrored surfaces so that the radiation from the source inside the cube is released into the chamber through a small orifice 22J but is then reflected by the external walls of the cube to be retained within the chamber to pass through the multitude of reflective paths as described above.

A yet further alternative is shown at 22R where the source is external and the radiation is carried by a rigid or flexible light pipe such as a fiber optic 22S to a reflective surface 22T causing the radiation to turn to the required direction parallel to the axis 22D.

In another arrangement, not shown, the source can be a radiant cylindrical tube located within the chamber preferably at an orientation parallel to the optical axis but optionally at other orientations such as right angle to the axis. If parallel to the axis, the tube can be located on the axis or spaced outwardly from the axis. The preferred or optimum position locates the tube at a spacing from the axis of one half of the radius of the concave surface.

In another arrangement not shown, the concave mirror can be formed with a central section at the axis which is a dielectric mirror and on outer ring of a material of reduced reflectivity such as polished aluminum. While this of course reduces the total efficiency of reflections and the maximum increase in paths due to the lower reflectivity of the outer ring of material, this may be more suitable in some circumstances for reduced cost and bearing in mind that the majority of the increase in paths is generated adjacent the center or axis of the concave mirror with a reduced effect oat outwardly spaced locations. Thus an arrangement of best efficiency/cost can be produced by selecting the sizes of the surfaces and the proportion of the central area which is formed of the dielectric mirror.

The invention claimed is:

1. A method for sterilizing a forced air flow in a duct comprising:
passing the forced air flow through the duct in a stream;
introducing electromagnetic radiation into the duct from at least one source at selected wavelengths operable to sterilize the forced air flow;
directing the electromagnetic radiation in the duct along a specific path; and
arranging at least two reflective surfaces in the duct at spaced positions so as to cause reflections back and forth between said at least two reflective surfaces and thus increase the probability of interaction of the electromagnetic radiation with the forced air flow by forming a plurality of paths which increase an optical path length of the electromagnetic radiation through the duct;
wherein at least one of said at least two reflective surfaces of the duct comprises a concave mirror arranged to cause reflections of the electromagnetic radiation back and forth within a volume between said at least two reflective surfaces;
wherein the electromagnetic radiation is at least partially collimated to travel primarily back and forth between said at least two reflective surfaces;
wherein more than 75% of said at least two reflective surfaces has a specular reflection coefficient for the electromagnetic radiation at the selected wavelengths greater than 90%;
and wherein a majority of said plurality of paths include at least ten reflections.

2. The method according to claim 1 wherein the forced air flow is generated by a fan having fan blades and wherein at least one of said at least two reflective surfaces is provided by at least one component of the fan.

3. The method according to claim 2 wherein another of said at least two reflective surfaces comprises a mirror at a position spaced radially outwardly from the fan blades.

4. The method according to claim 2 the fan blades have at least one of said at least two reflective surfaces which is different in shape from an air engaging surface of the fan blades.

5. The method according to claim 4 wherein the air engaging surface is transparent so that the electromagnetic radiation passes through to said at least one of said at least two reflective surfaces.

6. The method according to claim 1 wherein at least one reflective surface of said at least two reflective surfaces comprises a dielectric mirror.

7. The method according to claim 6 wherein the dielectric mirror has reflectivity at the selected wavelengths greater than 99%.

8. The method according to claim 6 wherein the dielectric mirror is formed by a plurality of layers of dielectric materials and is arranged in a stack and wherein the stack has a first area arranged with selected thicknesses of the plurality of layers such that an incident ray of the electromagnetic radiation is reflected by the stack if the angle of incidence of the incident ray falls within a first predetermined range of angles and is transmitted through the stack if the angle of incidence of the incident ray falls in a different predetermined range of angles and wherein the stack has a second area arranged with selected thicknesses of the plurality of layers such that the incident ray is reflected by the stack if the angle of incidence of the incident ray falls within a second predetermined range of angles different from the first predetermined range of angles and is transmitted through the stack if the angle of incidence of the ray falls in a different predetermined range of angles.

9. The method according to claim 6 wherein the electromagnetic radiation has a first wavelength selected so that the dielectric mirror reflects the electromagnetic radiation at the first wavelength at a first value and using a further electromagnetic radiation to obtain information relating to reactant materials in the duct where the further electromagnetic radiation has a second wavelength different from said first wavelength at which the dielectric mirror is substantially transparent.

10. The method according to claim 6 wherein the dielectric mirror comprises a plurality of separate dielectric mirror components each formed by a plurality of layers of dielectric materials arranged in a stack;
said plurality of separate dielectric mirror components being mounted on a flexible supporting substrate with each of said plurality of separate dielectric mirror components being movable relative to a next one of said plurality of separate dielectric mirror components to follow a flexing movement of the flexible supporting substrate.

11. The method according to claim 1 wherein there is provided an additional reflective surface between said at least two reflective surfaces.

12. The method according to claim 1 wherein the concave mirror defines at least one center optical axis extending therebetween along which the reflections pass and wherein a location at which the electromagnetic radiation enters is located at a position offset from said at least one center optical axis so that a locus of the reflections moves toward said at least one center optical axis.

13. The method according to claim 1 wherein a location at which the electromagnetic radiation enters is located at a position on at least one of said at least two reflective surfaces.

14. The method according to claim 1 wherein an offset between each path of the electromagnetic radiation and a next path of the electromagnetic radiation after a reflection is less than a width of the paths of the electromagnetic radiation so that the paths of the electromagnetic radiation form a complete curtain.

15. The method according to claim 1 wherein there is provided an inlet port for admitting reactive materials and an outlet port for discharging product materials and wherein there is provided absorbing surfaces formed and shaped to stop transmission of electromagnetic radiation from the interior of the duct to an exterior location.

16. The method according to claim 1 wherein the duct has at least one port between an interior and an exterior and wherein there is provided a mirror outside of said at least one port so as to reflect escaping electromagnetic radiation back into the duct.

17. The method according to claim 16 wherein the mirror is a focusing mirror so as to reflect escaping electromagnetic radiation back through said at least one port into the duct.

18. The method according to claim 1 wherein the electromagnetic radiation is UVC radiation and a reactive material in the duct is a microorganism selected from the list of bacteria, virus, protozoan, helminth, yeast, mould or fungus and said UVC radiation inactivates said microorganism.

19. The method according to claim 1 wherein electromagnetic radiation is transferred from a first location within the duct to a second location within the duct by a light pipe, which can be flexible or rigid.

20. The method according to claim 1 wherein the electromagnetic radiation is introduced by said at least one source arranged to emit the electromagnetic radiation mainly in a direction of an optical axis of the at least two reflective surfaces.

21. The method according to claim 20 wherein the optical axis is a single straight path or wherein the optical axis is comprised of a plurality of straight paths where a re-directing body generates a second path at an angle to the single straight path.

22. The method according to claim 1 wherein a source of at least some of the electromagnetic radiation is external to the duct and the electromagnetic radiation from a radiation emitting area of said source is introduced into the duct from said source through an orifice wherein the electromagnetic radiation from said radiation emitting area is at least partially collimated to pass through the orifice and directed such that substantially all of the electromagnetic radiation passes through the orifice and wherein the orifice is sized and positioned to reduce an amount of the electromagnetic radiation exiting the duct through the orifice and being re-absorbed by the source.

23. The method according to claim 1 wherein at least one of said at least two reflective surfaces is formed by a mirror layer carried on a substrate;
- wherein the electromagnetic radiation is introduced into the duct by at least one LED;
- wherein said at least one LED is carried on the substrate;
- wherein the substrate carries electrically conductive components of an electrically conductive layer for providing power to said at least one LED;
- wherein the substrate additionally carries thermally conductive components for conducting heat away from said at least one LED; and
- wherein said at least one LED is located at an orifice in the mirror layer.

* * * * *